(12) United States Patent
Kawaue et al.

(10) Patent No.: US 8,367,297 B2
(45) Date of Patent: Feb. 5, 2013

(54) RESIST COMPOSITION, METHOD OF FORMING RESIST PATTERN, NOVEL COMPOUND AND ACID GENERATOR

(75) Inventors: Akiya Kawaue, Kawasaki (JP); Yoshiyuki Utsumi, Kawasaki (JP); Shinichi Hidesaka, Kawasaki (JP); Natsuko Maruyama, Kawasaki (JP)

(73) Assignee: Tokyo Ohka Kogyo Co., Ltd., Kanagawa-ken (JP)

( * ) Notice: Subject to any disclaimer, the term of this patent is extended or adjusted under 35 U.S.C. 154(b) by 375 days.

(21) Appl. No.: 12/654,066

(22) Filed: Dec. 9, 2009

(65) Prior Publication Data

US 2010/0196820 A1    Aug. 5, 2010

(30) Foreign Application Priority Data

Dec. 10, 2008  (JP) ................. P2008-314979

(51) Int. Cl.
| | |
|---|---|
| *G03F 7/004* | (2006.01) |
| *G03F 7/30* | (2006.01) |
| *C07D 333/00* | (2006.01) |
| *C07C 69/66* | (2006.01) |
| *C07C 309/06* | (2006.01) |
| *C07C 309/19* | (2006.01) |

(52) U.S. Cl. .............. 430/270.1; 430/326; 430/910; 430/921; 430/922; 549/79; 560/185; 562/100

(58) Field of Classification Search .......... 430/270.1, 430/326, 910, 921, 922; 560/185; 549/79; 562/100

See application file for complete search history.

(56) References Cited

U.S. PATENT DOCUMENTS

| | | | | |
|---|---|---|---|---|
| 5,191,124 A | * | 3/1993 | Schwalm et al. ............ | 568/18 |
| 5,679,496 A | * | 10/1997 | Ohsawa et al. ............ | 430/270.1 |
| 5,945,517 A | | 8/1999 | Nitta et al. | |
| 6,153,733 A | | 11/2000 | Yukawa et al. | |
| 6,416,928 B1 | * | 7/2002 | Ohsawa et al. ............ | 430/270.1 |
| 6,551,758 B2 | * | 4/2003 | Ohsawa et al. ............ | 430/270.1 |
| 6,692,893 B2 | * | 2/2004 | Ohsawa et al. ............ | 430/270.1 |
| 7,074,543 B2 | | 7/2006 | Iwai et al. | |
| 7,217,492 B2 | * | 5/2007 | Yoneda et al. ............ | 430/270.1 |
| 2002/0076643 A1 | * | 6/2002 | Ohsawa et al. ............ | 430/270.1 |

FOREIGN PATENT DOCUMENTS

| | | |
|---|---|---|
| JP | 09-208554 | 8/1997 |
| JP | 11-035551 | 2/1999 |
| JP | 11-035552 | 2/1999 |
| JP | 11-035573 | 2/1999 |
| JP | 11-322707 | 11/1999 |
| JP | 2003-241385 | 8/2003 |
| JP | 2005-037888 | 2/2005 |
| JP | 2005-336452 | 12/2005 |
| JP | 2006-259582 | 9/2006 |
| WO | 2004/074242 | 9/2004 |

* cited by examiner

*Primary Examiner* — John Chu

(74) *Attorney, Agent, or Firm* — Wenderoth, Lind & Ponack, L.L.P.

(57) ABSTRACT

A resist composition including a base component (A) which exhibits changed solubility in an alkali developing solution under action of acid and an acid-generator component (B) which generates acid upon exposure, the acid-generator component (B) including an acid generator (B1) containing a compound having a cation moiety represented by general formula (I) (in the formula, $R^5$ represents a hydrogen atom or an organic group of 1 to 30 carbon atoms which may have a substituent; and $Q^5$ represents a single bond or a divalent linking group).

[Chemical Formula 1]

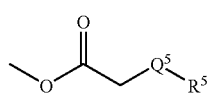

(I)

12 Claims, No Drawings

RESIST COMPOSITION, METHOD OF FORMING RESIST PATTERN, NOVEL COMPOUND AND ACID GENERATOR

TECHNICAL FIELD

The present invention relates to a resist composition, a method of forming a resist pattern using the same, a novel compound useful as an acid generator for a resist composition, and an acid generator.

Priority is claimed on Japanese Patent Application No. 2008-314979, filed Dec. 10, 2008, the content of which is incorporated herein by reference.

BACKGROUND ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film. A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have lead to rapid progress in the field of pattern miniaturization.

Typically, these miniaturization techniques involve shortening the wavelength of the exposure light source. Conventionally, ultraviolet radiation typified by g-line and i-line radiation has been used, but nowadays KrF excimer lasers and ArF excimer lasers are starting to be introduced in mass production. Furthermore, research is also being conducted into lithography techniques that use an exposure light source having a wavelength shorter than these excimer lasers, such as $F_2$ excimer lasers, electron beam, extreme ultraviolet radiation (EUV), and X-ray.

Resist materials for use with these types of exposure light sources require lithography properties such as a high resolution capable of reproducing patterns of minute dimensions, and a high level of sensitivity to these types of exposure light sources. As a resist material which satisfies these conditions, a chemically amplified resist is used, which includes a base resin that exhibits a changed solubility in an alkali developing solution under action of acid and an acid generator that generates acid upon exposure. For example, a chemically amplified positive resist contains, as a base resin, a resin which exhibits increased solubility in an alkali developing solution under action of acid, and an acid generator. In the formation of a resist pattern, when acid is generated from the acid generator upon exposure, the exposed portions become soluble in an alkali developing solution.

Until recently, polyhydroxystyrene (PHS) or derivative resins thereof in which the hydroxyl groups are protected with acid-dissociable, dissolution-inhibiting groups (PHS-based resins), which exhibit high transparency to a KrF excimer laser (248 nm), have been used as the base resin component of chemically amplified resists. However, because PHS-based resins contain aromatic rings such as benzene rings, their transparency is inadequate for light with wavelengths shorter than 248 nm, such as light of 193 nm. Accordingly, chemically amplified resists that use a PHS-based resin as the base resin component suffer from low levels of resolution in processes that use light of 193 nm. As a result, resins that contain structural units derived from (meth)acrylate esters within the main chain (acrylic resins) are now widely used as base resins for resists that use ArF excimer laser lithography, as they exhibit excellent transparency in the vicinity of 193 nm. In the case of a positive resist, as the base resin, those which have a structural unit derived from (meth)acrylate ester including an aliphatic polycyclic group-containing, tertiary alkyl ester-type acid dissociable, dissolution inhibiting group, such as a structural unit derived from 2-alkyl-2-adamantyl(meth)acrylate are mainly used (for example, see Patent Document 1).

Here, the term "(meth)acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position. The term "(meth)acrylic acid" is a generic term that includes either or both of acrylic acid having a hydrogen atom bonded to the α-position and methacrylic acid having a methyl group bonded to the α-position.

On the other hand, as acid generators usable in a chemically amplified resist, various types have been proposed including, for example, onium salt acid generators such as iodonium salts and sulfonium salts; oxime sulfonate acid generators; diazomethane acid generators; nitrobenzylsulfonate acid generators; iminosulfonate acid generators; and disulfone acid generators.

Currently, as acid generators, onium salt acid generators having an onium ion such as triphenylsulfonium as the cation moiety are used (for example, see Patent Document 2).

[Patent Document 1] Japanese Unexamined Patent Application, First Publication No. 2003-241385
[Patent Document 2] Japanese Unexamined Patent Application, First Publication No. 2005-037888

SUMMARY OF THE INVENTION

In recent years, as requirements for high resolution increase with progress in the miniaturization of resist patterns, further improvement in various lithography properties has been demanded. Further, development of a novel resist material has been demanded.

In the aforementioned onium salt-based acid generator having a cation such as triphenylsulfonium, the cation exhibits a relatively high hydrophobicity, and the acid generator exhibits excellent affinity for the base component of a resist composition and an excellent solubility in an organic solvent. Therefore, it is presumed that such an acid generator contributes to improvement in various lithography properties.

However, as the hydrophobicity of the cation becomes higher, the solubility of the acid generator in an alkali developing solution tends to become poor. When the solubility of the acid generator in an alkali developing solution becomes poor, the acid generator cannot be satisfactorily dissolved during development. As a result, problems of defects and footing of the pattern is likely to occur. When defects are generated, for example, a problem occurs in that the removability of the space portions becomes poor.

The term "defects" refers to general abnormalities within a resist film that are detected when observed from directly above the developed resist pattern using, for example, a surface defect detection apparatus (product name: "KLA") manufactured by KLA-TENCOR Corporation. Examples of these abnormalities include post-developing scum, foam, dust, bridges formed between resist patterns, color irregularities and deposit.

Therefore, there is a demand for a compound useful as an acid generator for a resist composition, which can achieve excellent solubility in a developing solution, and also excellent lithography properties.

The present invention takes the above circumstances into consideration, with an object of providing a novel compound useful as an acid generator for a resist composition, an acid generator including the compound, a resist composition containing the acid generator, and a method of forming a resist pattern using the resist composition.

For solving the above-mentioned problems, the present invention employs the following aspects.

Specifically, a first aspect of the present invention is a resist composition including a base component (A) which exhibits changed solubility in an alkali developing solution under action of acid and an acid-generator component (B) which generates acid upon exposure, the acid-generator component (B) including an acid generator (B1) containing a compound having a group represented by general formula (I) shown below On a cation moiety thereof.

[Chemical Formula 1]

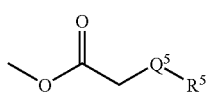

(I)

In formula (I), $R^5$ represents a hydrogen atom or an organic group of 1 to 30 carbon atoms which may have a substituent; and $Q^5$ represents a single bond or a divalent linking group.

A second aspect of the present invention is a method of forming a resist pattern, including forming a resist film on a substrate using a resist composition according to the first aspect, subjecting the resist film to exposure, and subjecting the resist film to alkali developing to form a resist pattern.

A third aspect of the present invention is a compound represented by general formula (b1-11) shown below.

[Chemical Formula 2]

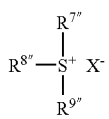

(b1-11)

In formula (b1-11), each of $R^{7\prime\prime}$ to $R^{9\prime\prime}$ independently represents an aryl group or an alkyl group, and two of $R^{7\prime\prime}$ to $R^{9\prime\prime}$ may be mutually bonded to form a ring with the sulfur atom, provided that at least one of $R^{7\prime\prime}$ to $R^{9\prime\prime}$ represents a substituted aryl group having a group represented by general formula (I) shown below as a substituent; and $X^-$ represents an anion.

[Chemical Formula 3]

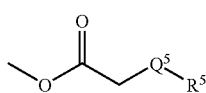

(I)

In formula (I), $R^5$ represents a hydrogen atom or an organic group of 1 to 30 carbon atoms which may have a substituent; and $Q^5$ represents a single bond or a divalent linking group.

A fourth aspect of the present invention is an acid generator including the compound of the third aspect.

In the present description and claims, an "alkyl group" includes linear, branched or cyclic, monovalent saturated hydrocarbon, unless otherwise specified.

The term "alkylene group" includes linear, branched or cyclic divalent saturated hydrocarbon, unless otherwise specified.

A "lower alkyl group" is an alkyl group of 1 to 5 carbon atoms.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

The term "aliphatic" is a relative concept used in relation to the term "aromatic", and defines a group or compound that has no aromaticity.

The term "structural unit" refers to a monomer unit that contributes to the formation of a polymeric compound (polymer, copolymer).

The term "exposure" is used as a general concept that includes irradiation with any form of radiation.

According to the present invention, there are provided a novel compound useful as an acid generator for a resist composition, an acid generator including the compound, a resist composition containing the acid generator, and a method of forming a resist pattern using the resist composition.

DETAILED DESCRIPTION OF THE INVENTION

<<Resist Composition>>

The resist composition according to the first aspect of the present invention includes a base component (A) which exhibits changed solubility in an alkali developing solution under action of acid (hereafter, referred to as "component (A)") and an acid-generator component (B) which generates acid upon exposure (hereafter, referred to as "component (B)").

With respect to a resist film formed using the resist composition, when a selective exposure is conducted during formation of a resist pattern, acid is generated from the component (B), and the generated acid acts on the component (A) to change the solubility of the component (A) in an alkali developing solution. As a result, the solubility of the exposed portions in an alkali developing solution is changed, whereas the solubility of the unexposed portions in an alkali developing solution remains unchanged. Therefore, the exposed portions are dissolved and removed by alkali developing in the case of a positive resist composition, whereas unexposed portions are dissolved and removed in the case of a negative resist composition, and hence, a resist pattern can be formed.

The resist composition of the present invention may be either a negative resist composition or a positive resist composition.

Furthermore, the resist composition of the present invention may include a nitrogen-containing organic compound (D) (hereafter, referred to as "component (D)"), in addition to the component (A) and the component (B).

Moreover, the resist composition of the present invention may include a fluorine-containing compound component (hereafter, referred to as "component (F)"), in addition to the component (A) and the component (B), or in addition to the component (A), the component (B) and the component (D).

<Component (A)>

As the component (A), an organic compound typically used as a base component for a chemically amplified resist composition can be used alone, or two or more of such organic compounds can be mixed together.

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The organic compounds having a molecular weight of 500 or more are broadly classified into low molecular weight organic compounds having a molecular weight of 500 to less than 2,000 (hereafter, referred to as "low molecular weight materials") and high molecular weight resins having a molecular weight of 2,000 or more (namely, "polymeric materials"). Generally, as the aforementioned low molecular weight compound, a non-polymer is used. With respect to the aforementioned resin (polymer or copolymer), the molecular weight is the polystyrene equivalent value determined by gel permeation chromatography (GPC). Hereafter, a "resin" refers to a resin having a molecular weight of 2,000 or more.

As the component (A), a resin which exhibits changed solubility in an alkali developing solution under action of acid may be used. Alternatively, as the component (A), a low molecular weight compound which exhibits changed solubility in an alkali developing solution under action of acid may be used.

When the resist composition of the present invention is a negative resist composition, for example, as the component (A), a base component that is soluble in an alkali developing solution is used, and a cross-linking agent is blended in the negative resist composition.

In the negative resist composition, when acid is generated from the component (B) upon exposure, the action of the generated acid causes cross-linking between the base component and the cross-linking agent, and the cross-linked portion becomes insoluble in an alkali developing solution. Therefore, in the formation of a resist pattern, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

Generally, as the component (A) for a negative resist composition, a resin that is soluble in an alkali developing solution (hereafter, referred to as "alkali-soluble resin") is used.

As the alkali-soluble resin, it is preferable to use a resin having a structural unit derived from at least one of α-(hydroxyalkyl)acrylic acid and a lower alkyl ester of α-(hydroxyalkyl)acrylic acid, or a resin having a fluorinated alcohol as disclosed in Japanese Unexamined Patent Application, First Publication No. 2005-336452 or 2006-259582, as it enables formation of a satisfactory resist pattern with minimal swelling. Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group is preferable, as it enables formation of a resist pattern with minimal swelling. The amount of the cross-linker added is preferably within a range from 1 to 50 parts by weight, relative to 100 parts by weight of the alkali-soluble resin.

When the resist composition of the present invention is a positive resist composition, as the component (A), a base component (A') which exhibits increased solubility in an alkali developing solution by action of acid (hereafter, referred to as "component (A')") is used.

The component (A') is insoluble in an alkali developing solution prior to exposure, and when acid is generated from the component (B) upon exposure, the solubility of the component (A') in an alkali developing solution increases. Therefore, in the formation of a resist pattern, by conducting selective exposure of a resist film formed by applying the positive resist composition onto a substrate, the exposed portions changes from an insoluble state to a soluble state in an alkali developing solution, whereas the unexposed portions remain insoluble in an alkali developing solution, and hence, a resist pattern can be formed by alkali developing.

In the resist composition of the present invention, the component (A) is preferably a base component (A') which exhibits increased solubility in an alkali developing solution under action of acid. That is, the resist composition of the present invention is preferably a positive resist composition.

The component (A') may be a resin component (A1) that exhibits increased solubility in an alkali developing solution under the action of acid (hereafter, frequently referred to as "component (A1)"), a low molecular weight material (A2) that exhibits increased solubility in an alkali developing solution under the action of acid (hereafter, frequently referred to as "component (A2)"), or a mixture thereof.

[Component (A1)]

As the component (A1), a resin component (base resin) typically used as a base component for a chemically amplified resist composition can be used alone, or two or more of such resin components can be mixed together.

In the present invention, it is preferable that the component (A1) include a structural unit derived from an acrylate ester.

In the present descriptions and claims, the term "structural unit derived from an acrylate ester" refers to a structural unit which is formed by the cleavage of the ethylenic double bond of an acrylate ester.

The term "acrylate ester" is a generic term that includes acrylate esters having a hydrogen atom bonded to the carbon atom on the α-position, and acrylate esters having a substituent (an atom other than a hydrogen atom or a group) bonded to the carbon atom on the α-position. As the substituent, a lower alkyl group or a halogenated lower alkyl group can be used.

With respect to the "structural unit derived from an acrylate ester", the "α-position (the carbon atom on the α-position)" refers to the carbon atom having the carbonyl group bonded thereto, unless specified otherwise.

With respect to the acrylate ester, specific examples of the lower alkyl group for the substituent at the α-position include linear or branched alkyl groups such as a methyl group, an ethyl group, a propyl group, an isopropyl group, an n-butyl group, an isobutyl group, a tert-butyl group, a pentyl group, an isopentyl group, and a neopentyl group.

Specific examples of the halogenated lower alkyl group include groups in which part or all of the hydrogen atoms of the aforementioned "lower alkyl group for the substituent at the α-position" are substituted with halogen atoms. Examples of the halogen atom include a fluorine atom, a chlorine atom, a bromine atom and an iodine atom, and a fluorine atom is particularly desirable.

In the present invention, it is preferable that a hydrogen atom, a lower alkyl group or a halogenated lower alkyl group is bonded to the α-position of the acrylate ester, a hydrogen atom, a lower alkyl group or a fluorinated lower alkyl group is more preferable, and in terms of industrial availability, a hydrogen atom or a methyl group is the most desirable.

In the resist composition of the present invention, it is particularly desirable that the component (A1) include a structural unit (a1) derived from an acrylate ester containing an acid dissociable, dissolution inhibiting group.

Further, it is preferable that the component (A1) include a structural unit (a2) derived from an acrylate ester containing a lactone-containing cyclic group, as well as the structural unit (a1).

Furthermore, it is preferable that the component (A1) include a structural unit (a3) derived from an acrylate ester containing a polar group-containing aliphatic hydrocarbon group, as well as the structural unit (a1), or the structural unit (a1) and the structural unit (a2).

(Structural Unit (a1))

The structural unit (a1) is a structural unit derived from an acrylate ester containing an acid dissociable, dissolution inhibiting group.

As the acid dissociable, dissolution inhibiting group in the structural unit (a1), any of the groups that have been proposed as acid dissociable, dissolution inhibiting groups for the base resins of chemically amplified resists can be used, provided the group has an alkali dissolution-inhibiting effect that renders the entire component (A1) insoluble in an alkali developing solution prior to dissociation, and then following dissociation by action of acid, increases the solubility of the entire component (A1) in the alkali developing solution. Generally, groups that form either a cyclic or chain-like tertiary alkyl ester with the carboxyl group of the (meth)acrylic acid, and acetal-type acid dissociable, dissolution inhibiting groups such as alkoxyalkyl groups are widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

The term "aliphatic branched" refers to a branched structure having no aromaticity. The "aliphatic branched, acid dissociable, dissolution inhibiting group" is not limited to be constituted of only carbon atoms and hydrogen atoms (not limited to hydrocarbon groups), but is preferably a hydrocarbon group. Further, the "hydrocarbon group" may be either saturated or unsaturated, but is preferably saturated.

As an example of the aliphatic branched, acid dissociable, dissolution inhibiting group, for example, a group represented by the formula —C(R$^{71}$)(R$^{72}$)(R$^{73}$) can be given (in the formula, each of R$^{71}$ to R$^{73}$ independently represents a linear alkyl group of 1 to 5 carbon atoms). The group represented by the formula —C(R$^{71}$)(R$^{72}$)(R$^{73}$) preferably has 4 to 8 carbon atoms, and specific examples include a tert-butyl group, a 2-methyl-2-butyl group, a 2-methyl-2-pentyl group and a 3-methyl-3-pentyl group. Among these, a tert-butyl group is particularly desirable.

The term "aliphatic cyclic group" refers to a monocyclic group or polycyclic group that has no aromaticity.

The "aliphatic cyclic group" within the structural unit (a1) may or may not have a substituent. Examples of substituents include lower alkyl groups of 1 to 5 carbon atoms, lower alkoxy groups of 1 to 5 carbon atoms, fluorine atom, fluorinated lower alkyl groups of 1 to 5 carbon atoms, and oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated. Furthermore, the "aliphatic cyclic group" is preferably a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated lower alkyl group, may be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane. Further, these groups in which one or more hydrogen atoms have been removed from a monocycloalkane and groups in which one or more hydrogen atoms have been removed from a polycycloalkane may have part of the carbon atoms constituting the ring replaced with an ethereal oxygen atom (—O—).

Examples of aliphatic cyclic group-containing acid dissociable, dissolution inhibiting groups include (i) a group which has a tertiary carbon atom on the ring structure of a monovalent aliphatic cyclic group; and (ii) a group which has a branched alkylene group containing a tertiary carbon atom, and a monovalent aliphatic cyclic group to which the tertiary carbon atom is bonded.

Specific examples of (i) a group which has a tertiary carbon atom on the ring structure of a monovalent aliphatic cyclic group include groups represented by general formulas (1-1) to (1-9) shown below.

Specific examples of (ii) a group which has a branched alkylene group containing a tertiary carbon atom, and a monovalent aliphatic cyclic group to which the tertiary carbon atom is bonded include groups represented by general formulas (2-1) to (2-6) shown below.

[Chemical Formula 4]

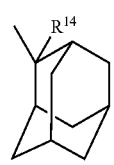

(1-1)

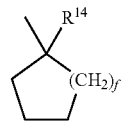

(1-2)

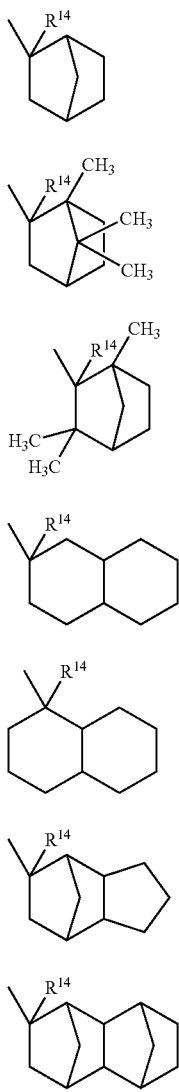

In the formulas above, $R^{14}$ represents an alkyl group; and f represents an integer of 0 to 8.

[Chemical Formula 5]

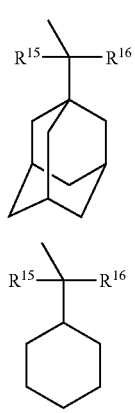

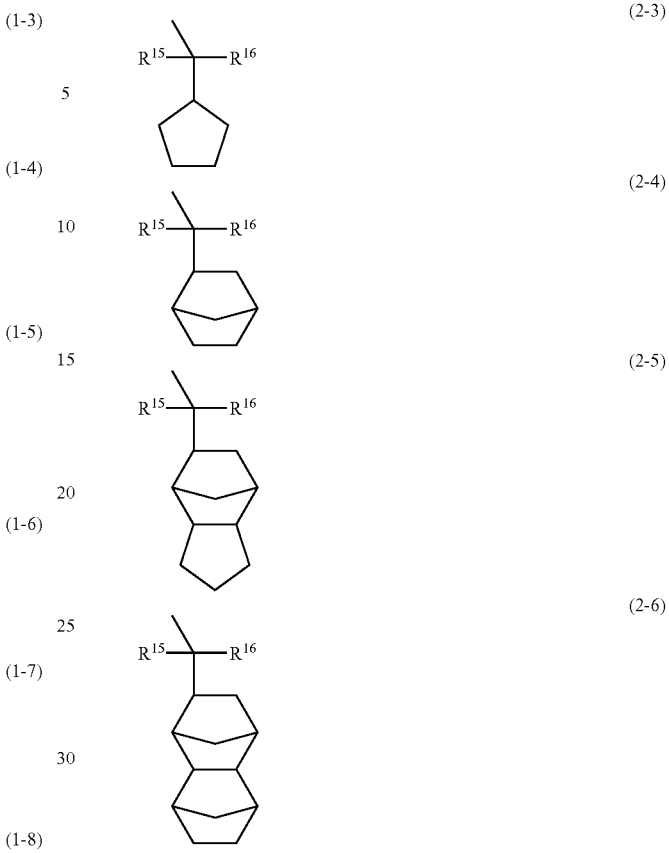

In the formulas above, each of $R^{15}$ and $R^{16}$ independently represents an alkyl group.

As the alkyl group for $R^{14}$, a linear or branched alkyl group is preferable.

The linear alkyl group preferably has 1 to 5 carbon atoms, more preferably 1 to 4, and still more preferably 1 or 2. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 10 carbon atoms, and more preferably 3 to 5. Specific examples of such branched alkyl groups include an isopropyl group, an isobutyl group, a tert-butyl group, an isopentyl group and a neopentyl group, and an isopropyl group is particularly desirable.

f is preferably an integer of 0 to 3, more preferably 1 to 3, and still more preferably 1 or 2.

As the alkyl group for $R^{15}$ and $R^{16}$, the same alkyl groups as those for $R^{14}$ can be used.

In formulas (1-1) to (1-9) and (2-1) to (2-6), part of the carbon atoms constituting the ring may be replaced with an ethereal oxygen atom (—O—).

Further, in formulas (1-1) to (1-9) and (2-1) to (2-6), one or more of the hydrogen atoms bonded to the carbon atoms constituting the ring may be substituted with a substituent. Examples of substituents include a lower alkyl group, a fluorine atom and a fluorinated alkyl group.

An "acetal-type acid dissociable, dissolution inhibiting group" generally substitutes a hydrogen atom at the terminal of an alkali-soluble group such as a carboxy group or hydroxyl group, so as to be bonded with an oxygen atom.

When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 6]

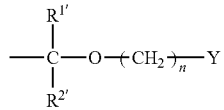
(p1)

In the formula, $R^{1'}$ and $R^{2'}$ each independently represent a hydrogen atom or a lower alkyl group; n represents an integer of 0 to 3; and Y represents a lower alkyl group or an aliphatic cyclic group.

In general formula (p1) above, n is preferably an integer of 0 to 2, more preferably 0 or 1, and most preferably 0.

As the lower alkyl group for $R^{1'}$ and $R^{2'}$, the same lower alkyl groups as those described above for R can be used, although a methyl group or ethyl group is preferable, and a methyl group is particularly desirable.

In the present invention, it is preferable that at least one of $R^{1'}$ and $R^{2'}$ be a hydrogen atom. That is, it is preferable that the acid dissociable, dissolution inhibiting group (p1) is a group represented by general formula (p1-1) shown below.

[Chemical Formula 7]

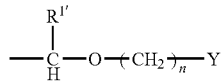
(p1-1)

In the formula, $R^{1'}$, n and Y are the same as defined above.

As the lower alkyl group for Y, the same as the lower alkyl groups for R above can be used.

As the aliphatic cyclic group for Y, any of the aliphatic monocyclic/polycyclic groups which have been proposed for conventional ArF resists and the like can be appropriately selected for use. For example, the same groups described above in connection with the "aliphatic cyclic group" can be used.

Further, as the acetal-type, acid dissociable, dissolution inhibiting group, groups represented by general formula (p2) shown below can also be used.

[Chemical Formula 8]

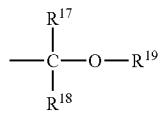
(p2)

In the formula, $R^{17}$ and $R^{18}$ each independently represent a linear or branched alkyl group or a hydrogen atom; and $R^{19}$ represents a linear, branched or cyclic alkyl group; or $R^{17}$ and $R^{19}$ each independently represents a linear or branched alkylene group, and the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane. Among these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4- to 7-membered ring, and more preferably a 4- to 6-membered ring. Specific examples of the cyclic group include tetrahydropyranyl group and tetrahydrofuranyl group.

Specific examples of acetal-type acid dissociable, dissolution inhibiting groups include groups represented by formulas (p3-1) to (p3-12) shown below.

[Chemical Formula 9]

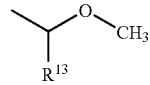
(p3-1)

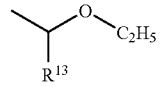
(p3-2)

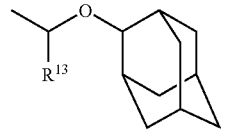
(p3-3)

(p3-4) 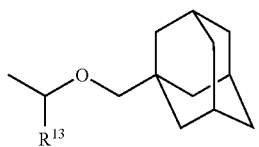

(p3-5) 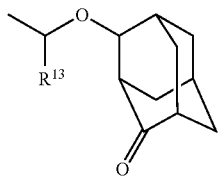

(p3-6) 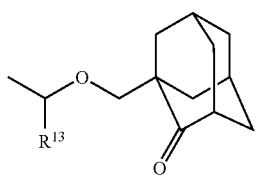

(p3-7) 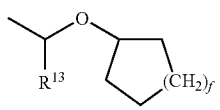

(p3-8) 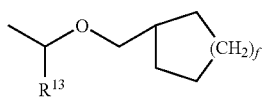

(p3-9) 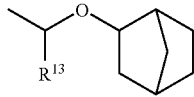

(p3-10) 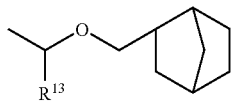

(p3-11) 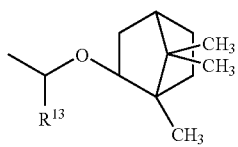

(p3-12) 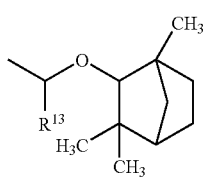

In the formulas above, $R^{13}$ represents a hydrogen atom or a methyl group; and f is the same as defined above.

Specific examples of the structural unit (a1) include a structural unit represented by general formula (a1-0-1) shown below and a structural unit represented by general formula (a1-0-2) shown below.

[Chemical Formula 10]

(a1-0-1) 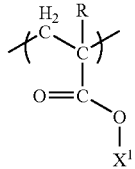

(a1-0-2) 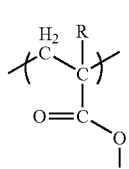

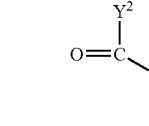

In the formulas, R represents a hydrogen atom, a lower alkyl group or a halogenated lower alkyl group; $X^1$ represents an acid dissociable, dissolution inhibiting group; $Y^2$ represents a divalent linking group; and $X^2$ represents an acid dissociable, dissolution inhibiting group.

In general formula (a1-0-1) shown above, lower alkyl group and halogenated lower alkyl group for R are the same as the lower alkyl group and halogenated lower alkyl group which can be bonded to the α-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (a1-0-2), R is the same as defined above. $X^2$ is the same as defined for $X^1$ in general formula (a1-0-1).

As the divalent linking group for $Y^2$, an alkylene group, a divalent aliphatic cyclic group or a divalent linking group containing a hetero atom can be mentioned.

As the aliphatic cyclic group, the same as those used above in connection with the explanation of "aliphatic cyclic group" can be used, except that two hydrogen atoms have been removed therefrom.

When $Y^2$ represents an alkylene group, it preferably has 1 to 10 carbon atoms, more preferably 1 to 6, still more preferably 1 to 4, and most preferably 1 to 3.

When $Y^2$ represents a divalent aliphatic cyclic group, it is particularly desirable that the divalent aliphatic cyclic group be a group in which two or more hydrogen atoms have been removed from cyclopentane, cyclohexane, norbornane, isobornane, adamantane, tricyclodecane or tetracyclododecane.

When $Y^2$ represents a divalent linking group containing a hetero atom, examples thereof include —O—, —C(=O)—O—, —C(=O)—, —C(=O)—NH—, —NH— (H may be substituted with a substituent such as an alkyl group or an acyl group), —S—, —S(=O)$_2$—, —S(=O)$_2$—O—, and "-A-O—B— (wherein 0 is an oxygen atom, and each of A and B independently represents a divalent hydrocarbon group which may have a substituent)".

When $Y^2$ represents a divalent linking group —NH— and the H in the formula is replaced with a substituent such as an alkyl group or an acyl group, the substituent preferably has 1 to 10 carbon atoms, more preferably 1 to 8 carbon atoms, and most preferably 1 to 5 carbon atoms.

When $Y^2$ is "A-O—B", each of A and B independently represents a divalent hydrocarbon group which may have a substituent.

A hydrocarbon "has a substituent" means that part or all of the hydrogen atoms within the hydrocarbon group is substituted with groups or atoms other than hydrogen atom.

The hydrocarbon group for A may be either an aliphatic hydrocarbon group, or an aromatic hydrocarbon group. An "aliphatic hydrocarbon group" refers to a hydrocarbon group that has no aromaticity.

The aliphatic hydrocarbon group for A may be either saturated or unsaturated. In general, the aliphatic hydrocarbon group is preferably saturated.

As specific examples of the aliphatic hydrocarbon group for A, a linear or branched aliphatic hydrocarbon group, and an aliphatic hydrocarbon group having a ring in the structure thereof can be given.

The linear or branched aliphatic hydrocarbon group preferably has 1 to 10 carbon atoms, more preferably 1 to 8, still more preferably 2 to 5, and most preferably 2.

As a linear aliphatic hydrocarbon group, a linear alkylene group is preferable, and specific examples include a methylene group, an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, a branched alkylene group is preferable, and specific examples include alkylalkylene groups, e.g., alkylmethylene groups such as —CH($CH_3$)—, —CH($CH_2CH_3$)—, —C($CH_3)_2$—, —C($CH_3$)($CH_2CH_3$)—, —C($CH_3$)($CH_2CH_2CH_3$)— and —C($CH_2CH_3)_2$—; alkylethylene groups such as —CH($CH_3$)$CH_2$—, —CH($CH_3$)CH($CH_3$)—, —C($CH_3)_2CH_2$— and —CH($CH_2CH_3$)$CH_2$—; alkyltrimethylene groups such as —CH($CH_3$)$CH_2CH_2$— and —$CH_2$CH($CH_3$)$CH_2$—; and alkyltetramethylene groups such as —CH($CH_3$)$CH_2CH_2CH_2$— and —$CH_2$CH($CH_3$)$CH_2CH_2$—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of the substituent include a fluorine atom, a fluorinated lower alkyl group of 1 to 5 carbon atoms, and an oxygen atom (=O).

As examples of the hydrocarbon group containing a ring, a cyclic aliphatic hydrocarbon group (a group in which two hydrogen atoms have been removed from an aliphatic hydrocarbon ring), and a group in which the cyclic aliphatic hydrocarbon group is bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane.

As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of the substituent include a lower alkyl group of 1 to 5 carbon atoms, a fluorine atom, a fluorinated lower alkyl group of 1 to 5 carbon atoms, and an oxygen atom (=O).

As A, a linear aliphatic hydrocarbon group is preferable, more preferably a linear alkylene group, still more preferably a linear alkylene group of 2 to 5 carbon atoms, and most preferably an ethylene group.

As the hydrocarbon group for B, the same divalent hydrocarbon groups as those described above for A can be used.

As B, a linear or branched aliphatic hydrocarbon group is preferable, and a methylene group or an alkylmethylene group is particularly desirable.

The alkyl group within the alkyl methylene group is preferably a linear alkyl group of 1 to 5 carbon atoms, more preferably a linear alkyl group of 1 to 3 carbon atoms, and most preferably a methyl group.

As $Y^2$, the aforementioned alkylene group, a divalent aliphatic cyclic group or a divalent linking group containing a hetero atom is preferable. Among these, a divalent linking group containing a hetero atom is preferable, and a linear group containing an oxygen atom as a heteroatom, e.g., a group containing an ester bond is particularly desirable.

More specifically, a group represented by the aforementioned formula -A-O—B— or -A-C(=O)—O—B— is preferable, and a group represented by the formula —$(CH_2)_x$—C(=O)—O—$(CH_2)_y$— is particularly desirable.

x represents an integer of 1 to 5, preferably 1 or 2, and most preferably 1.

y represents an integer of 1 to 5, preferably 1 or 2, and most preferably 1.

Specific examples of the structural unit (a1) include structural units represented by general formulas (a1-1) to (a1-4) shown below.

[Chemical Formula 11]

(a1-1)

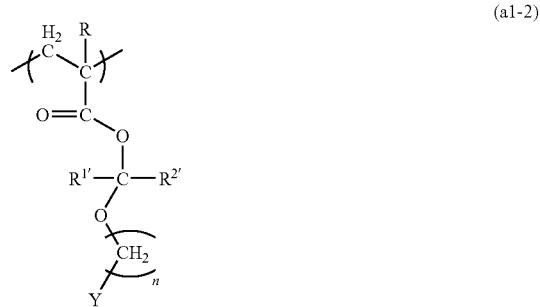

(a1-2)

-continued (a1-3)
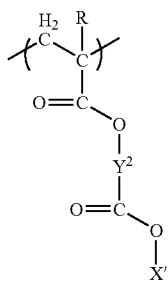

(a1-4)
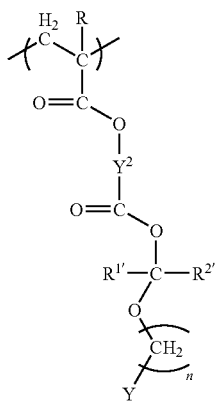

In the formulas, X' represents a tertiary alkyl ester-type acid dissociable, dissolution inhibiting group; Y represents a lower alkyl group of 1 to 5 carbon atoms or an aliphatic cyclic group; n represents an integer of 0 to 3; $Y^2$ represents a divalent linking group; R is the same as defined above; and each of $R^{1\prime}$ and $R^{2\prime}$ independently represents a hydrogen atom or a lower alkyl group of 1 to 5 carbon atoms.

Examples of the tertiary alkyl ester-type acid dissociable, dissolution inhibiting group for X' include the same tertiary alkyl ester-type acid dissociable, dissolution inhibiting groups as those described above for $X^1$.

As $R^{1\prime}$, $R^{2\prime}$, n and Y are respectively the same as defined for $R^{1\prime}$, $R^{2\prime}$, n and Y in general formula (p1) described above in connection with the "acetal-type acid dissociable, dissolution inhibiting group".

As examples of $Y^2$, the same groups as those described above for $Y^2$ in general formula (a1-0-2) can be given.

Specific examples of structural units represented by general formula (a1-1) to (a1-4) are shown below.

In the formulas shown below, $R^\alpha$ represents a hydrogen atom, a methyl group or a trifluoromethyl group.

[Chemical Formula 12]

(a1-1-1)
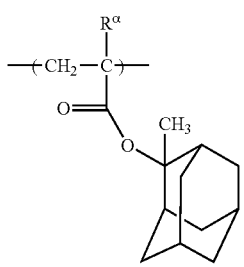

-continued (a1-1-2)
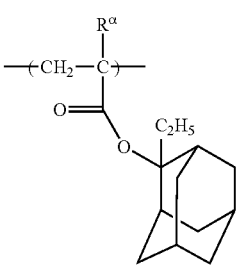

(a1-1-3)
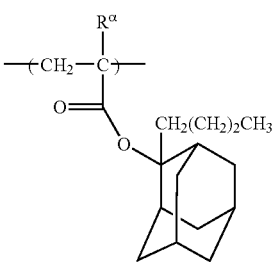

(a1-1-4)
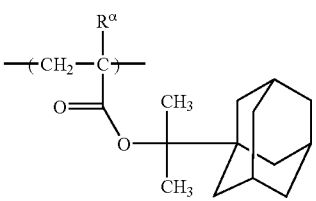

(a1-1-5)
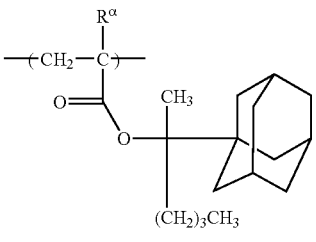

(a1-1-6)
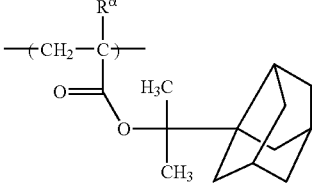

(a1-1-7)
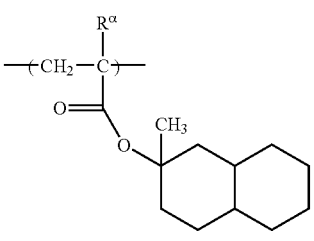

(a1-1-8)
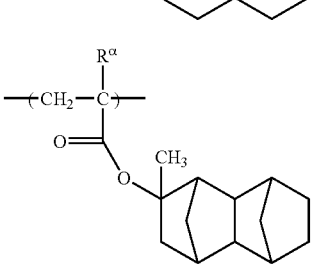

(a1-1-9)
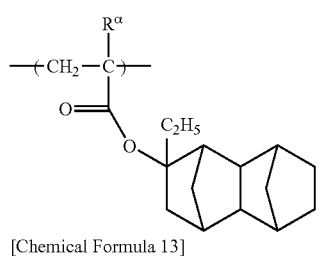
[Chemical Formula 13]
(a1-1-10)
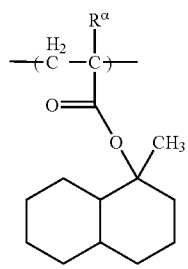
(a1-1-11)
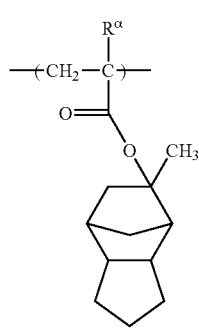
(a1-1-12)
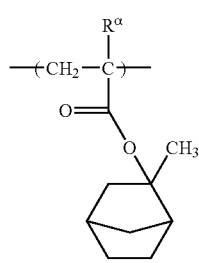
(a1-1-13)
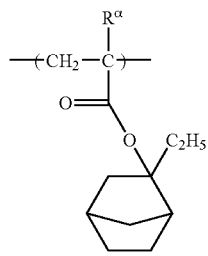
(a1-1-14)
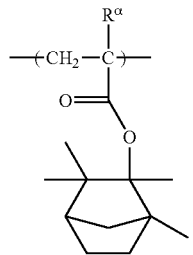
(a1-1-15)
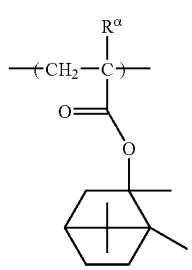
(a1-1-16)
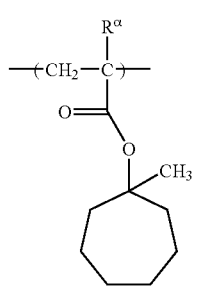
(a1-1-17)
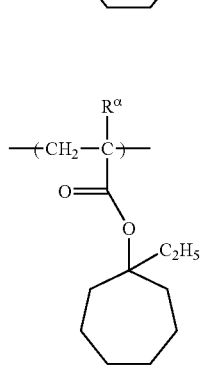
(a1-1-18)
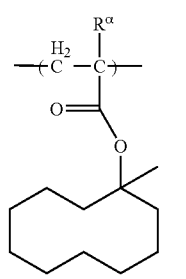
(a1-1-19)
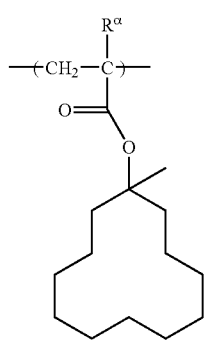

(a1-1-20) 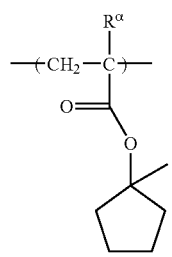
(a1-1-21) 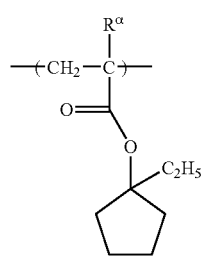
[Chemical Formula 14]
(a1-1-22) 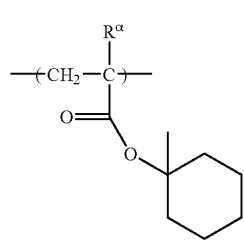
(a1-1-23) 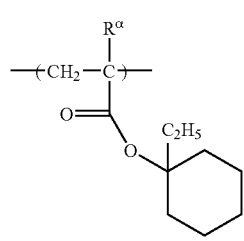
(a1-1-24) 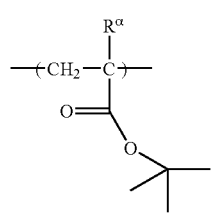
(a1-1-25) 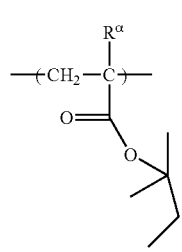
(a1-1-26) 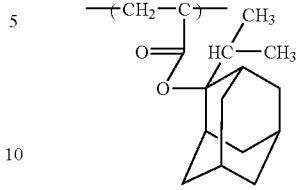
(a1-1-27) 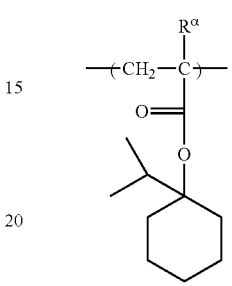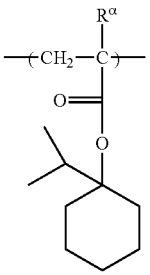
(a1-1-28) 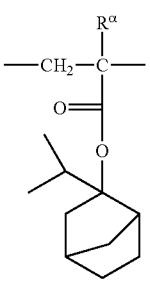
(a1-1-29) 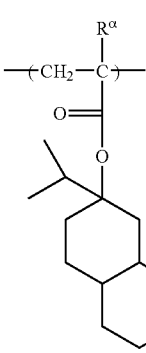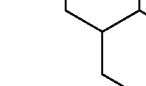
(a1-1-30) 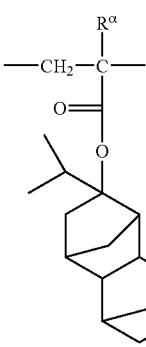

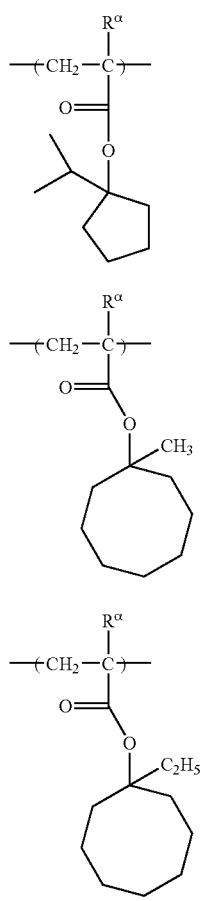
(a1-1-31)
(a1-1-32)
(a1-1-33)
[Chemical Formula 15]
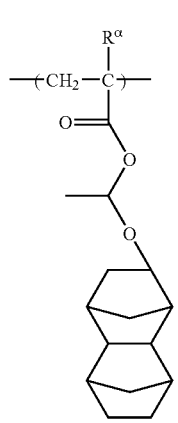
(a1-2-1)
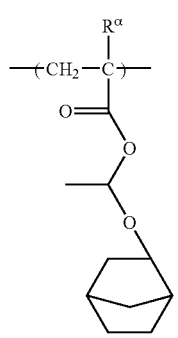
(a1-2-2)
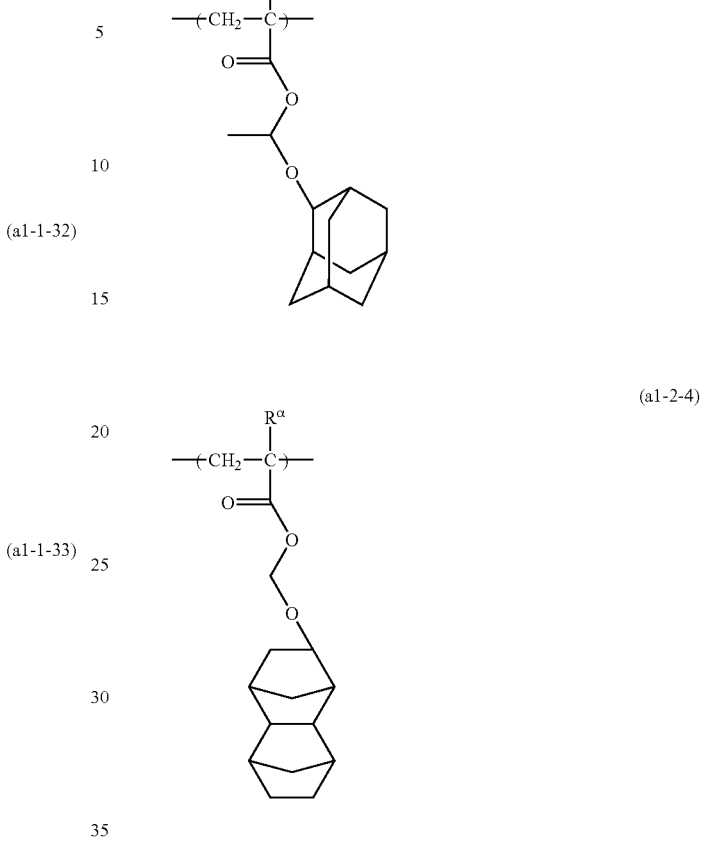
(a1-2-3)
(a1-2-4)
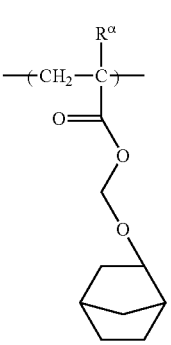
(a1-2-5)
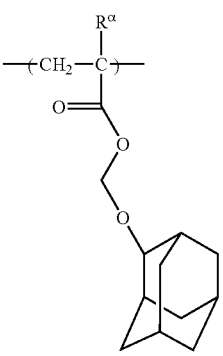
(a1-2-6)

-continued
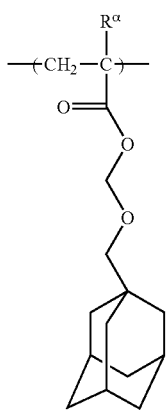 (a1-2-7)
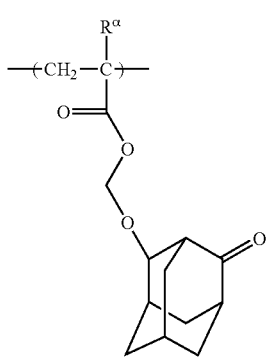 (a1-2-8)
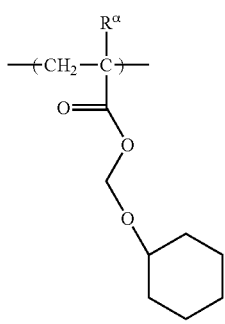 (a1-2-9)
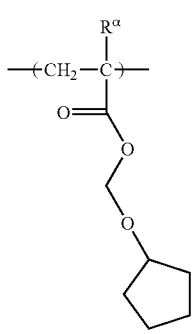 (a1-2-10)
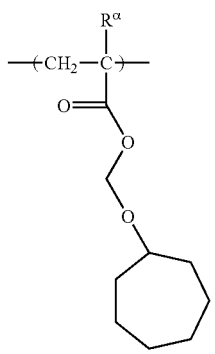 (a1-2-11)
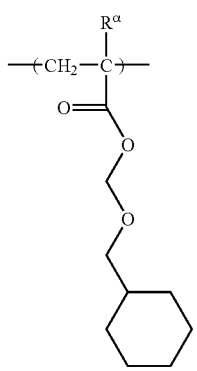 (a1-2-12)
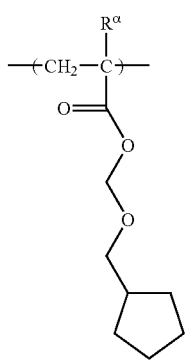 (a1-2-13)
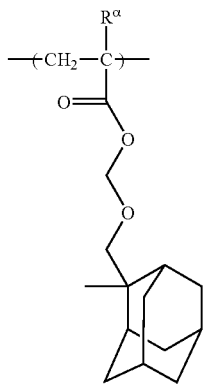 (a1-2-14)

(a1-2-15) 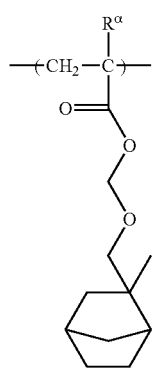
(a1-2-16) 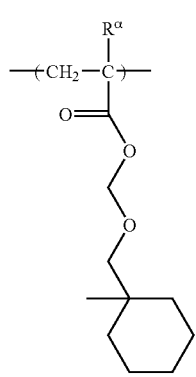
(a1-2-17) 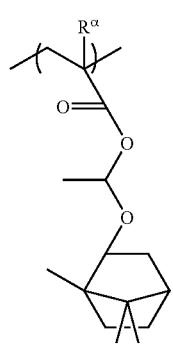
(a1-2-18) 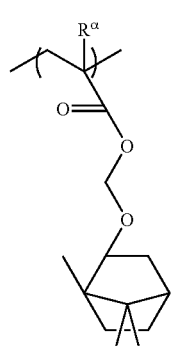
(a1-2-19) 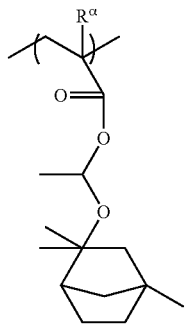
(a1-2-20) 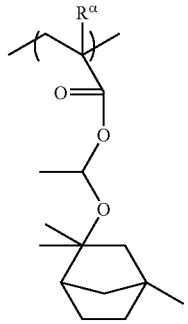
(a1-2-21) 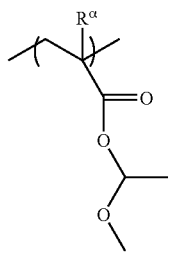
(a1-2-22) 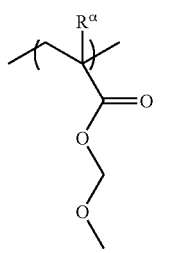
(a1-2-23) 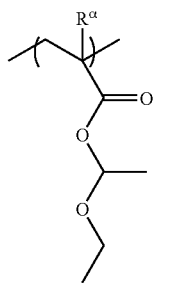

(a1-2-24)
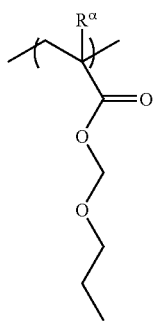
[Chemical Formula 16]
(a1-3-1)
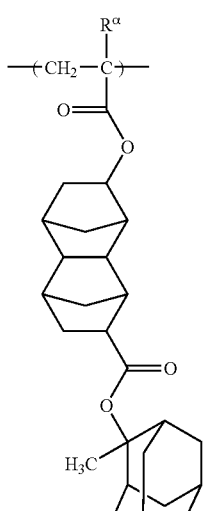
(a1-3-2)
(a1-3-3)
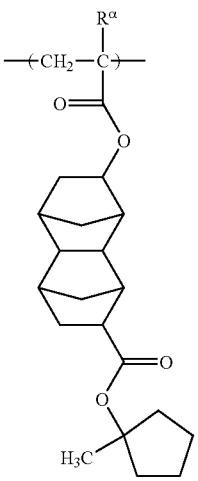
(a1-3-4)
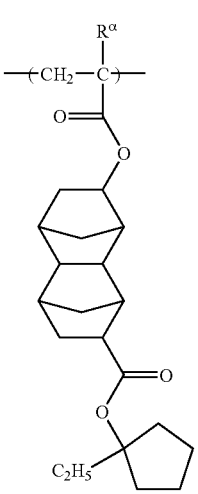
(a1-3-5)
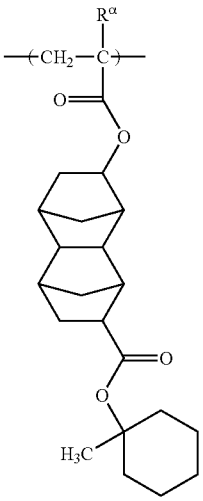

(a1-3-6)
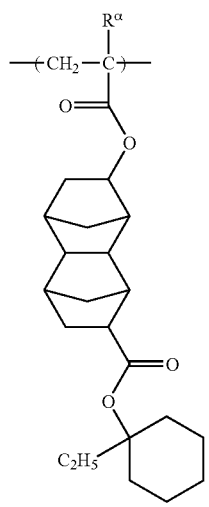
(a1-3-7)
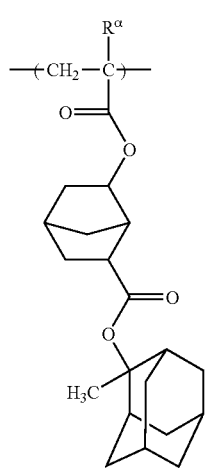
(a1-3-8)
(a1-3-9)
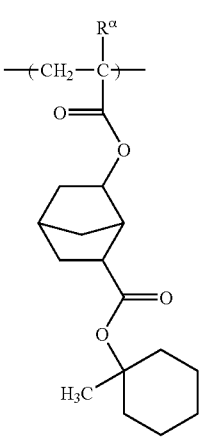
(a1-3-10)
(a1-3-11)
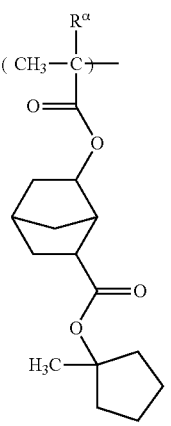

(a1-3-12) 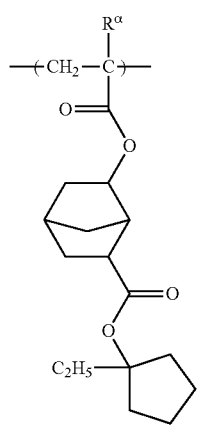
(a1-3-13) 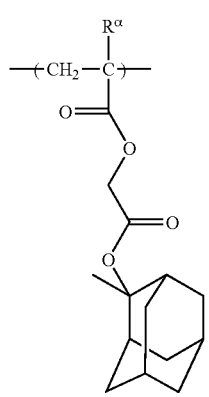
(a1-3-14) 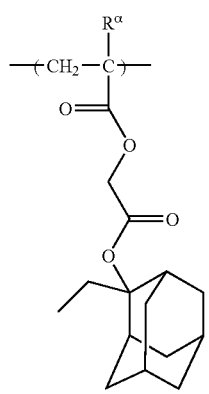
(a1-3-15) 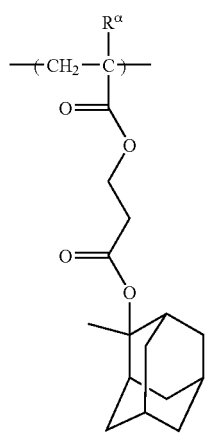
(a1-3-16) 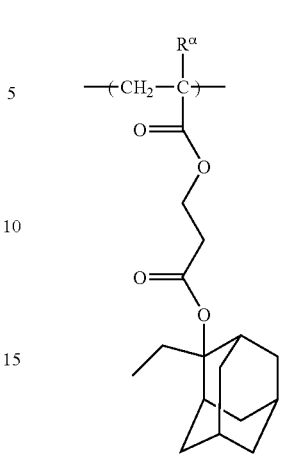
(a1-3-17) 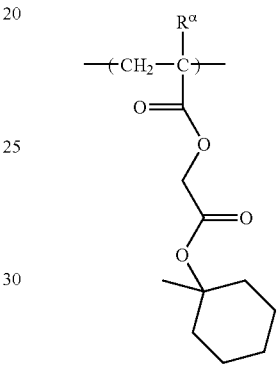
(a1-3-18) 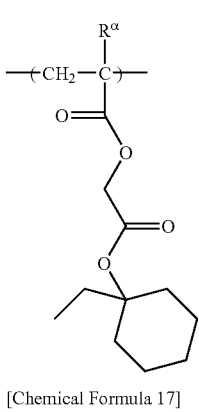
[Chemical Formula 17]
(a1-3-19) 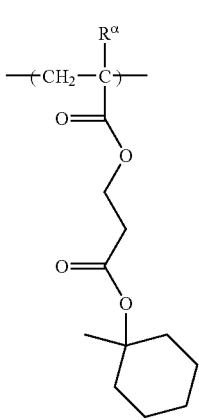

(a1-3-20)
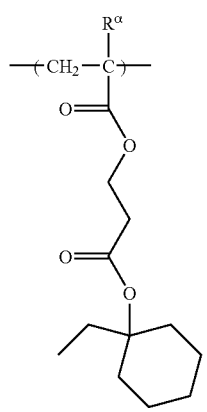
(a1-3-21)
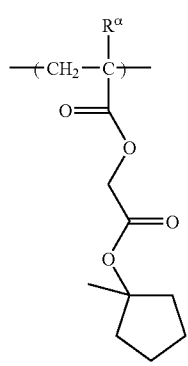
(a1-3-22)
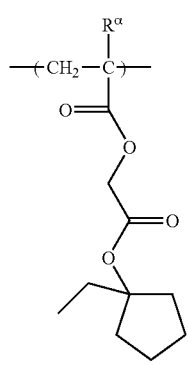
(a1-3-23)
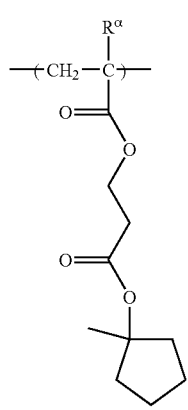
(a1-3-24)
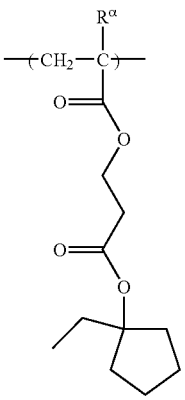
[Chemical Formula 18]
(a1-3-25)
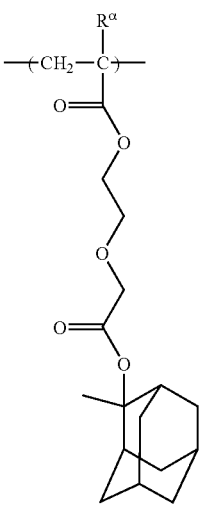
(a1-3-26)
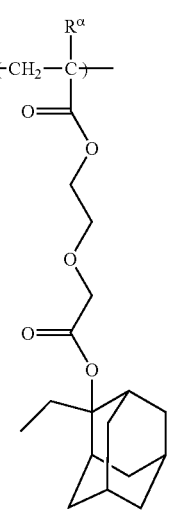

(a1-3-27) 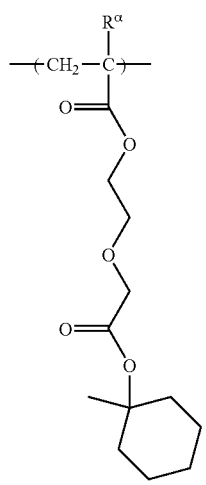
(a1-3-28)
(a1-3-29)
(a1-3-30) 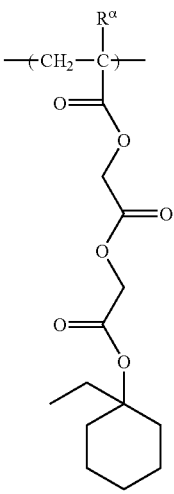
(a1-3-31) 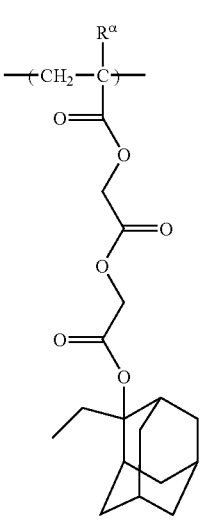
(a1-3-32) 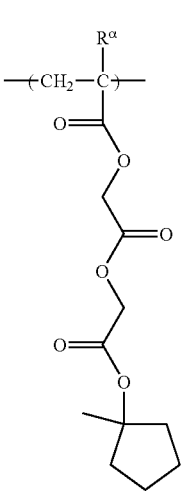
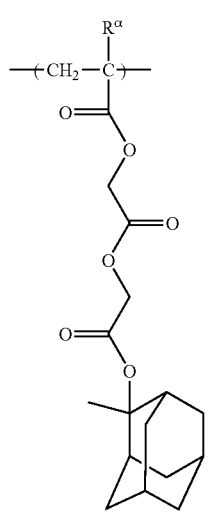

[Chemical Formula 19]
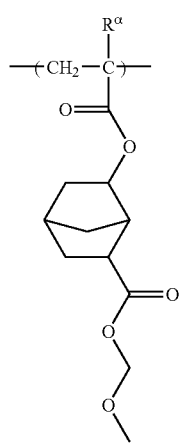 (a1-4-1)
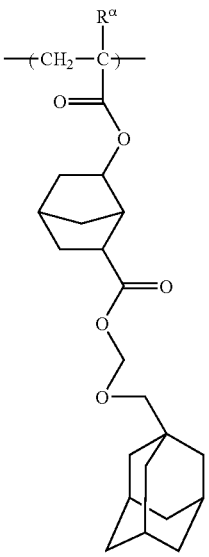 (a1-4-4)
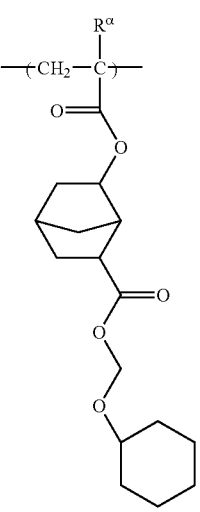 (a1-4-5)
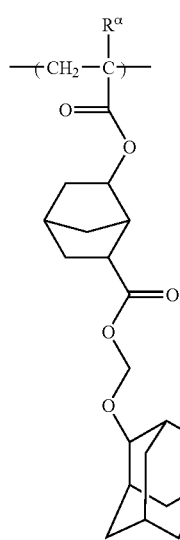 (a1-4-3)
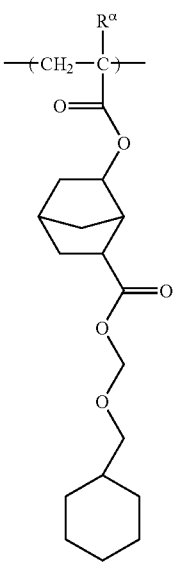 (a1-4-6)

(a1-4-7)
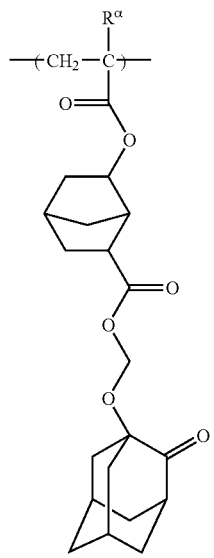
(a1-4-9)
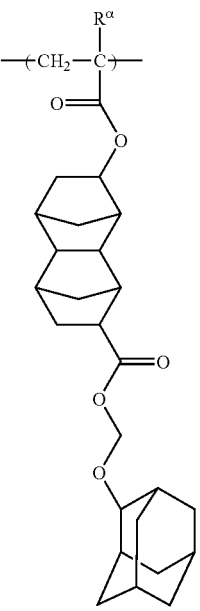
(a1-4-8)
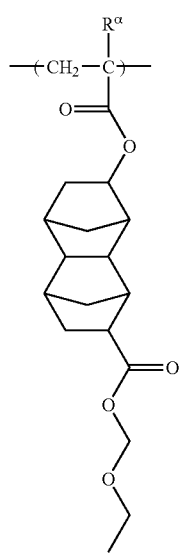
(a1-4-10)
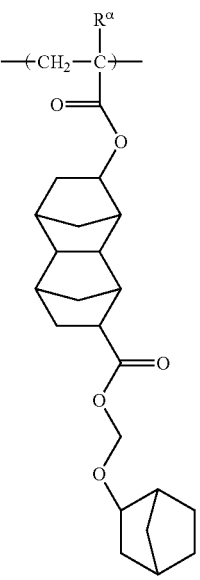

(a1-4-11)
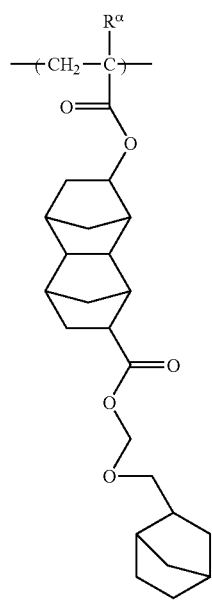
(a1-4-13)
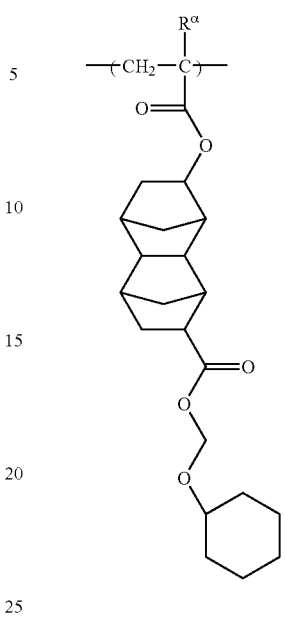
(a1-4-12)
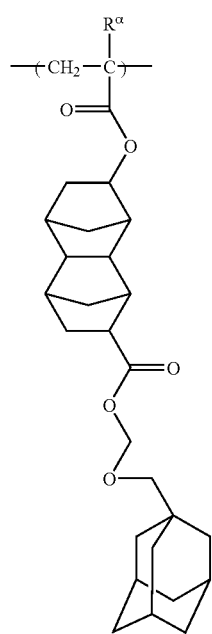
(a1-4-14)
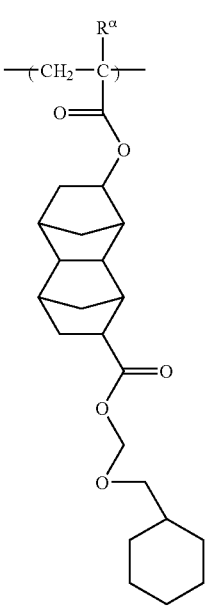

-continued (a1-4-15)

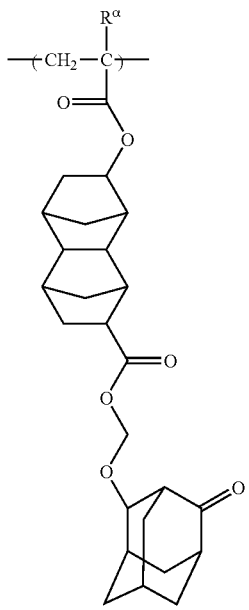

As the structural unit (a1), one type of structural unit may be used, or two or more types may be used in combination.

In the present invention, in terms of achieving excellent lithography properties with respect to resolution, the shape of resist pattern and the like, it is particularly desirable that the structural unit (a1) includes at least one structural unit selected from the group consisting of a structural unit represented by general formula (a1-0-11) shown below, a structural unit represented by general formula (a1-0-12) shown below and a structural unit represented by general formula (a1-0-2) shown below.

[Chemical Formula 20]

(a1-0-11)

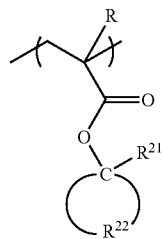

(a1-0-12)

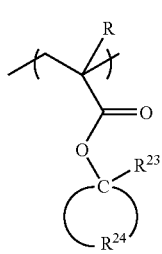

-continued (a1-0-2)

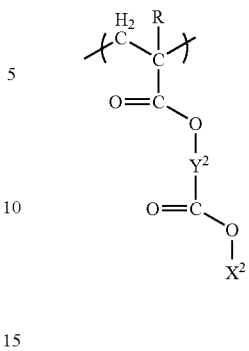

In the formulas, R represents a hydrogen atom, a lower alkyl group or a halogenated lower alkyl group; $R^{21}$ represents an alkyl group; $R^{22}$ represents a group which forms an aliphatic monocyclic group with the carbon atoms to which $R^{22}$ is bonded; $R^{23}$ represents a branched alkyl group; $R^{24}$ represents a group which forms an aliphatic polycyclic group with the carbon atoms to which $R^{24}$ is bonded; $Y^2$ represents a divalent linking group; and $X^2$ represents an acid dissociable, dissolution inhibiting group.

In the formulas, R, $Y^2$ and $X^2$ are the same as defined above.

In general formula (a1-0-11), as the alkyl group for $R^{21}$, the same alkyl groups as those described above for $R^{14}$ in formulas (1-1) to (1-9) can be used, preferably a methyl group or an ethyl group, and most preferably an ethyl group.

As the aliphatic monocyclic group formed by $R^{22}$ and the carbon atoms to which $R^{22}$ is bonded, the same aliphatic cyclic groups as those described above for the aforementioned tertiary alkyl ester-type acid dissociable, dissolution inhibiting group and which are monocyclic can be used. Specific examples include groups in which one or more hydrogen atoms have been removed from a monocycloalkane. The monocycloalkane is preferably a 3- to 11-membered ring, more preferably a 3- to 8-membered ring, still more preferably a 4- to 6-membered ring, and most preferably a 5- or 6-membered ring.

The monocycloalkane may or may not have part of the carbon atoms constituting the ring replaced with an ethereal oxygen atom (—O—).

Further, the monocycloalkane may have a substituent such as a lower alkyl group, a fluorine atom or a fluorinated alkyl group.

As an examples of $R^{22}$ constituting such an aliphatic cyclic group, an alkylene group which may have an ethereal oxygen atom (—O—) interposed between the carbon atoms can be given.

Specific examples of structural units represented by general formula (a1-0-11) include structural units represented by the aforementioned formulas (a1-1-16) to (a1-1-23), (a1-1-32) and (a1-1-33). Among these, a structural unit represented by general formula (a1-1-02) shown below which includes the structural units represented by the aforementioned formulas (a1-1-16), (a1-1-17) and (a1-1-20) to (a1-1-23) is preferable. Further, a structural unit represented by general formula (a1-1-02') shown below is also preferable.

In the formulas shown below, h is preferably 1 or 2, and most preferably 2.

[Chemical Formula 21]

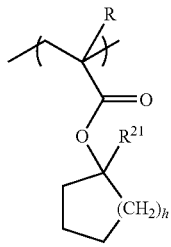

(a1-1-02)

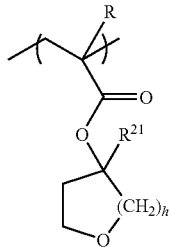

(a1-1-02')

In the formulas, R and $R^{21}$ are the same as defined above; and each h represents an integer of 1 to 3.

In general formula (a1-0-12), as the branched alkyl group for $R^{23}$, the same alkyl groups as those described above for $R^{14}$ which are branched can be used, and an isopropyl group is particularly desirable.

As the aliphatic polycyclic group formed by $R^{24}$ and the carbon atoms to which $R^{24}$ is bonded, the same aliphatic cyclic groups as those described above for the aforementioned tertiary alkyl ester-type acid dissociable, dissolution inhibiting group and which are polycyclic can be used.

Specific examples of structural units represented by general formula (a1-0-12) include structural units represented by the aforementioned formulas (a1-1-26) to (a1-1-31).

Examples of structural units represented by general formula (a1-0-2) include structural units represented by the aforementioned formulas (a1-3) and (a1-4).

As a structural unit represented by general formula (a1-0-2), those in which $Y^2$ is a group represented by the aforementioned formula -A-O—B— or -A-C(=O)—O—B— is particularly desirable.

Preferable examples of such structural units include a structural unit represented by general formula (a1-3-01) shown below, a structural unit represented by general formula (a1-3-02) shown below, and a structural unit represented by general formula (a1-3-03) shown below.

[Chemical Formula 22]

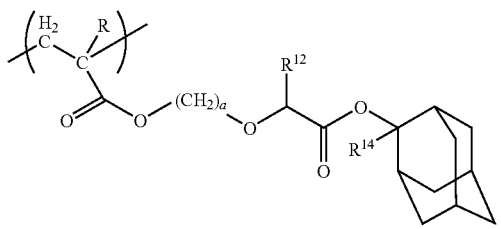

(a1-3-01)

In the formula, R and $R^{14}$ are the same as defined above; $R^{12}$ represents a hydrogen atom or a methyl group; and a represents an integer of 1 to 10.

[Chemical Formula 23]

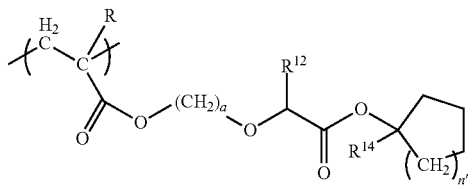

(a1-3-02)

In the formula, R and $R^{14}$ are the same as defined above; $R^{12}$ represents a hydrogen atom or a methyl group; a represents an integer of 1 to 10; and n' represents an integer of 0 to 3.

[Chemical Formula 24]

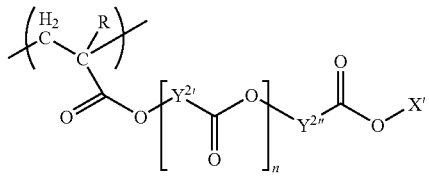

(a1-3-03)

In the formula, R is as defined above; each of $Y^{2\prime}$ and $Y^{2\prime\prime}$ independently represents a divalent linking group; X' represents an acid dissociable, dissolution inhibiting group; and n represents an integer of 1 to 3.

In general formulas (a1-3-01) and (a1-3-02), $R^{12}$ is preferably a hydrogen atom.

a is preferably an integer of 1 to 8, more preferably 1 to 5, and most preferably 1 or 2.

n' is preferably 1 or 2, and most preferably 2.

Specific examples of structural units represented by general formula (a1-3-01) include structural units represented by the aforementioned formulas (a1-3-25) and (a1-3-26).

Specific examples of structural units represented by general formula (a1-3-02) include structural units represented by the aforementioned formulas (a1-3-27) and (a1-3-28).

In general formula (a1-3-03), as the divalent linking group for $Y^{2\prime}$ and $Y^{2\prime\prime}$, the same groups as those described above for $Y^2$ in general formula (a1-3) can be used.

As $Y^{2\prime}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As $Y^{2\prime\prime}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As the acid dissociable, dissolution inhibiting group for X', the same groups as those described above can be used. X' is preferably a tertiary alkyl ester-type acid dissociable, dissolution inhibiting group, more preferably the aforementioned group (i) which has a tertiary carbon atom on the ring structure of a monovalent aliphatic cyclic group. Among the aforementioned groups (i), a group represented by general formula (1-1) above is preferable.

n represents an integer of 0 to 3, preferably an integer of 0 to 2, more preferably 0 or 1, and most preferably 1.

As the structural unit represented by general formula (a1-3-03), a structural unit represented by general formula (a1-3-03-1) or (a1-3-03-2) shown below is preferable.

Among these, a structural unit represented by general formula (a1-3-03-1) is preferable, and a structural unit represented by any one of the aforementioned formulas (a1-3-29) to (a1-3-32) is particularly desirable.

[Chemical Formula 25]

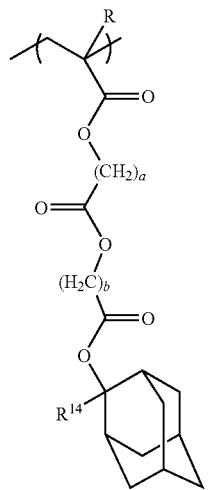

(a1-3-03-1)

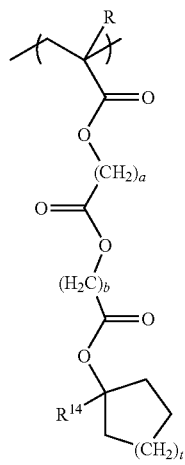

(a1-3-03-2)

In the formulas, R and $R^{14}$ are the same as defined above; a represents an integer of 1 to 10; b represents an integer of 1 to 10; and t represents an integer of 0 to 3.

a is preferably an integer of 1 to 5, and most preferably 1 or 2.

b is preferably an integer of 1 to 5, and most preferably 1 or 2.

t is preferably an integer of 1 to 3, and most preferably 1 or 2.

In the present invention, it is particularly desirable that the component (A1) include at least two types of structural units as the structural unit (a1). By virtue of including two types of structural units as the structural unit (a1), the lithography properties can be further improved.

In such a case, it is preferable that at least one of the at least two structural units is a structural unit selected from the group consisting of a structural unit represented by general formula (a1-0-11), a structural unit represented by general formula (a1-0-12) and a structural unit represented by general formula (a1-0-2).

The structural unit (a1) including at least two types of structural units may consist of structural units selected from the group consisting of a structural unit represented by general formula (a1-0-11), a structural unit represented by general formula (a1-0-12) and a structural unit represented by general formula (a1-0-2). Alternatively, the structural unit (a1) may be a combination of at least one structural unit selected from the aforementioned group and a structural unit which does not fall under the category of the aforementioned group.

As examples of the structural unit which can be used in combination with at least one structural unit selected from the group consisting of a structural unit represented by general formula (a1-0-11), a structural unit represented by general formula (a1-0-12) and a structural unit represented by general formula (a1-0-2) and does not fall under the category of the aforementioned group, a structural unit represented by general formula (a1-1-01) shown below which includes the structural units represented by the aforementioned (a1-1-1), (a1-1-2), (a1-1-7) to (a1-1-15) described above as specific examples of structural units represented by general formula (a1-1), structural units represented by general formula (a1-2) and structural units represented by general formula (a1-4) can be given.

As a structural unit represented by general formula (a1-1-01), a structural unit represented by general formula (a1-1-101) shown below which includes the aforementioned formulas (a1-1-1) and (a1-1-2) is particularly desirable.

[Chemical Formula 26]

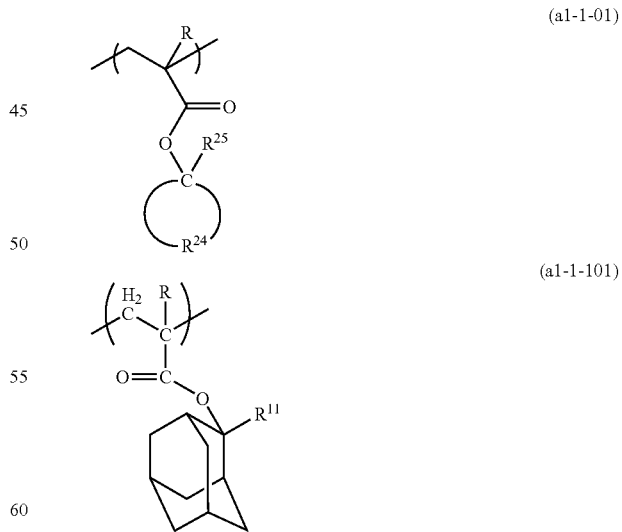

In the formulas, R is the same as defined above; each of $R^{25}$ and $R^{11}$ independently represents a linear alkyl group of 1 to 5 carbon atoms; and $R^{24}$ is the same as defined above.

In the component (A1), the amount of the structural unit (a1) based on the combined total of all structural units constituting the component (A1) is preferably 10 to 80 mol %, more preferably 20 to 70 mol %, and still more preferably 25 to 50 mol %. When the amount of the structural unit (a1) is at least as large as the lower limit of the above-mentioned range, a pattern can be easily formed using a resist composition prepared from the component (A1). On the other hand, when the amount of the structural unit (a1) is no more than the upper limit of the above-mentioned range, a good balance can be achieved with the other structural units.

(Structural Unit (a2))

The structural unit (a2) is a structural unit derived from an acrylate ester containing a lactone-containing cyclic group.

The term "lactone-containing cyclic group" refers to a cyclic group including one ring containing a —O—C(O)— structure (lactone ring). The term "lactone ring" refers to a single ring containing a —O—C(O)— structure, and this ring is counted as the first ring.

A lactone-containing cyclic group in which the only ring structure is the lactone ring is referred to as a monocyclic group, and groups containing other ring structures are described as polycyclic groups regardless of the structure of the other rings.

When the component (A1) is used for forming a resist film, the lactone-containing cyclic group of the structural unit (a2) is effective in improving the adhesion between the resist film and the substrate, and increasing the compatibility with the developing solution containing water.

As the structural unit (a2), there is no particular limitation, and an arbitrary structural unit may be used.

Specific examples of lactone-containing monocyclic groups include a group in which one hydrogen atom has been removed from a 4- to 6-membered lactone ring, such as a group in which one hydrogen atom has been removed from β-propionolactone, a group in which one hydrogen atom has been removed from γ-butyrolactone, and a group in which one hydrogen atom has been removed from δ-valerolactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

[Chemical Formula 27]

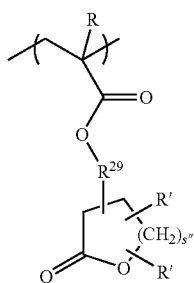
(a2-1)

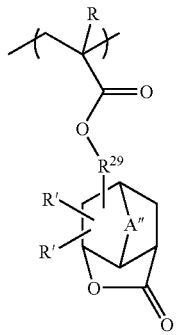
(a2-2)

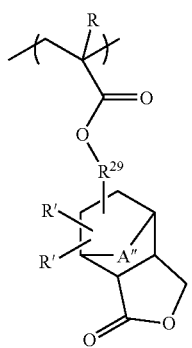
(a2-3)

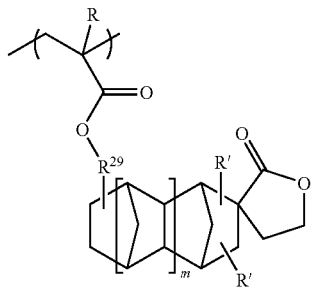
(a2-4)

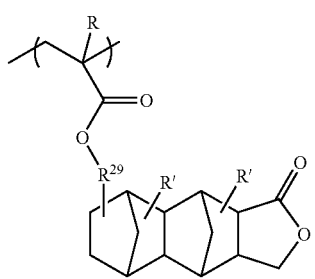
(a2-5)

In the formulas, R represents a hydrogen atom, a lower alkyl group or a halogenated lower alkyl group; each R' independently represents a hydrogen atom, an alkyl group of 1 to 5 carbon atoms, an alkoxy group of 1 to 5 carbon atoms or —COOR", wherein R" represents a hydrogen atom or an alkyl group; $R^{29}$ represents a single bond or a divalent linking group; s" represents an integer of 0 to 2; A" represents an oxygen atom, a sulfur atom or an alkylene group of 1 to 5 carbon atoms which may contain an oxygen atom or a sulfur atom; and m represents 0 or 1.

In general formulas (a2-1) to (a2-5), R is the same as defined for R in the structural unit (a1).

Examples of the alkyl group of 1 to 5 carbon atoms for R' include a methyl group, an ethyl group, a propyl group, an n-butyl group and a tert-butyl group.

Examples of the alkoxy group of 1 to 5 carbon atoms for R' include a methoxy group, an ethoxy group, an n-propoxy group, an iso-propoxy group, an n-butoxy group and a tert-butoxy group In terms of industrial availability, R' is preferably a hydrogen atom.

When R" is a linear or branched alkyl group, it preferably has 1 to 10 carbon atoms, more preferably 1 to 5 carbon atoms.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

As A", an alkylene group of 1 to 5 carbon atoms or —O— is preferable, more preferably an alkylene group of 1 to 5 carbon atoms, and most preferably a methylene group.

$R^{29}$ represents a single bond or a divalent linking group. Examples of divalent linking groups include the same divalent linking groups as those described above for $Y^2$ in general formula (a1-0-2). Among these, an alkylene group, an ester bond (—C(=O)—O—) or a combination thereof is preferable. The alkylene group as a divalent linking group for $R^{29}$ is preferably a linear or branched alkylene group. Specific examples include the same linear alkylene groups and branched alkylene groups as those described above for the aliphatic cyclic group A in $Y^2$.

s" is preferably 1 or 2.

Specific examples of structural units represented by general formulas (a2-1) to (a2-5) are shown below. In the formulas shown below, $R^{\alpha}$ represents a hydrogen atom, a methyl group or a trifluoromethyl group.

[Chemical Formula 28]

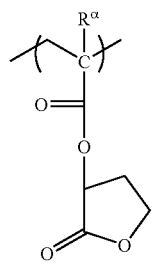
(a2-1-1)

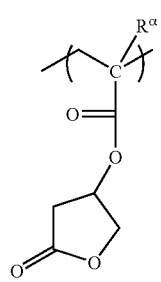
(a2-1-2)

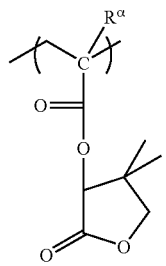
(a2-1-3)

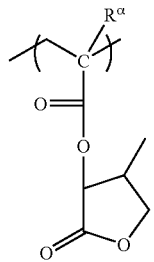
(a2-1-4)

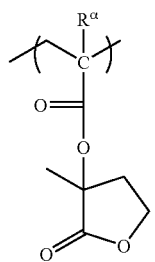
(a2-1-5)

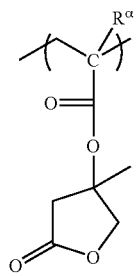
(a2-1-6)

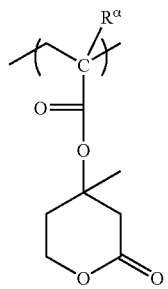
(a2-1-7)

(a2-1-8)
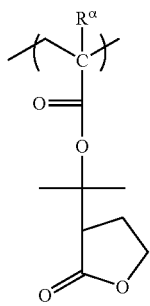
(a2-1-9)
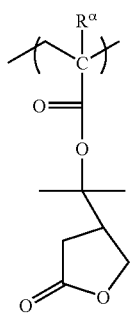
(a2-1-10)
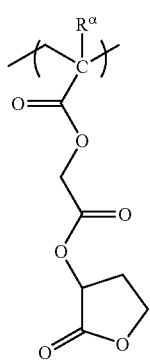
(a2-1-11)
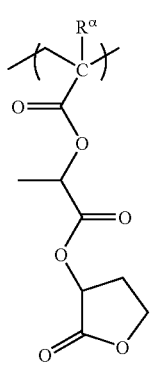
(a2-1-12)
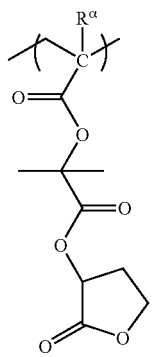
(a2-1-13)
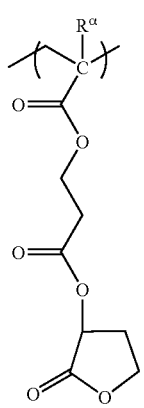
[Chemical Formula 29]
(a2-2-1)
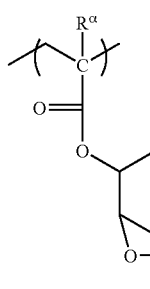
(a2-2-2)
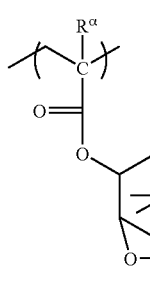

-continued
(a2-2-3)
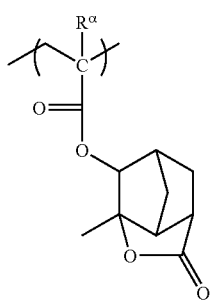
(a2-2-4)
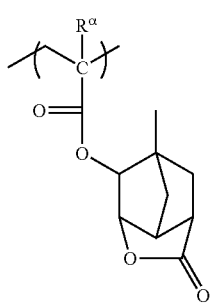
(a2-2-5)
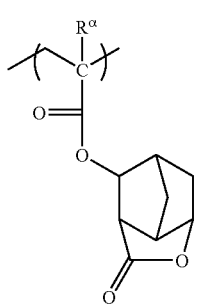
(a2-2-6)
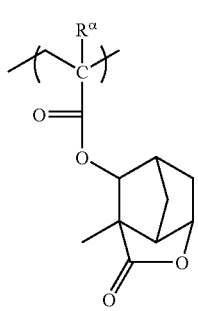
(a2-2-7)
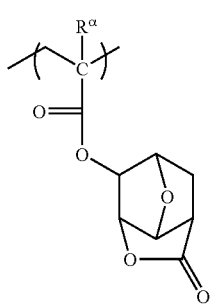
-continued
(a2-2-8)
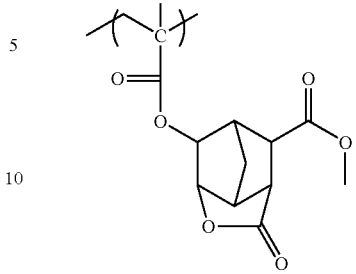
(a2-2-9)
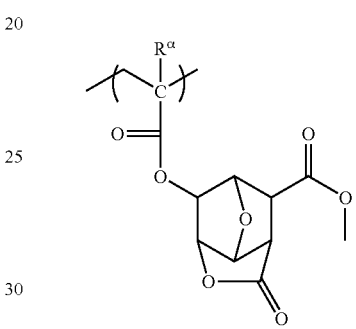
(a2-2-10)
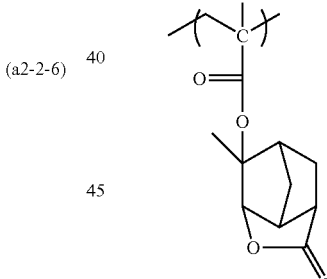
(a2-2-11)
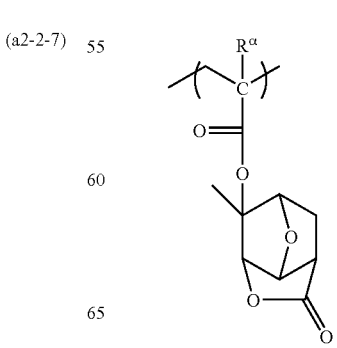

(a2-2-12)
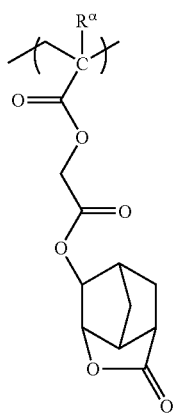
(a2-2-13)
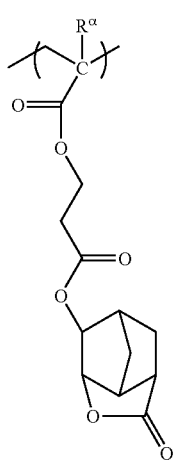
(a2-2-14)
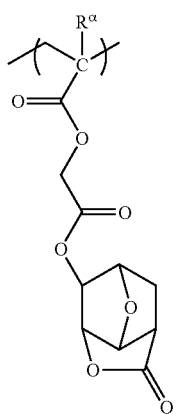
(a2-2-15)
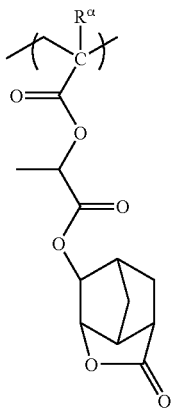
(a2-2-16)
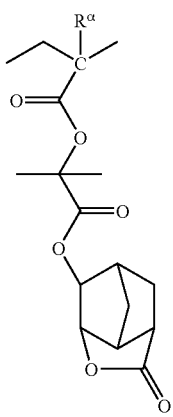
(a2-2-17)
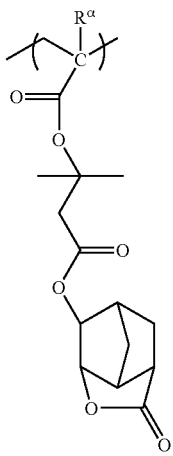
[Chemical Formula 30]
(a2-3-1)
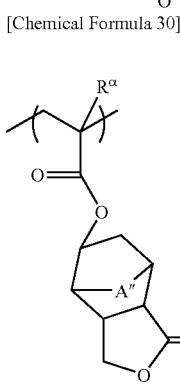

(a2-3-2)
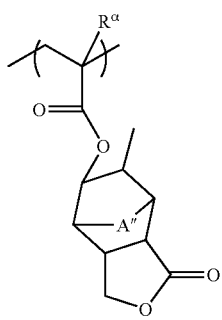
(a2-3-3)
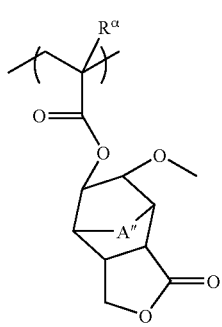
(a2-3-4)
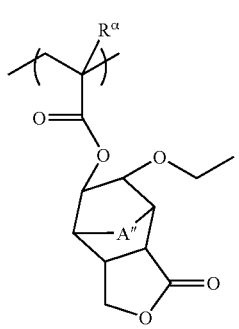
(a2-3-5)
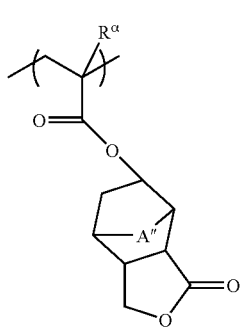
[Chemical Formula 31]
(a2-4-1)
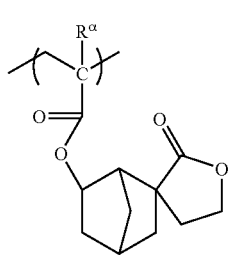
(a2-4-2)
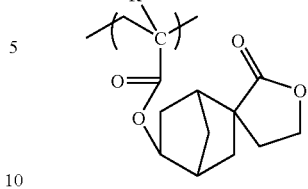
(a2-4-3)
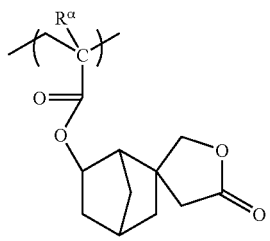
(a2-4-4)
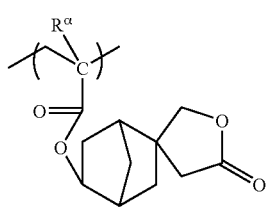
(a2-4-5)
(a2-4-6)
(a2-4-7)
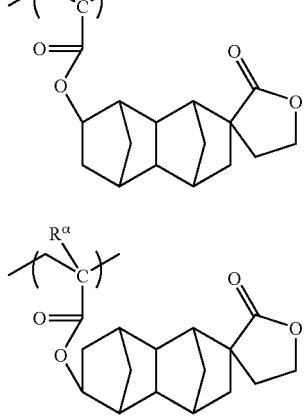
(a2-4-8)
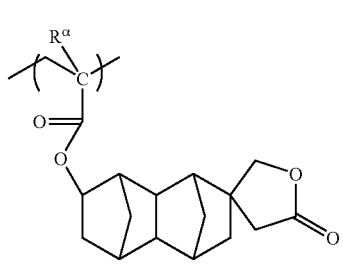
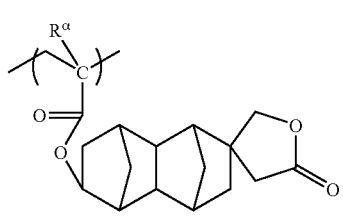

(a2-4-9)
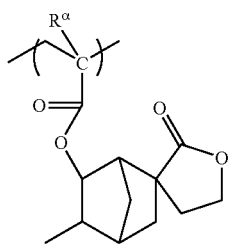
(a2-4-10)
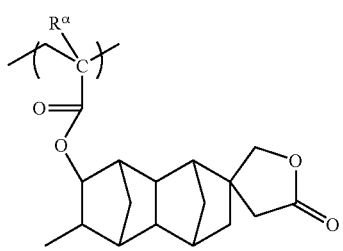
(a2-4-11)
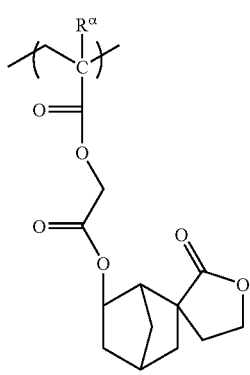
(a2-4-12)
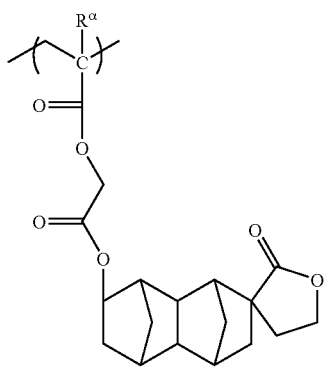
[Chemical Formula 32]
(a2-5-1)
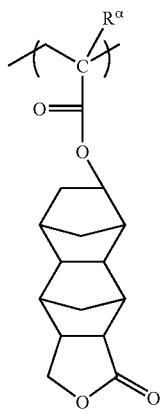
(a2-5-2)
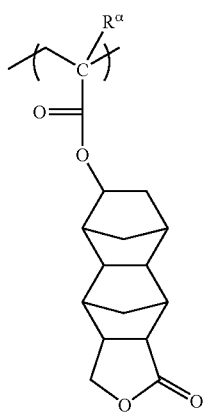
(a2-5-3)
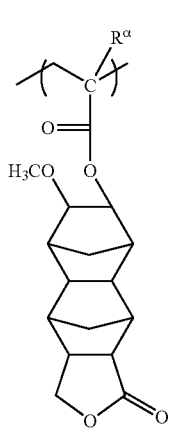

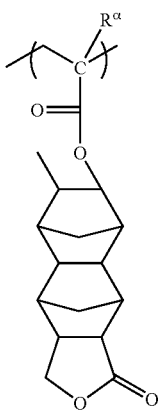
(a2-5-4)

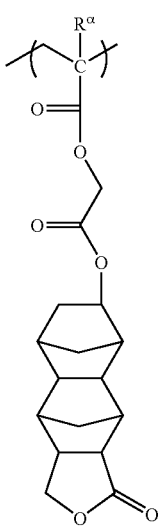
(a2-5-5)

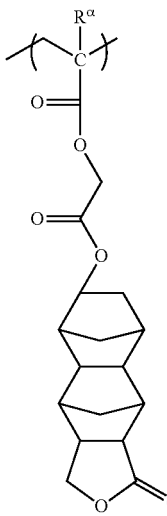
(a2-5-6)

In the component (A1), as the structural unit (a2), one type of structural unit may be used, or two or more types may be used in combination.

In the present invention, it is particularly desirable that the component (A1) contain, as a structural unit (a2), at least one structural unit selected from the group consisting of a structural unit represented by general formula (a2-1) and a structural unit represented by general formula (a2-2).

In terms of improving the adhesion between a substrate and a resist film formed using a resist composition containing the component (A1) and increasing the compatibility with a developing solution, the amount of the structural unit (a2) within the component (A1), based on the combined total of all structural units constituting the component (A1) is preferably 1 to 50 mol %, more preferably 5 to 50 mol %, and still more preferably 10 to 45 mol %.

When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units.

(Structural Unit (a3))

The structural unit (a3) is a structural unit derived from an acrylate ester containing a polar group-containing aliphatic hydrocarbon group.

When the component (A1) includes the structural unit (a3), the hydrophilicity of the component (A) is improved, and hence, the compatibility of the component (A) with the developing solution is improved. As a result, the alkali solubility of the exposed portions improves, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (preferably alkylene groups) of 1 to 10 carbon atoms, and polycyclic aliphatic hydrocarbon groups (polycyclic groups). These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that include an aliphatic polycyclic group that contains a hydroxyl group, cyano group, carboxyl group or a hydroxyalkyl group in which part of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2), (a3-3) and (a3-4) shown below are preferable.

[Chemical Formula 33]

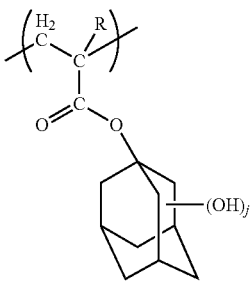 (a3-1)

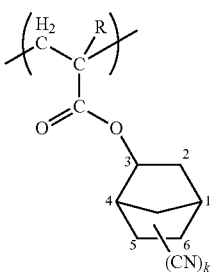 (a3-2)

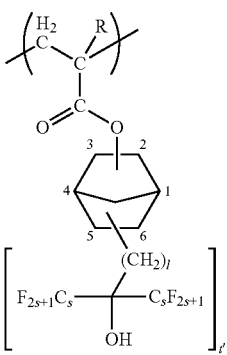 (a3-3)

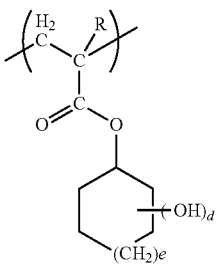 (a3-4)

In the formulas above, R is as defined above; j is an integer of 1 to 3; k is an integer of 1 to 3; t' is an integer of 1 to 3; l is an integer of 1 to 5; s is an integer of 1 to 3; d represents an integer of 1 to 3; and e represents 0 or 1.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, in formula (a3-3), it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

In formula (a3-4), d is preferably 1 or 2, and more preferably 1. Although the bonding position of the hydroxyl group is not particularly limited, when d is 1, the 2nd position is preferable in terms of availability and low cost. When d is 2 or 3, a desired combination of the bonding positions can be used.

As the structural unit (a3), one type of structural unit may be used, or two or more types may be used in combination.

In the component (A1), the amount of the structural unit (a3) based on the combined total of all structural units constituting the component (A1) is preferably 5 to 50 mol %, more preferably 5 to 40 mol %, and still more preferably 5 to 25 mol %. When the amount of the structural unit (a3) is at least as large as the lower limit of the above-mentioned range, the effect of using the structural unit (a3) can be satisfactorily achieved. On the other hand, when the amount of the structural unit (a3) is no more than the upper limit of the above-mentioned range, a good balance can be achieved with the other structural units.

(Other Structural Units)

The component (A1) may also have a structural unit other than the above-mentioned structural units (a1) to (a3), as long as the effects of the present invention are not impaired.

As such a structural unit, any other structural unit which cannot be classified as one of the above structural units (a1) to (a3) can be used without any particular limitation, and any of the multitude of conventional structural units used within resist resins for ArF excimer lasers or KrF excimer lasers (and particularly for ArF excimer lasers) can be used.

Structural Unit (a4)

As such a structural unit, for example, a structural unit derived from an acrylate ester containing a non-acid-dissociable aliphatic polycyclic group (hereafter, referred to as "structural unit (a4)") is preferable. Examples of this polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a-4-1) to (a-4-5) shown below.

[Chemical Formula 34]

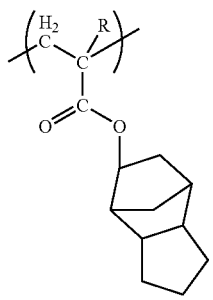 (a4-1)

-continued

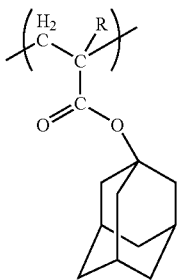
(a4-2)

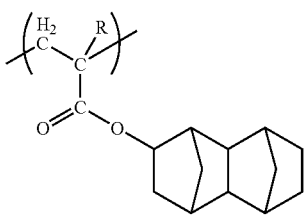
(a4-3)

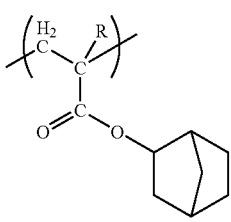
(a4-4)

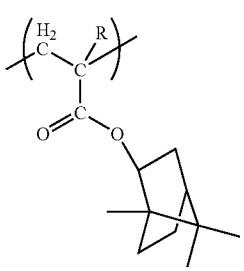
(a4-5)

In the formulas, R is the same as defined above.

When the structural unit (a4) is included in the component (A1), the amount of the structural unit (a4) based on the combined total of all the structural units that constitute the component (A1) is preferably within the range from 1 to 30 mol %, and more preferably from 10 to 20 mol %.

Structural Unit (a0)

Further, as such a structural unit, a structural unit (a0) represented by general formula (a0-1) shown below is also preferable.

[Chemical Formula 35]

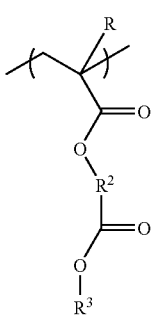
(a0-1)

In formula (a0-1), R represents a hydrogen atom, a lower alkyl group of 1 to 5 carbon atoms or a halogenated lower alkyl group of 1 to 5 carbon atoms; $R^2$ represents a divalent linking group; and $R^3$ represents a cyclic group containing —$SO_2$— within the ring skeleton thereof.

In general formula (a0-1), R represents a hydrogen atom, a lower alkyl group of 1 to 5 carbon atoms or a halogenated lower alkyl group of 1 to 5 carbon atoms.

As the lower alkyl group for R, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group.

The halogenated lower alkyl group for R is a group in which part or all of the hydrogen atoms of the aforementioned lower alkyl group is substituted with halogen atoms. Examples of the halogen atom include a fluorine atom, a chlorine atom, a bromine atom and an iodine atom, and a fluorine atom is particularly desirable.

As R, a hydrogen atom, a lower alkyl group or a fluorinated alkyl group is preferable, and a hydrogen atom or a methyl group is particularly desirable in terms of industrial availability.

In general formula (a0-1), $R^2$ represents a divalent linking group.

Preferable examples of $R^2$ include a divalent hydrocarbon group which may have a substituent, and a divalent linking group containing a hetero atom.

Divalent Hydrocarbon Group which May have a Substituent

With respect to $R^2$, the hydrocarbon group "has a substituent" means that part or all of the hydrogen atoms within the hydrocarbon group has been substituted with a group or an atom other than a hydrogen atom.

The hydrocarbon group may be either an aliphatic hydrocarbon group or an aromatic hydrocarbon group. An "aliphatic hydrocarbon group" refers to a hydrocarbon group that has no aromaticity.

The aliphatic hydrocarbon group may be saturated or unsaturated. In general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

The linear or branched aliphatic hydrocarbon group preferably has 1 to 10 carbon atoms, more preferably 1 to 8, still more preferably 1 to 5, and most preferably 1 or 2.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of the substituent include a fluorine atom, a fluorinated lower alkyl group of 1 to 5 carbon atoms, and an oxygen atom (=O).

As examples of the hydrocarbon group containing a ring in the structure thereof, a cyclic aliphatic hydrocarbon group (a group in which two hydrogen atoms have been removed from an aliphatic hydrocarbon ring), and a group in which the cyclic aliphatic hydrocarbon group is bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane.

As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of the substituent include a lower alkyl group of 1 to 5 carbon atoms, a fluorine atom, a fluorinated lower alkyl group of 1 to 5 carbon atoms, and an oxygen atom (=O).

Examples of aromatic hydrocarbon groups include a divalent aromatic hydrocarbon group in which one hydrogen atom has been removed from a benzene ring of a monovalent aromatic hydrocarbon group such as a phenyl group, a biphenyl group, a fluorenyl group, a naphthyl group, an anthryl group or a phenanthryl group;

an aromatic hydrocarbon group in which part of the carbon atoms constituting the ring of the aforementioned divalent aromatic hydrocarbon group has been substituted with a hetero atom such as an oxygen atom, a sulfur atom or a nitrogen atom; and and an aromatic hydrocarbon group in which one hydrogen atom has been removed from a benzene ring of an arylalkyl group such as a benzyl group, a phenethyl group, a 1-naphthylmethyl group, a 2-naphthylmethyl group, a 1-naphthylethyl group or a 2-naphthylethyl group.

The aromatic hydrocarbon group may or may not have a substituent. Examples of the substituent include a lower alkyl group of 1 to 5 carbon atoms, a fluorine atom, a fluorinated lower alkyl group of 1 to 5 carbon atoms, and an oxygen atom (=O).

Divalent Linking Group Containing a Hetero Atom

With respect to the "divalent linking group containing a hetero atom" for $R^2$, a hetero atom refers to an atom other than carbon and hydrogen, and examples thereof include an oxygen atom, a nitrogen atom, a sulfur atom and a halogen atom.

Specific examples of the divalent linking group containing a hetero atom include —O—, —C(=O)—, —C(=O)—O—, a carbonate bond (—O—C(=O)—O—), —NH—, —NR$^{04}$— (R$^{04}$ represents an alkyl group), —NH—C(=O)—, and =N—. Further, a combination of any one of these "divalent linking groups containing a hetero atom" with a divalent hydrocarbon group can also be used. As examples of the divalent hydrocarbon group, the same groups as those described above for the hydrocarbon group which may have a substituent can be given, and a linear or branched aliphatic hydrocarbon group is preferable.

$R^2$ may or may not have an acid dissociable portion in the structure thereof.

An "acid dissociable portion" refers to a portion within the organic group which is dissociated from the organic group by action of acid generated upon exposure. When the $R^2$ group has an acid dissociable portion, it preferably has an acid dissociable portion having a tertiary carbon atom.

In the present invention, as the divalent linking group for $R^2$, an alkylene group, a divalent aliphatic cyclic group or a divalent linking group containing a hetero atom is preferable. Among these, an alkylene group is particularly desirable.

When $R^2$ represents an alkylene group, it preferably has 1 to 10 carbon atoms, more preferably 1 to 6, still more preferably 1 to 4, and most preferably 1 to 3. Specific examples of alkylene groups include the aforementioned linear alkylene groups and branched alkylene groups.

When $R^2$ represents a divalent aliphatic cyclic group, as the aliphatic cyclic group, the same aliphatic cyclic groups as those described above for the "aliphatic hydrocarbon group containing a ring in the structure thereof" can be used.

As the aliphatic cyclic group, a group in which two hydrogen atoms have been removed from cyclopentane, cyclohexane, norbornane, isobornane, adamantane, tricyclodecane or tetracyclododecane is particularly desirable.

When $R^2$ represents a divalent linkage group containing a hetero atom, preferable examples of linkage groups include —O—, —C(=O)—O—, —C(=O)—, —O—C(=O)—O—, —C(=O)—NH—, —NH— (H may be replaced with a substituent such as an alkyl group, an acyl group or the like), —S—, —S(=O)$_2$—, —S(=O)$_2$—O—, a group represented by the formula -A-O—B—, and a group represented by the formula -[A-C(=O)—O]$_u$—B—. Herein, each of A and B independently represents a divalent hydrocarbon group which may have a substituent, and u represents an integer of 0 to 3.

When $R^2$ represents —NH—, H may be replaced with a substituent such as an alkyl group, an acyl group or the like. The substituent (an alkyl group, an acyl group or the like) preferably has 1 to 10 carbon atoms, more preferably 1 to 8, and most preferably 1 to 5.

In the group represented by the formula -A-O—B— or -[A-C(=O)—O]$_u$—B—, each of A and B independently represents a divalent hydrocarbon group which may have a substituent.

Examples of divalent hydrocarbon groups for A and B which may have a substituent include the same groups as those described above for the "divalent hydrocarbon group which may have a substituent" usable as A or B explained in relation to $Y^2$.

As A, a linear aliphatic hydrocarbon group is preferable, more preferably a linear alkylene group, still more preferably a linear alkylene group of 1 to 5 carbon atoms, and a methylene group or an ethylene group is particularly desirable.

As B, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula -[A-C(=O)—O]$_u$—B—, u represents an integer of 0 to 3, preferably an integer of 0 to 2, more preferably 0 or 1, and most preferably 1.

In general formula (a0-1), $R^3$ represents a cyclic group containing —$SO_2$— within the ring skeleton thereof. More specifically, $R^3$ is a cyclic group in which the sulfur atom (S) within the —$SO_2$— group forms part of the ring skeleton thereof.

The cyclic group for $R^3$ refers to a cyclic group including a ring that contains —$SO_2$— within the ring skeleton thereof, and this ring is counted as the first ring. A cyclic group in which the only ring structure is the ring that contains —$SO_2$— in the ring skeleton thereof is referred to as a monocyclic group, and a group containing other ring structures is described as a polycyclic group regardless of the structure of the other rings. The cyclic group for $R^3$ may be either a monocyclic group or a polycyclic group.

As $R^3$, a cyclic group containing —O—$SO_2$— within the ring skeleton thereof, i.e., a cyclic group containing a sultone ring in which —O—S— within the —O—$SO_2$— group forms part of the ring skeleton thereof is particularly desirable.

The cyclic group for $R^3$ preferably has 3 to 30 carbon atoms, more preferably 4 to 20, still more preferably 4 to 15, and most preferably 4 to 12.

Herein, the number of carbon atoms refers to the number of carbon atoms constituting the ring skeleton, excluding the number of carbon atoms within a substituent.

The cyclic group for $R^3$ may be either an aliphatic cyclic group or an aromatic cyclic group.

An aliphatic cyclic group is preferable.

Examples of aliphatic cyclic groups for $R^3$ include the aforementioned cyclic aliphatic hydrocarbon groups in which part of the carbon atoms constituting the ring skeleton thereof has been substituted with —$SO_2$— or —O—$SO_2$—.

More specifically, examples of monocyclic groups include a monocycloalkane in which one hydrogen atom have been removed therefrom and a —$CH_2$— group constituting the ring skeleton thereof has been substituted with —$SO_2$—; and a monocycloalkane in which one hydrogen atom have been removed therefrom and a —$CH_2$—$CH_2$— group constituting the ring skeleton thereof has been substituted with —O—$SO_2$—. Examples of polycyclic groups include a polycycloalkane (a bicycloalkane, a tricycloalkane, a tetracycloalkane or the like) in which one hydrogen atom have been removed therefrom and a —$CH_2$— group constituting the ring skeleton thereof has been substituted with —$SO_2$—; and a polycycloalkane in which one hydrogen atom have been removed therefrom and a —$CH_2$—$CH_2$— group constituting the ring skeleton thereof has been substituted with —O—$SO_2$—.

The cyclic group for $R^3$ may have a substituent. Examples of the substituent include an alkyl group, an alkoxy group, a halogen atom, a halogenated alkyl group, a hydroxy group, an oxygen atom (=O), —COOR", —OC(=O)R", a hydroxyalkyl group and a cyano group. R" is the same as defined for R" above, namely, a hydrogen atom or an alkyl group.

The alkyl group for the substituent is preferably an alkyl group of 1 to 6 carbon atoms. Further, the alkyl group is preferably a linear alkyl group or a branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or ethyl group is preferable, and a methyl group is particularly desirable.

As the alkoxy group for the substituent, an alkoxy group of 1 to 6 carbon atoms is preferable. Further, the alkoxy group is preferably a linear alkoxy group or a branched alkyl group.

Specific examples of the alkoxy group include the aforementioned alkyl groups for the substituent having an oxygen atom (—O—) bonded thereto.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

As examples of the halogenated lower alkyl group for the substituent, groups in which part or all of the hydrogen atoms of the aforementioned alkyl groups for the substituent have been substituted with the aforementioned halogen atoms can be given. As the halogenated alkyl group, a fluorinated alkyl group is preferable, and a perfluoroalkyl group is particularly desirable.

In the —COOR" group and the —OC(=O)R" group, R" preferably represents a hydrogen atom or a linear, branched or cyclic alkyl group of 1 to 15 carbon atoms.

When R" represents a linear or branched alkyl group, it is preferably an alkyl group of 1 to 10 carbon atoms, more preferably an alkyl group of 1 to 5 carbon atoms, and most preferably a methyl group or an ethyl group.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

The hydroxyalkyl group for the substituent preferably has 1 to 6 carbon atoms, and specific examples thereof include the aforementioned alkyl groups for the substituent in which at least one hydrogen atom has been substituted with a hydroxy group.

More specific examples of $R^3$ include groups represented by general formulas (3-1) to (3-4) shown below.

[Chemical Formula 36]

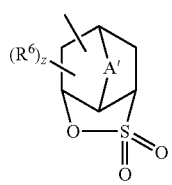

(3-1)

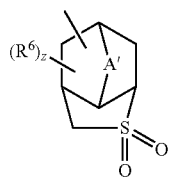

(3-2)

-continued (3-3)
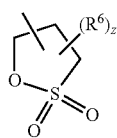

(3-4)
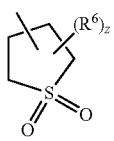

In the formulas, A' represents an oxygen atom, a sulfur atom, or an alkylene group of 1 to 5 carbon atoms which may contain an oxygen atom or a sulfur atom; z represents an integer of 0 to 2; and $R^6$ represents an alkyl group, an alkoxy group, a halogenated alkyl group, a hydroxyl group, —COOR", —OC(=O)R", a hydroxyalkyl group or a cyano group, wherein R" represents a hydrogen atom or an alkyl group.

In general formulas (3-1) to (3-4) above, A' represents an oxygen atom (—O—), a sulfur atom (—S—), or an alkylene group of 1 to 5 carbon atoms which may contain an oxygen atom or a sulfur atom.

As the alkylene group of 1 to 5 carbon atoms represented by A', a linear or branched alkylene group is preferable, and examples thereof include a methylene group, an ethylene group, an n-propylene group and an isopropylene group.

Examples of alkylene groups that contain an oxygen atom or a sulfur atom include the aforementioned alkylene groups in which —O— or —S— is bonded to the terminal of the alkylene group or interposed within the alkyl group. Specific examples of such alkylene groups include —O—CH$_2$—, —CH$_2$—O—CH$_2$—, —S—CH$_2$—, —CH$_2$—S—CH$_2$—.

As A', an alkylene group of 1 to 5 carbon atoms or —O— is preferable, more preferably an alkylene group of 1 to 5 carbon atoms, and most preferably a methylene group.

z represents an integer of 0 to 2, and is most preferably 0.

When z is 2, the plurality of $R^2$ may be the same or different from each other.

As the alkyl group, alkoxy group, halogenated alkyl group, —COOR", —OC(=O)R" and hydroxyalkyl group for $R^6$, the same alkyl groups, alkoxy groups, halogenated alkyl groups, —COOR", —OC(=O)R" and hydroxyalkyl groups as those described above as the substituent which the cyclic group for $R^3$ may have can be used.

Specific examples of the cyclic groups represented by general formulas (3-1) to (3-4) are shown below. In the formulas shown below, "Ac" represents an acetyl group.

[Chemical Formula 37]

(3-1-1)
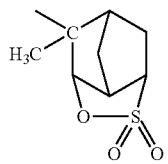

(3-1-2)
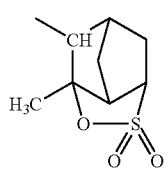

(3-1-3)
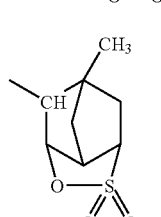

(3-1-4)
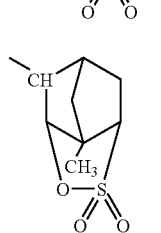

(3-1-5)
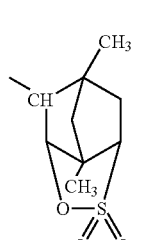

(3-1-6)
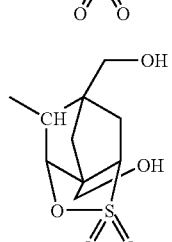

(3-1-7)
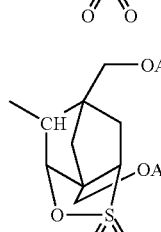

(3-1-8)
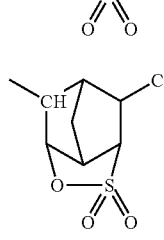

(3-1-9)
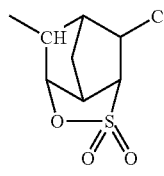

(3-1-10)
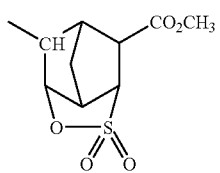
(3-1-11)
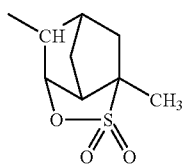
(3-1-12)
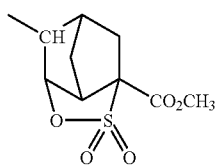
(3-1-13)
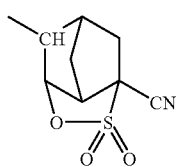
(3-1-14)
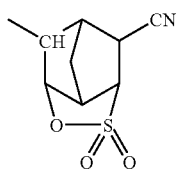
(3-1-15)
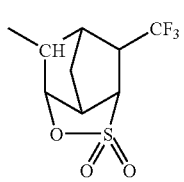
(3-1-16)
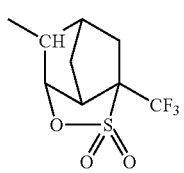
(3-1-17)
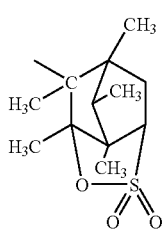
[Chemical Formula 38]
(3-1-18)
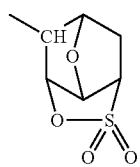
(3-1-19)
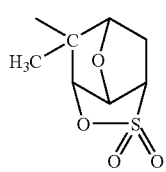
(3-1-20)
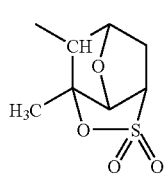
(3-1-21)
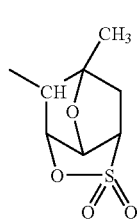
(3-1-22)
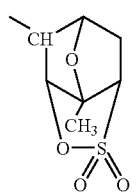
(3-1-23)
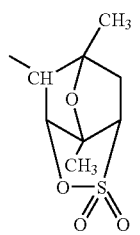
(3-1-24)
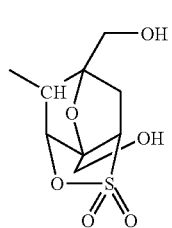
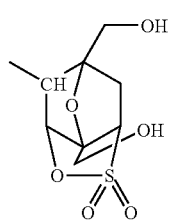

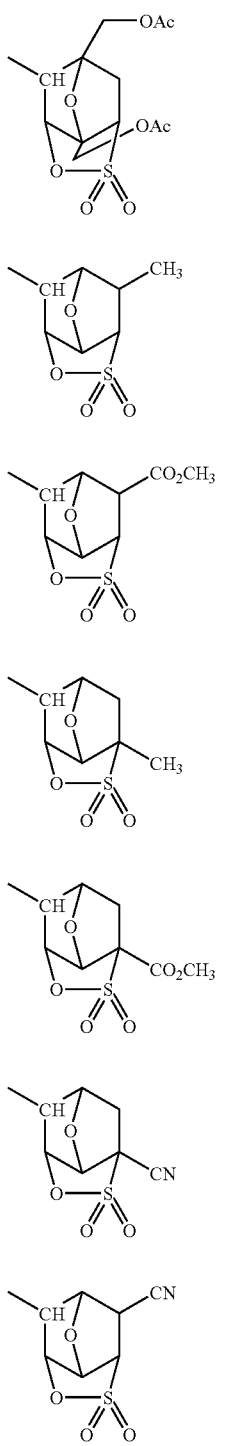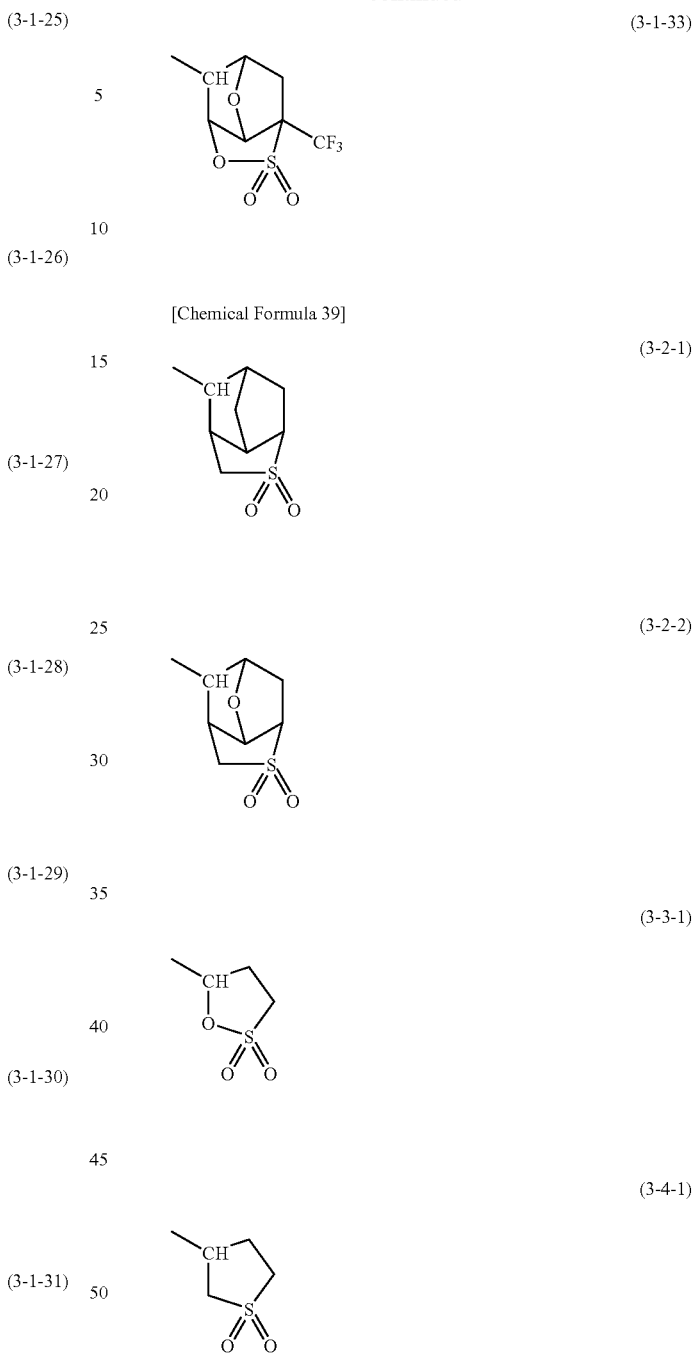

Among the examples shown above, as $R^3$, a group represented by general formula (3-1), (3-3) or (3-4) shown below is preferable, and a cyclic group represented by general formula (3-1) shown below is particularly desirable.

More specifically, as $R^3$, it is preferable to use at least one cyclic group selected from the group consisting of groups represented by chemical formulas (3-1-1), (3-1-18), (3-3-1) and (3-4-1) above, and a group represented by chemical formula (3-1-1) above is particularly desirable.

In the present invention, as the structural unit (a0), a structural unit represented by general formula (a0-1-11) shown below is particularly desirable.

[Chemical Formula 40]

(a0-1-11)

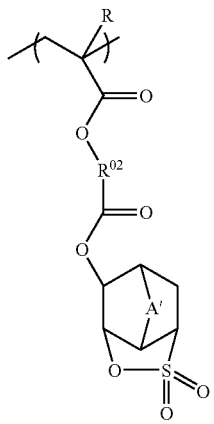

In the formula, R is the same as defined above; $R^{02}$ represents a linear or branched alkylene group; and A' is the same as defined above.

The linear or branched alkylene group for $R^{02}$ preferably has 1 to 10 carbon atoms, more preferably 1 to 8, still more preferably 1 to 5, still more preferably 1 to 3, and most preferably 1 or 2.

A' is preferably a methylene group, an oxygen atom (—O—) or a sulfur atom (—S—).

As the structural unit (a0), one type of structural unit may be used alone, or two or more types of structural units may be used in combination.

In terms of achieving excellent properties with respect to mask error factor (MEF), the shape of a formed resist pattern (e.g., rectangularity of a liner pattern, circularity of a hole pattern and the like), in-plane uniformity (CDU), line width roughness (LWR) and the like in the formation of a resist pattern using a resist composition containing the component (A1), the amount of the structural unit (a0) within the component (A1), based on the combined total of all structural units constituting the component (A1) is preferably 1 to 60 mol %, more preferably 5 to 50 mol %, still more preferably 10 to 40 mol %, and most preferably 20 to 40 mol %.

In the present invention, the component (A) is preferably a polymer including the structural unit (a1).

Examples of such a polymer include a copolymer consisting of a structural unit (a1) and a structural unit (a2); a copolymer consisting of a structural unit (a1) and a structural unit (a3); a copolymer consisting of a structural unit (a1), a structural unit (a2) and a structural unit (a3); a copolymer consisting of a structural unit (a1), a structural unit (a2), a structural unit (a3) and a structural unit (a4); a copolymer consisting of a structural unit (a0) and a structural unit (a1); a copolymer consisting of a structural unit (a0), a structural unit (a1) and a structural unit (a2); a copolymer consisting of a structural unit (a0), a structural unit (a1) and a structural unit (a3); and copolymer consisting of a structural unit (a0), a structural unit (a1), a structural unit (a2) and a structural unit (a3).

In the resist composition of the present invention, it is particularly desirable that such a copolymer contains, as the structural unit (a1), at least one member selected from the group consisting of a structural unit represented by general formula (a1-0-11), a structural unit represented by general formula (a1-0-12), and a structural unit represented by general formula (a1-1-01).

Further, as described above, such a copolymer preferably contains at least two types of structural units as the structural unit (a1). It is more preferable that at least one of the at least two structural units is selected from the group consisting of a structural unit represented by general formula (a1-0-11) and a structural unit represented by general formula (a1-0-12). It is particularly desirable that both of the at least two types of structural units are selected from the aforementioned group.

Further, in terms of achieving excellent lithography properties, the total amount of the structural unit (a0) and the structural unit (a2) (the amount of the structural unit (a0) when the component (A1) contains no structural unit (a2)) within the component (A1), based on the combined total of all structural units constituting the component (A1) is preferably 1 to 70 mol %, more preferably 5 to 70 mol %, still more preferably 10 to 65 mol %, and most preferably 20 to 65 mol %. By ensuring the above-mentioned range, the exposure latitude (EL margin), MEF, CDU and the pattern shape can be further improved.

When the component (A1) contains both of the structural unit (a0) and the structural unit (a2), the amount of the structural unit (a0) within the component (A1), based on the combined total of all structural units constituting the component (A1) is preferably 1 to 40 mol %, more preferably 10 to 35 mol %, and most preferably 15 to 30 mol %; and the amount of the structural unit (a2) within the component (A1), based on the combined total of all structural units constituting the component (A1) is preferably 1 to 45 mol %, more preferably 10 to 45 mol %, and most preferably 20 to 45 mol %.

The weight average molecular weight (Mw) (the polystyrene equivalent value determined by gel permeation chromatography) of the component (A1) is not particularly limited, but is preferably 2,000 to 50,000, more preferably 3,000 to 30,000, and most preferably 5,000 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) is preferably 1.0 to 5.0, more preferably 1.0 to 3.0, and most preferably 1.2 to 2.5. Here, Mn is the number average molecular weight.

In the component (A), as the component (A1), one type may be used, or two or more types of compounds may be used in combination.

In the component (A), the amount of the component (A1) based on the total weight of the component (A) is preferably 25% by weight or more, more preferably 50% by weight or more, still more preferably 75% by weight or more, and may be even 100% by weight. When the amount of the component (A1) is 25% by weight or more, various lithography properties are improved.

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

As the monomers for deriving the corresponding structural units, commercially available monomers may be used, or the monomers may be synthesized by a conventional method.

For example, as a monomer for deriving the structural unit (a0), a compound represented by general formula (a0-1-0) shown below (hereafter, referred to as "compound (a0-1-0)") can be used.

[Chemical Formula 41]

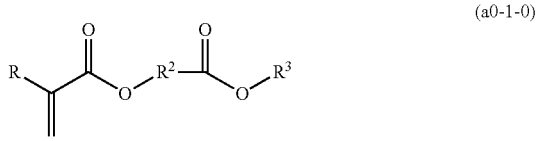

(a0-1-0)

In general formula (a0-1-0), R, $R^2$ and $R^3$ are the same as defined above.

The method for producing the compound (a0-1-0) is not particularly limited, and the compound (a0-1-0) can be produced by a conventional method.

For example, in the presence of a base, a compound (X-2) represented by general formula (X-2) shown below is added to a solution obtained by dissolving a compound (X-1) represented by general formula (X-1) shown below in a reaction solvent, and a reaction is effected to thereby obtain a compound (a0-1-0).

Examples of the base include inorganic bases such as sodium hydride, $K_2CO_3$ and $Cs_2CO_3$; and organic bases such as triethylamine, 4-dimethylaminopyridine (DMAP) and pyridine. Examples of condensing agents include carbodiimide reagents such as ethyldiisopropylaminocarbodiimide hydrochloride (EDCI), dicyclohexylcarboxylmide (DCC), diisopropylcarbodiimide and carbodiimidazole; tetraethyl pyrophosphate; and benzotriazole-N-hydroxytrisdimethylaminophosphonium hexafluorophosphide (Bop reagent).

If desired, an acid may be used. As the acid, any acid generally used for dehydration/condensation may be used. Specific examples include inorganic acids such as hydrochloric acid, sulfuric acid and phosphoric acid; and organic acids such as methanesulfonic acid, trifluoromethanesulfonic acid, benzenesulfonic acid and p-toluenesulfonic acid. These acids can be used individually, or in a combination of two or more.

[Chemical Formula 42]

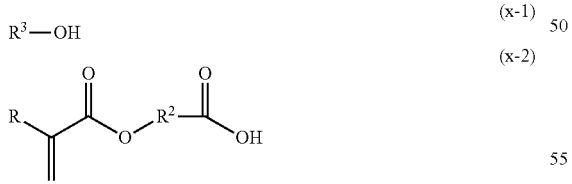

(x-1)

(x-2)

[Component (A2)]

As the component (A2), it is preferable to use a compound that has a molecular weight of at least 500 and less than 2,000, contains a hydrophilic group, and also contains an acid dissociable, dissolution inhibiting group described above in connection with the component (A1). Specific examples include compounds containing a plurality of phenol skeletons in which a part of the hydrogen atoms within hydroxyl groups have been substituted with the aforementioned acid dissociable, dissolution inhibiting groups.

Examples of the component (A2) include low molecular weight phenolic compounds in which a portion of the hydroxyl group hydrogen atoms have been substituted with an aforementioned acid dissociable, dissolution inhibiting group, and these types of compounds are known, for example, as sensitizers or heat resistance improvers for use in non-chemically amplified g-line or i-line resists.

Examples of these low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3',4'-trihydroxyphenyl)propane, tris(4-hydroxyphenyl)methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers, trimers and tetramers of formalin condensation products of phenols such as phenol, m-cresol, p-cresol and xylenol. Needless to say, the low molecular weight phenol compound is not limited to these examples.

Also, there are no particular limitations on the acid dissociable, dissolution inhibiting group, and suitable examples include the groups described above.

As the component (A2), one type of resin may be used, or two or more types of resins may be used in combination.

In the resist composition of the present invention, as the component (A), one type may be used, or two or more types of compounds may be used in combination.

Of the examples shown above, as the component (A), it is preferable to use one containing the component (A1).

In the resist composition of the present invention, the amount of the component (A) can be appropriately adjusted depending on the thickness of the resist film to be formed, and the like.

<Component (B)>

The resist composition of the present invention contains an acid-generator component (B) which generates acid upon exposure, and the component (B) includes an acid generator (B1) (hereafter, referred to as "component (B1)") containing a compound having a group represented by general formula (I) shown below On a cation moiety thereof.

[Chemical Formula 43]

(I)

In formula (I), $R^5$ represents a hydrogen atom or an organic group of 1 to 30 carbon atoms which may have a substituent; and $Q^5$ represents a single bond or a divalent linking group.

In formula (I), $R^5$ represents a hydrogen atom or an organic group of 1 to 30 carbon atoms which may have a substituent.

In general formula (I), the organic group represented by $R^5$ may be either an aromatic hydrocarbon group or an aliphatic hydrocarbon group. Alternatively, the organic group may be a cyano group (—CN).

Examples of the aliphatic hydrocarbon group for $R^5$ include a linear, branched or cyclic, saturated hydrocarbon group of 1 to 15 carbon atoms and a linear, branched or cyclic, unsaturated hydrocarbon group of 2 to 5 carbon atoms.

Examples of the linear, saturated hydrocarbon group include a methyl group, an ethyl group, a propyl group, a butyl group, a pentyl group, a hexyl group, a heptyl group, an octyl group, a nonyl group and a decanyl group.

Examples of the branched, saturated hydrocarbon group include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The linear or branched alkyl group may have a substituent. Examples of the substituent include an alkoxy group, a halogen atom, a halogenated alkyl group, a hydroxyl group, an oxygen atom (=O), a cyano group and a carboxy group.

The alkoxy group as the substituent for the linear or branched alkyl group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom as the substituent for the linear or branched alkyl group include a fluorine atom, a chlorine atom, a bromine atom and an iodine atom, and a fluorine atom is preferable.

Examples of the halogenated alkyl group as a substituent for the linear or branched alkyl group include groups in which part or all of the hydrogen atoms within an alkyl group of 1 to 5 carbon atoms (preferably a methyl group, an ethyl group, a propyl group, an n-butyl group, a tert-butyl group, or the like) have been substituted with the aforementioned halogen atoms.

The cyclic, saturated hydrocarbon group may be either a polycyclic group or a monocyclic group. Examples thereof include cyclic, saturated hydrocarbon groups of 3 to 20 carbon atoms, such as groups in which one hydrogen atom has been removed from a monocycloalkane or a polycycloalkane (e.g., a bicycloalkane, a tricycloalkane or a tetracycloalkane). More specific examples include groups in which one hydrogen atom has been removed from a monocycloalkane such as cyclopentane, cyclohexane, cycloheptane or cyclooctane; and groups in which one hydrogen atom has been removed from a polycycloalkane such as adamantane, norbornane, isobornane, tricyclodecane or tetracyclododecane.

The cyclic alkyl group may have a substituent. For example, part of the carbon atoms constituting the ring within the cyclic alkyl group may be substituted with a hetero atom, or a hydrogen atom bonded to the ring within the cyclic alkyl group may be substituted with a substituent.

In the former example, a heterocycloalkane in which part of the carbon atoms constituting the ring within the aforementioned monocycloalkane or polycycloalkane has been substituted with a hetero atom such as an oxygen atom, a sulfur atom or a nitrogen atom, and one hydrogen atom has been removed therefrom, can be used. Further, the ring may contain an ester bond (—C(=O)—O—). More specific examples include a lactone-containing monocyclic group, such as a group in which one hydrogen atom has been removed from γ-butyrolactone; and a lactone-containing polycyclic group, such as a group in which one hydrogen atom has been removed from a bicycloalkane, tricycloalkane or tetracycloalkane containing a lactone ring.

In the latter example, as the substituent, the same substituent groups as those for the aforementioned linear or branched alkyl group, or an alkyl group of 1 to 5 carbon atoms can be used.

Examples of linear unsaturated hydrocarbon groups include a vinyl group, a propenyl group (an allyl group) and a butynyl group.

Examples of branched unsaturated hydrocarbon groups include a 1-methylpropenyl group and a 2-methylpropenyl group.

The aforementioned linear or branched, unsaturated hydrocarbon group may have a substituent. Examples of substituents include the same substituents as those which the aforementioned linear or branched alkyl group may have.

The aromatic hydrocarbon group for $R^5$ is a hydrocarbon group having an aromatic ring. The aromatic hydrocarbon ring preferably has 3 to 30 carbon atoms, more preferably 5 to 30, still more preferably 5 to 20, still more preferably 6 to 15, and most preferably 6 to 12. Here, the number of carbon atoms within a substituent(s) is not included in the number of carbon atoms of the aromatic hydrocarbon group.

The aromatic hydrocarbon group may be either a group including an aromatic hydrocarbon ring in which the ring skeleton of the aromatic ring is constituted of only carbon atoms, or a group including an aromatic hetero ring in which the ring skeleton of the aromatic ring contains not only carbon atoms but also a hetero atom.

Examples of the aromatic hydrocarbon group include an aryl group which is an aromatic hydrocarbon ring having one hydrogen atom removed therefrom, such as a phenyl group, a biphenyl group, a fluorenyl group, a naphthyl group, an anthryl group or a phenanthryl group; a heteroaryl group in which part of the carbon atoms constituting the aforementioned aryl group has been substituted with a hetero atom such as an oxygen atom, a sulfur atom or a nitrogen atom; and an arylalkyl group, such as a benzyl group, a phenethyl group, a 1-naphthylmethyl group, a 2-naphthylmethyl group, a 1-naphthylethyl group or a 2-naphthylethyl group. The alkyl chain within the arylalkyl group preferably has 1 to 4 carbon atom, more preferably 1 or 2, and most preferably 1.

The aromatic hydrocarbon group may have a substituent. For example, part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

In the former example, a heteroaryl group in which part of the carbon atoms constituting the ring within the aforementioned aryl group has been substituted with a hetero atom such as an oxygen atom, a sulfur atom or a nitrogen atom, and a heteroarylalkyl group in which part of the carbon atoms constituting the ring of the aforementioned arylalkyl group has been substituted with the aforementioned heteroatom can be used.

In the latter example, as the substituent for the aromatic group, an alkyl group, an alkoxy group, a halogen atom, a halogenated alkyl group, a hydroxyl group, an oxygen atom (=O), an acetyl group or the like can be used.

Examples of the alkyl group, alkoxy group, halogen atom and halogenated alkyl group as the substituent for the aromatic group include the same substituent groups as those for the aforementioned linear or branched alkyl group, and an alkyl group of 1 to 5 carbon atoms.

Among the aforementioned examples, in terms of reducing defects and forming a resist pattern having an excellent shape, the hydrocarbon group for $R^5$ is preferably an aliphatic hydrocarbon group, more preferably a linear, branched or cyclic, saturated hydrocarbon group, still more preferably a linear saturated hydrocarbon group, and most preferably a linear alkyl group of 1 to 4 carbon atoms.

Alternatively, the hydrocarbon group for $R^5$ is preferably a bulky hydrocarbon group, more preferably an aromatic hydrocarbon group, and most preferably a phenyl group.

By virtue of $R^5$ being a bulky group, the uniformity of the distribution of the component (B1) within a resist film can be improved. Further, dissolution inhibiting effect can be obtained at unexposed portions of the resist film, thereby enabling the formation of a resist pattern having an excellent shape. The reason why such effects can be achieved is presumed that, when $R^5$ is a bulky group, the dissolution rate in an alkali developing solution becomes low, thereby suppressing thickness loss especially at unexposed portions.

In formula (I), $Q^5$ represents a single bond or a divalent linking group.

Examples of the divalent linking group for $Q^5$ include an alkylene group and a group containing a hetero atom, and a group containing a hetero atom is preferable in terms of forming a resist pattern having an excellent shape.

A "hetero atom" is an atom other than carbon and hydrogen, and examples thereof include an oxygen atom, a sulfur atom and a nitrogen atom.

The alkylene group is preferably a linear or branched alkylene group, more preferably an alkylene group of 1 to 5 carbon atoms, still more preferably an alkylene group of 1 to 3 carbon atoms, and most preferably a methylene group, an ethylene group or a propylene group.

Examples of the group containing a hetero atom include non-hydrocarbon, oxygen atom-containing linking groups such as an oxygen atom (an ether bond; —O—), an ester bond (—C(=O)—O—), an amido bond (—C(=O)—NH—), a carbonyl group (—C(=O)—), a carbonate group (—O—C(=O)—O—) and a thioester bond (C(=O)—S—); and combinations of the aforementioned non-hydrocarbon, hetero atom-containing linking groups with an alkylene group.

Specific examples of the combinations of the aforementioned non-hydrocarbon, hetero atom-containing linking groups and an alkylene group include —$R^{97}$—O—, —$R^{97}$—C(=O)—, —$R^{98}$—O—C(=O)—, —$R^{98}$—C(=O)—O—, —$R^{98}$—S—C(=O)—, —O—$R^{98}$—O—C(=O)—, —C(=O)—O—$R^{99}$—O—C(=O)— and —C(=O)—O—$R^{99}$— (in the formulas, each of $R^{97}$ to $R^{99}$ independently represents an alkylene group).

As the alkylene group for $R^{97}$ to $R^{99}$, a linear or branched alkylene group is preferable. The alkylene group preferably has 1 to 10 carbon atoms, more preferably 1 to 7 carbon atoms, and most preferably 1 to 5 carbon atoms. It is presumed that the alkylene group exhibits the same effects as in the case where $R^5$ is a bulky group. Therefore, the alkylene group may be may be replaced with a phenylene group, or the alkylene group may have a phenyl group.

Among the aforementioned examples, $Q^5$ is preferably a divalent linking group containing a single bond, an ester bond, a thioester bond, a carbonyl group or an ether group, more preferably a single bond, —O—, —$R^{97}$—O—, —$R^{97}$—C(=O)—, —O—C(=O)—, —$R^{98}$—O—C(=O)—, —$R^{98}$—C(=O)—O— or —C(=O)—O—$R^{99}$—, still more preferably —$R^{98}$—O—C(=O)— or —O—C(=O)—, and most preferably —O—C(=O)—.

In the present invention, the component (B1) is not particularly limited, as long as it has a group represented by general formula (I) on a cation moiety thereof. In terms of reducing defects and forming a resist pattern having an excellent shape, the component (B1) is preferably a compound represented by general formula (b1-11) shown below.

[Chemical Formula 44]

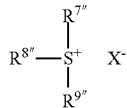

(b1-11)

In formula (b1-11), each of $R^{7\prime\prime}$ to $R^{9\prime\prime}$ independently represents an aryl group or an alkyl group, and two of $R^{7\prime\prime}$ to $R^{9\prime\prime}$ may be mutually bonded to form a ring with the sulfur atom, provided that at least one of $R^{7\prime\prime}$ to $R^{9\prime\prime}$ represents a substituted aryl group having a group represented by general formula (I) as a substituent; and $X^-$ represents an anion.

In general formula (b1-11), each of $R^{7\prime\prime}$ to $R^{9\prime\prime}$ independently represents an aryl group or an alkyl group, provided that at least one of $R^{7\prime\prime}$ to $R^{9\prime\prime}$ represents a substituted aryl group having a group represented by general formula (I) as a substituent.

The aryl group for $R^{7\prime\prime}$ to $R^{9\prime\prime}$ is not particularly limited. For example, an aryl group having 6 to 20 carbon atoms may be used in which part or all of the hydrogen atoms of the aryl group may or may not be substituted with a substituent other than those represented by general formula (I), e.g., an alkyl group, an alkoxy group, a halogen atom or a hydroxyl group.

The aryl group is preferably an aryl group having 6 to 10 carbon atoms because it can be synthesized at a low cost. Specific examples thereof include a phenyl group and a naphthyl group.

The alkyl group, with which hydrogen atoms of the aryl group may be substituted, is preferably an alkyl group having 1 to 5 carbon atoms, more preferably a methyl group, an ethyl group, a propyl group, an n-butyl group, or a tert-butyl group, and most preferably a methyl group.

The alkoxy group, with which hydrogen atoms of the aryl group may be substituted, is preferably an alkoxy group having 1 to 5 carbon atoms, more preferably a methoxy group, an ethoxy group, an n-propoxy group, an iso-propoxy group, an n-butoxy group or a tert-butoxy group.

The halogen atom, with which hydrogen atoms of the aryl group may be substituted, is preferably a fluorine atom.

The alkyl group for $R^{7\prime\prime}$ to $R^{9\prime\prime}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples include a methyl group, an ethyl group, an n-propyl group, an isopropyl group, an n-butyl group, an isobutyl group, an n-pentyl group, a cyclopentyl group, a hexyl group, a cyclohexyl group, a nonyl group and a decanyl group. Among these, a methyl group is preferable because it is excellent in resolution and can be synthesized at a low cost.

In general formula (b1-11), two of $R^{7\prime\prime}$ to $R^{9\prime\prime}$ may be mutually bonded to form a ring with the sulfur atom.

In such a case, the ring including the sulfur atom is preferably a 3- to 10-membered ring, and more preferably a 5- to 7-membered ring.

When two of $R^{7\prime\prime}$ to $R^{9\prime\prime}$ are mutually bonded to form a ring with the sulfur atom, the remaining one of $R^{7\prime\prime}$ to $R^{9\prime\prime}$ is preferably an aryl group. The aryl group is preferably a substituted aryl group having a group represented by general formula (I) as a substituent.

In the present invention, at least one of $R^{7\prime\prime}$ to $R^{9\prime\prime}$ represents a substituted aryl group (hereafter, referred to as "substituted aryl group (I)") having a group represented by general formula (I) as a substituent.

One substituted aryl group (I) preferably has 1 to 3 groups represented by general formula (I), and most preferably 1.

In the substituted aryl group (I), the aryl group to which the group represented by general formula (I) is bonded is preferably a phenyl group or a naphthyl group, and most preferably a phenyl group. In such a case, the group represented by general formula (I) is preferably bonded to the para position of the phenyl group.

The substituted aryl group (I) may have a substituent other than a group represented by general formula (I). Examples of such a substituent include an alkyl group, an alkoxy group, an ether group, a halogen atom, a halogenated alkyl group and a hydroxy group. As specific examples of these substituents, the same groups as those described above for the substituent of the aforementioned substituted aryl group can be mentioned.

The number of such a substituent that one substituted aryl group (I) has is preferably 0 to 2.

Among $R^{7\prime\prime}$ to $R^{9\prime\prime}$, either one, two or three may represent a substituted aryl group (I). However, it is particularly desirable that one of $R^{7\prime\prime}$ to $R^{9\prime\prime}$ represent a substituted aryl group (I).

In such a case, it is preferable that the remaining two represent an aryl group which may have a substituent other than a group represented by general formula (I), or the remaining two be mutually bonded to form a ring with the sulfur atom in the formula.

When each of the remaining two represents an aryl group which may have a substituent, the aryl group is preferably an unsubstituted aryl group, more preferably a phenyl group or a naphthyl group, and most preferably a phenyl group.

Specific examples of preferable cation moieties for the component (B1) are shown below. In the formula, q represents an integer of 1 to 3.

[Chemical Formula 45]

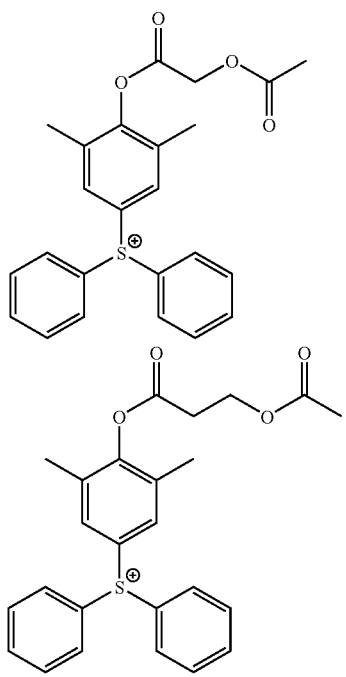

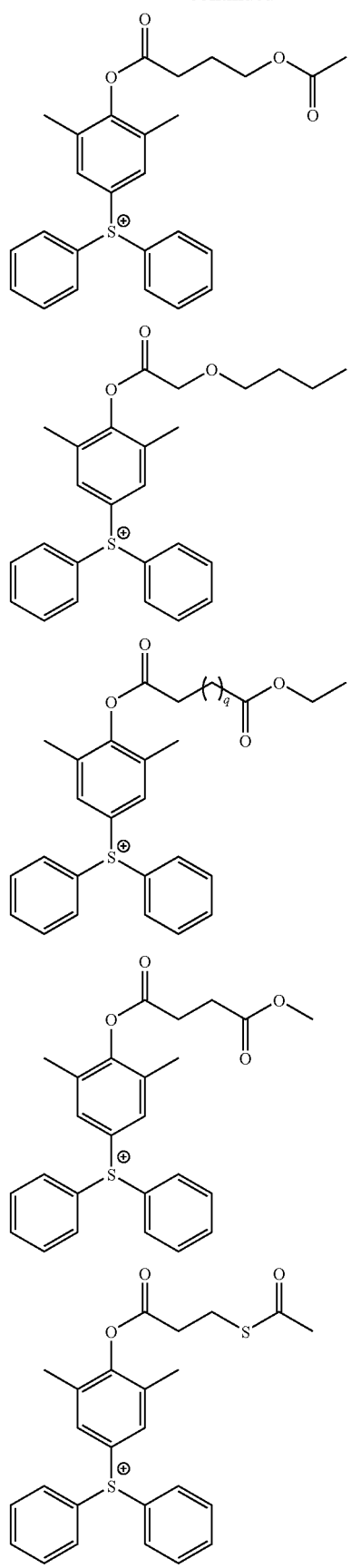

[Chemical Formula 46]
-continued

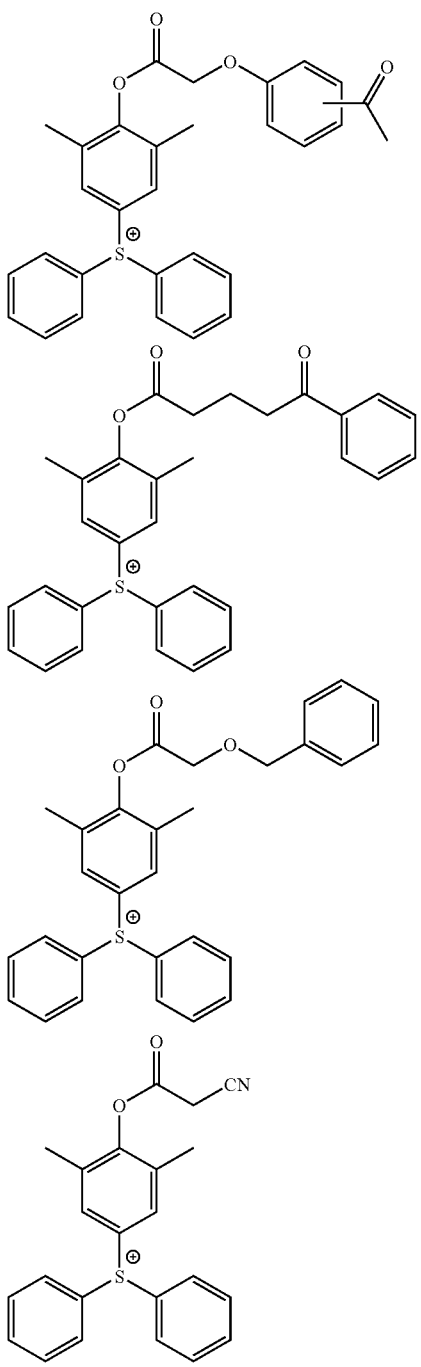

Anion Moiety of Component (B1)

In formula (b1-11), the anion represented by X⁻ is not particularly limited, and any of those known as an anion moiety for an onium salt-based acid generator can be appropriately selected for use.

As a preferable example of the anion moiety represented by X⁻, an anion represented by general formula (x-1) shown below can be given.

[Chemical Formula 47]

  (x-1)

In the formula, $R^{4'''}$ represents an alkyl group, a halogenated alkyl group, an aryl group or an alkenyl group, which may have a substituent.

The alkyl group for $R^{4'''}$ may be any of linear, branched or cyclic.

The linear or branched alkyl group preferably has 1 to 10 carbon atoms, more preferably 1 to 8 carbon atoms, and most preferably 1 to 4 carbon atoms.

The cyclic alkyl group preferably has 4 to 20 carbon atoms, more preferably 4 to 15 carbon atoms, still more preferably 4 to 10 carbon atoms, and most preferably 6 to 10 carbon atoms.

As an example of the halogenated alkyl group for $R^{4'''}$, a group in which part of or all of the hydrogen atoms of the aforementioned linear, branched or cyclic alkyl group have been substituted with halogen atoms can be given. Examples of the aforementioned halogen atom include a fluorine atom, a chlorine atom, a bromine atom and an iodine atom, and a fluorine atom is preferable.

In the halogenated alkyl group, the percentage of the number of halogen atoms based on the total number of halogen atoms and hydrogen atoms (halogenation ratio (%)) is preferably 10 to 100%, more preferably 50 to 100%, and most preferably 100%. Higher halogenation ratio is preferable because the acid strength increases.

The aryl group for $R^{4'''}$ is preferably an aryl group of 6 to 20 carbon atoms.

The alkenyl group for $R^{4'''}$ is preferably an alkenyl group of 2 to 10 carbon atoms.

With respect to $R^{4'''}$, the expression "may have a substituent" means that part of or all of the hydrogen atoms within the aforementioned alkyl group, halogenated alkyl group, aryl group or alkenyl group may be substituted with substituents (atoms other than hydrogen atoms, or groups).

$R^{4'''}$ may have one substituent, or two or more substituents.

Examples of the substituent include a halogen atom, a hetero atom, an alkyl group, an oxygen atom (=O) and a group represented by the formula Z-$Q^1$- (in the formula, $Q^1$ represents a divalent linking group containing an oxygen atom; and Z represents a hydrocarbon group of 3 to 30 carbon atoms which may have a substituent).

Examples of the halogen atom as a substituent for $R^{4'''}$ include the same halogen atoms as those described above with respect to the halogenated alkyl group for $R^{4'''}$.

Examples of the alkyl group as a substituent for $R^{4'''}$ include the same alkyl groups as those described above with respect to the alkyl group for $R^{4'''}$.

Examples of hetero atoms include an oxygen atom, a nitrogen atom, and a sulfur atom.

In the group represented by formula Z-$Q^1$-, $Q^1$ represents a divalent linking group containing an oxygen atom.

$Q^1$ may contain an atom other than an oxygen atom. Examples of atoms other than an oxygen atom include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—), an amido bond (—C(=O)—NH—), a carbonyl group (—C(=O)—) and a carbonate bond (—O—C(=O)—O—); and combinations of the aforementioned non-hydrocarbon, hetero atom-containing linking groups with an alkylene group.

Specific examples of such combinations include —$R^{91}$—O—, —$R^{92}$—O—C(=O)—, —C(=O)—O—$R^{93}$—O—C(=O)—, —O—$R^{93}$—O—C(=O)—, and —$R^{92}$—O—C(=O)—$R^{93}$—O—C(=O)— (in the formulas, each of $R^{91}$ to $R^{93}$ independently represents an alkylene group).

The alkylene group for $R^{91}$ to $R^{93}$ is preferably a linear or branched alkylene group, and preferably has 1 to 12 carbon atoms, more preferably 1 to 5, and most preferably 1 to 3.

Specific examples of alkylene groups include a methylene group [—$CH_2$—]; alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—; an ethylene group [—$CH_2CH_2$—]; alkylethylene groups such as —CH($CH_3$)$CH_2$—, —CH($CH_3$)CH($CH_3$)—, —C($CH_3$)$_2CH_2$— and —CH($CH_2CH_3$)$CH_2$—; a trimethylene group (n-propylene group) [—$CH_2CH_2CH_2$—]; alkyltrimethylene groups such as —CH($CH_3$)$CH_2CH_2$— and —$CH_2$CH($CH_3$)$CH_2$—; a tetramethylene group [—$CH_2CH_2CH_2CH_2$—]; alkyltetramethylene groups such as —CH($CH_3$)$CH_2CH_2CH_2$— and —$CH_2$CH($CH_3$)$CH_2CH_2$—; and a pentamethylene group [—$CH_2CH_2CH_2CH_2CH_2$—].

As $Q^1$, a divalent linking group containing an ester bond and/or an ether bond is preferable, and —O—, —$R^{91}$—O—, —$R^{92}$—O—C(=O)—, —C(=O)—O—, —C(=O)—O—$R^{93}$—, —C(=O)—O—$R^{93}$—O—C(=O)—, —O—$R^{93}$—O—C(=O)—, or —$R^{92}$—O—C(=O)—$R^{93}$—O—C(=O)— is more preferable.

In the group represented by the formula Z-$Q^1$-, the hydrocarbon group for Z may be either an aromatic hydrocarbon group or an aliphatic hydrocarbon group.

The aromatic hydrocarbon group is a hydrocarbon group having an aromatic ring. The aromatic hydrocarbon ring preferably has 3 to 30 carbon atoms, more preferably 5 to 30, still more preferably 5 to 20, still more preferably 6 to 15, and most preferably 6 to 12. Here, the number of carbon atoms within a substituent(s) is not included in the number of carbon atoms of the aromatic hydrocarbon group.

Specific examples of aromatic hydrocarbon groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an alkylaryl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atom, more preferably 1 or 2, and most preferably 1.

The aromatic hydrocarbon group may have a substituent. For example, part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

In the former example, a heteroaryl group in which part of the carbon atoms constituting the ring within the aforementioned aryl group has been substituted with a hetero atom such as an oxygen atom, a sulfur atom or a nitrogen atom, and a heteroarylalkyl group in which part of the carbon atoms constituting the aromatic hydrocarbon ring within the aforementioned arylalkyl group has been substituted with the aforementioned heteroatom can be used.

Examples of the substituent for the aromatic hydrocarbon group in the former example include an alkyl group, an alkoxy group, a halogen atom, a halogenated alkyl group, a hydroxy group, an oxygen atom (=O), —COOR", —OC(=O)R", a hydroxyalkyl group and a cyano group. R" represents a hydrogen atom or a linear, branched or cyclic alkyl group of 1 to 15 carbon atoms.

The alkyl group as the substituent for the aromatic hydrocarbon group is preferably an alkyl group of 1 to 5 carbon atoms, and a methyl group, an ethyl group, a propyl group, an n-butyl group or a tert-butyl group is particularly desirable.

The alkoxy group as the substituent for the aromatic hydrocarbon group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Example of the halogenated alkyl group as the substituent for the aromatic hydrocarbon group includes a group in which part or all of the hydrogen atoms within the aforementioned alkyl group have been substituted with the aforementioned halogen atoms.

With respect to —COOR" and —OC(=O)R" as the substituent for the aforementioned aromatic hydrocarbon group, R" is the same as defined for R" in the aforementioned structural unit (a2).

Examples of the hydroxyalkyl group as the substituent for the aforementioned aromatic hydrocarbon group include groups in which at least one hydrogen atom of the aforementioned alkyl group as the substituent has been substituted with a hydroxy group.

The aromatic hydrocarbon group represented by Z is preferably an aryl group which may have a substituent, an arylalkyl group or a heteroaryl group.

As the aryl group, an unsubstituted aryl group or an aryl group having a halogen atom as a substituent (halogenated aryl group) is preferable, and a phenyl group, a naphthyl group or a fluorinated phenyl group is particularly desirable.

As the arylalkyl group, a group in which the alkyl group is a methyl group is preferable, and a naphthylmethyl group or a benzyl group is more preferable.

As the heteroaryl group, a group containing a nitrogen atom as the hetero atom is preferable, and a group in which one hydrogen atom has been removed from pyridine is particularly desirable.

The aliphatic hydrocarbon group for Z may be a saturated aliphatic hydrocarbon group, an unsaturated aliphatic hydrocarbon group or a combination thereof. Further, the aliphatic hydrocarbon group may be linear, branched or cyclic.

In the aliphatic hydrocarbon group for Z, part of the carbon atoms constituting the aliphatic hydrocarbon group may be substituted with a substituent group containing a hetero atom, or part or all of the hydrogen atoms constituting the aliphatic hydrocarbon group may be substituted with a substituent group containing a hetero atom.

As the "hetero atom" for Z, there is no particular limitation as long as it is an atom other than carbon and hydrogen. Examples of hetero atoms include a halogen atom, an oxygen atom, a sulfur atom and a nitrogen atom. Examples of the halogen atom include a fluorine atom, a chlorine atom, an iodine atom and a bromine atom.

The substituent group containing a hetero atom may consist of a hetero atom, or may be a group containing a group or atom other than a hetero atom.

Specific examples of the substituent group for substituting part of the carbon atoms include —O—, —C(=O)—O—, —C(=O)—, —O—C(=O)—O—, —C(=O)—NH—, —NH— (the H may be replaced with a substituent such as an alkyl group or an acyl group), —S—, —S(=O)$_2$— and —S(=O)$_2$—O—. When the aliphatic hydrocarbon group is cyclic, the aliphatic hydrocarbon group may contain any of these substituent groups in the ring structure.

Examples of the substituent group for substituting part or all of the hydrogen atoms include an alkoxy group, a halogen atom, a halogenated alkyl group, a hydroxyl group, an oxygen atom (=O) and a cyano group.

The aforementioned alkoxy group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Example of the aforementioned halogenated alkyl group includes a group in which part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

As the aliphatic hydrocarbon group, a linear or branched saturated hydrocarbon group, a linear or branched monovalent unsaturated hydrocarbon group, a cyclic aliphatic hydrocarbon group (aliphatic cyclic group) or a combination thereof is preferable.

The linear saturated hydrocarbon group (alkyl group) preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decanyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 2 to 10 carbon atoms, more preferably 2 to 5, still more preferably 2 to 4, and most preferably 3. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30, still more preferably 5 to 20, still more preferably 6 to 15, and most preferably 6 to 12.

As the aliphatic cyclic group, a group in which one or more hydrogen atoms have been removed from a monocycloalkane or a polycycloalkane such as a bicycloalkane, tricycloalkane or tetracycloalkane can be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and a group in which one or more hydrogen atoms have been removed from adamantane is particularly desirable.

When the aliphatic cyclic group contains a hetero atom-containing substituent group in the ring structure thereof, the hetero atom-containing substituent group is preferably —O—, —C(=O)—O—, —S—, —S(=O)$_2$— or —S(=O)$_2$—O—. Specific examples of such aliphatic cyclic groups include groups represented by formulas (L1) to (L5) and (S1) to (S4) shown below.

[Chemical Formula 48]

(L1)

(L2)

(L3)

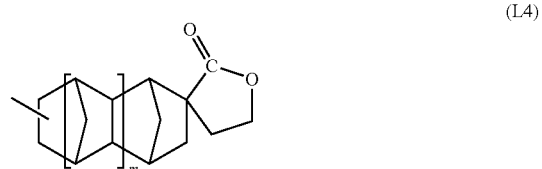

(L4)

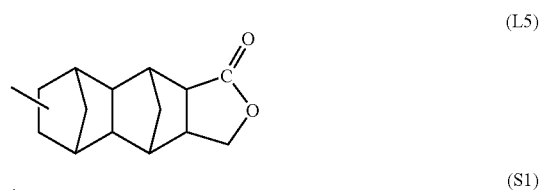

(L5)

(S1)

(S2)

(S3)

(S4)

In the formula, Q" represents an alkylene group of 1 to 5 carbon atoms, —O—, —S—, or —S—$R^{95}$— (wherein each of $R^{94}$ and $R^{95}$ independently represents an alkylene group of 1 to 5 carbon atoms); and m represents 0 or 1.

As the alkylene group for Q", $R^{94}$ and $R^{95}$, the same alkylene groups as those described above for $R^{91}$ to $R^{93}$ can be used.

In these aliphatic cyclic groups, part of the hydrogen atoms bonded to the carbon atoms constituting the ring structure may be substituted with a substituent. Examples of substituents include an alkyl group, an alkoxy group, a halogen atom, a halogenated alkyl group, a hydroxyl group and an oxygen atom (=O).

As the alkyl group, an alkyl group of 1 to 5 carbon atoms is preferable, and a methyl group, an ethyl group, a propyl group, an n-butyl group or a tert-butyl group is particularly desirable.

As the alkoxy group and the halogen atom, the same groups as the substituent groups for substituting part or all of the hydrogen atoms can be used.

In the present invention, Z preferably represents a group containing a cyclic group which may have a substituent. The cyclic group may be either an aromatic hydrocarbon group which may have a substituent, or an aliphatic cyclic group which may have a substituent, and an aliphatic cyclic group which may have a substituent is preferable.

As the aromatic hydrocarbon group, a naphthyl group which may have a substituent, or a phenyl group which may have a substituent is preferable.

As the aliphatic cyclic group which may have a substituent, an aliphatic polycyclic group which may have a substituent is preferable. As the aliphatic polycyclic group, the aforementioned group in which one or more hydrogen atoms have been removed from a polycycloalkane, and groups represented by formulas (L2) to (L5), (S3) and (S4) are preferable.

In the present invention, $R^{4\prime\prime\prime}$ preferably has Z-$Q^1$- as a substituent. In such a case, $R^{4\prime\prime\prime}$ is preferably a group represented by the formula Z-$Q^1$-$Y^1$— (in the formula, $Q^1$ and Z are the same as defined above; and $Y^1$ represents an alkylene group of 1 to 4 carbon atoms which may have a substituent, or a fluorinated alkylene group of 1 to 4 carbon atoms which may have a substituent).

That is, X" is preferably an anion represented by general formula (x-11) shown below.

[Chemical Formula 49]

Z-$Q^1$-$Y^1$—$SO_3^-$ (x-11)

In the formula, $Q^1$ represents a divalent linking group containing an oxygen atom; Z represents a hydrocarbon group of 3 to 30 carbon atoms which may have a substituent; and $Y^1$ represents an alkylene group of 1 to 4 carbon atoms which may have a substituent or a fluorinated alkylene group of 1 to 4 carbon atoms which may have a substituent.

In formula (x-11), Z and $Q^1$ are the same as defined above.

As the alkylene group for $Y^1$, the same alkylene groups as those described above for $Q^1$ which have 1 to 4 carbon atoms can be mentioned.

As the fluorinated alkylene group, the aforementioned alkylene group in which part or all of the hydrogen atoms has been substituted with fluorine atoms can be used.

Specific examples of $Y^1$ include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—; —$CHF$—, —$CH_2CF_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, —$C(CF_3)_2CH_2$—; —$CH_2$—, —$CH_2CH_2$—, —$CH_2CH_2CH_2$—, —$CH(CH_3)CH_2$—, —$CH(CH_2CH_3)$—, —$C(CH_3)_2$—, —$CH_2CH_2CH_2CH_2$—, —$CH(CH_3)CH_2CH_2$—, —$CH_2CH(CH_3)CH_2$—, —$CH(CH_3)CH(CH_3)$—, —$C(CH_3)_2CH_2$—, —$CH(CH_2CH_3)CH_2$—, —$CH(CH_2CH_2CH_3)$—, and —$C(CH_3)(CH_2CH_3)$—.

$Y^1$ is preferably a fluorinated alkylene group, and particularly preferably a fluorinated alkylene group in which the carbon atom bonded to the adjacent sulfur atom is fluorinated. Examples of such fluorinated alkylene groups include —$CF_2$—, —$CF_2CF_2$—, —$CF_2CF_2CF_2$—, —$CF(CF_3)CF_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—; —$CH_2CF_2$—, —$CH_2CH_2CF_2$—, —$CH_2CF_2CF_2$—; —$CH_2CH_2CH_2CF_2$—, —$CH_2CH_2CF_2CF_2$—, and —$CH_2CF_2CF_2CF_2$—.

Of these, —$CF_2$—, —$CF_2CF_2$—, —$CF_2CF_2CF_2$— or $CH_2CF_2CF_2$— is preferable, —$CF_2$—, —$CF_2CF_2$— or —$CF_2CF_2CF_2$— is more preferable, and —$CF_2$— is particularly desirable.

The alkylene group or fluorinated alkylene group may have a substituent. The alkylene group or fluorinated alkylene group "has a substituent" means that part or all of the hydrogen atoms or fluorine atoms in the alkylene group or fluorinated alkylene group has been substituted with groups other than hydrogen atoms and fluorine atoms.

Examples of substituents which the alkylene group or fluorinated alkylene group may have include an alkyl group of 1 to 4 carbon atoms, an alkoxy group of 1 to 4 carbon atoms, and a hydroxyl group.

As a preferable example of the anion represented by general formula (x-11), an anion represented by general formula (x-11-1) shown below can be given.

[Chemical Formula 50]

$$Z \left[ \left( \underset{\underset{O}{\overset{O}{\|}}}{C} \right)_{m1} O \right]_{m2} Q^2 \left[ O \left( \underset{\underset{O}{\overset{O}{\|}}}{C} \right)_{m3} \right]_{m4} (CF_2)_p SO_3^-$$ (x-11-1)

In the formula, Z is the same as defined above; $Q^2$ represents a single bond or an alkylene group; p represents an integer of 1 to 3; and each of m1 to m4 independently represents 0 or 1, provided that m2+m3 is 1 or 2.

In formula (x-11-1), p represents an integer of 1 to 3, preferably 1 or 2.

As the alkylene group for $Q^2$, the same alkylene groups as those described above for $R^{91}$ to $R^{93}$ in the explanation of $Q^1$ can be mentioned.

Each of m1 to m4 represents 0 or 1, provided that m2+m3 is 1 or 2.

Specific examples of the anion represented by formula (x-11-1) include an anion represented by general formula (x-11-10) shown below, an anion represented by general formula (x-11-20) shown below, an anion represented by general formula (x-11-30) shown below and an anion represented by general formula (x-11-40) shown below.

Anion Represented by General Formula (x-11-10)

[Chemical Formula 51]

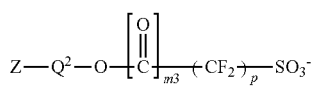
(x-11-10)

In formula (x-11-10), Z, $Q^2$, m3 and p are the same as defined above.

In formula (x-11-10), as Z, an aliphatic cyclic group which may have a substituent, a linear aliphatic hydrocarbon group which may have a substituent, or an aromatic hydrocarbon group which may have a substituent is preferable. Of these, an aliphatic cyclic group which contains a hetero atom-containing substituent in the ring structure thereof is more preferable As $Q^2$, a single bond or a methylene group is particularly desirable. Especially, when Z is an aliphatic cyclic group which may have a substituent, $Q^2$ is preferably a single bond. On the other hand, when Z is an aromatic hydrocarbon group, $Q^2$ is preferably a methylene group.

Specific examples of preferable anions represented by general formula (x-11-10) are shown below.

[Chemical Formula 52]

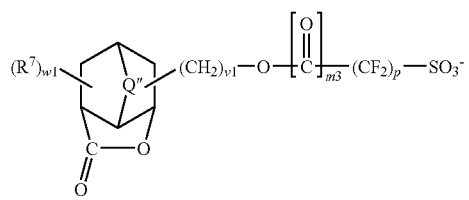
(x-11-11)

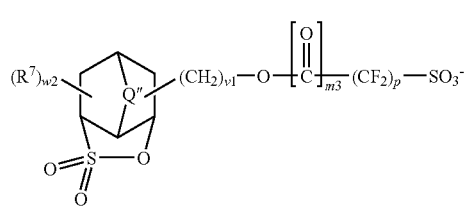
(x-11-12)

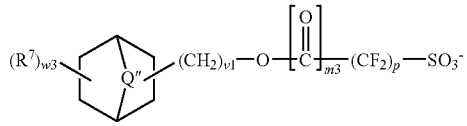
(x-11-13)

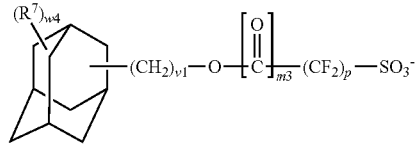
(x-11-14)

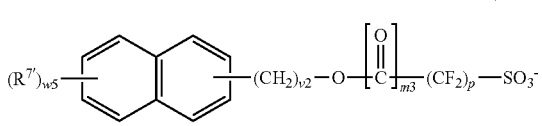
(x-11-15)

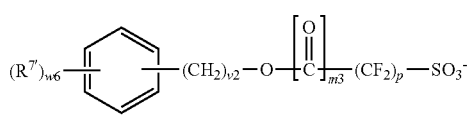
(x-11-16)

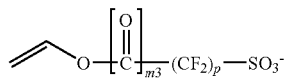
(x-11-17)

In the formulas, Q", m3 and p are the same as defined above; each of $R^7$ and $R^{7'}$ independently represents a substituent; each of w1 to w6 independently represents an integer of 0 to 3; and each of v1 and v2 independently represents an integer of 0 to 5.

In the formulas, as the substituent for $R^7$, the same substituents as those which an aliphatic hydrocarbon group for Z may have can be mentioned.

In the formulas, as the substituent for $R^{7'}$, the same substituents as those which an aromatic hydrocarbon group for Z may have can be mentioned.

If there are two or more of an individual $R^7$ and $R^{7'}$ group, as indicated by the corresponding value of w1 to w6, then two or more of the individual $R^7$ and $R^{7'}$ group may be the same or different from each other.

It is preferable that each of w1 to w6 independently represents an integer of 0 to 2, and most preferably 0.

It is preferable that each of v1 and v2 independently represents an integer of 0 to 3, most preferably 0.

Anion Represented by General Formula (x-11-20)

[Chemical Formula 53]

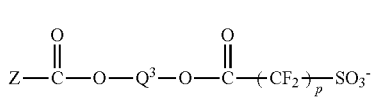
(x-11-20)

In formula (x-11-20), Z and p are the same as defined above; and $Q^3$ represents an alkylene group.

In formula (x-11-20), as Z, an aliphatic cyclic group which may have a substituent, a linear aliphatic hydrocarbon group which may have a substituent, or an aromatic hydrocarbon group which may have a substituent is preferable.

As the alkylene group for $Q^3$, the same alkylene groups as those described above for $R^{91}$ to $R^{93}$ in the explanation of $Q^1$ can be mentioned.

Specific examples of preferable anions represented by general formula (x-11-20) are shown below.

[Chemical Formula 54]

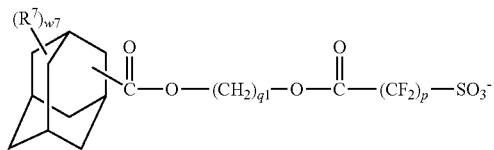
(x-11-21)

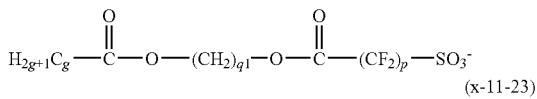
(x-11-22)

(x-11-23)

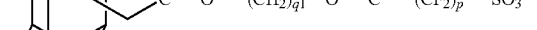
(x-11-24)

In the formulas, p, $R^7$ and $R^{7'}$ are the same as defined above; each of w7 to w9 independently represents an integer of 0 to 3; q1 represents an integer of 1 to 12; and g represents an integer of 1 to 20.

If there are two or more of an individual $R^7$ and $R^{7'}$ group, as indicated by the corresponding value of w7 to w9, then two or more of the individual $R^7$ and $R^{7'}$ group may be the same or different from each other.

It is preferable that each of w7 to w9 independently represent an integer of 0 to 2, more preferably 0 or 1, and still more preferably 0.

q1 is preferably 1 to 8, more preferably 1 to 5, and still more preferably 1 to 3.

g is preferably 1 to 15, and more preferably 1 to 10.

p is preferably 1 or 2, and most preferably 1.

Anion Represented by General Formula (x-11-30)

[Chemical Formula 55]

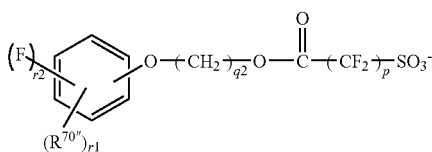
(x-11-30)

In formula (x-11-30), p is the same as defined above; q2 represents an integer of 0 to 5; $R^{70''}$ represents an alkyl group, an alkoxy group, a halogen atom (excluding fluorine), a halogenated alkyl group, a hydroxy group, an oxygen atom (=O), —COOR'', —OC(=O)R'', a hydroxyalkyl group or a cyano group; r1 represents an integer of 0 to 2, and r2 represents an integer of 1 to 5, provided that $1 \leq r1+r2 < 5$.

In formula (x-11-30), q2 is preferably 1 to 4, more preferably 1 or 2, and most preferably 2.

Examples of the alkyl group, alkoxy group, halogen atom (excluding fluorine), halogenated alkyl group, —COOR'', —OC(=O)R'' and hydroxyalkyl group for $R^{70''}$ include the same groups as those described above for the substituent which the aromatic hydrocarbon group represented by Z may have.

r1 is most preferably 0.

r2 is preferably 2 to 5, and most preferably 5.

Anion Represented by General Formula (x-11-40)

[Chemical Formula 56]

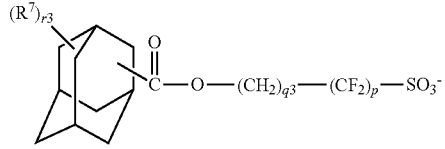
(x-11-40)

In formula (x-11-40), p and $R^7$ are the same as defined above; q3 represents an integer of 1 to 12; and r3 represents an integer of 0 to 3.

In formula (x-11-40), as $R^7$, an alkyl group, an alkoxy group, a halogen atom, a halogenated alkyl group, a hydroxy group, an oxygen atom (=O) or a cyano group is preferable.

As the alkyl group, an alkyl group of 1 to 5 carbon atoms is preferable, and a methyl group, an ethyl group, a propyl group, an n-butyl group or a tert-butyl group is particularly desirable.

The aforementioned alkoxy group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Example of the aforementioned halogenated alkyl group includes a group in which part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

If there are two or more of the $R^7$ group, as indicated by the value r3, then the two or more of the $R^7$ groups may be the same or different from each other.

p is preferably 1 or 2, and most preferably 1.

q3 is preferably 1 to 5, more preferably 1 to 3, and most preferably 1.

r3 is preferably an integer of 0 to 2, more preferably 0 or 1, and still more preferably 0.

Further, as $R^{4''}$, a group which has an oxygen atom (=O) as a substituent is also preferable. In such a case, $R^{4''}$ is preferably a group represented by the formula $R^{10''}$—$(CH_2)_{n''}$— (in the formula, $R^{10''}$ represents a cyclic alkyl group of 4 to 20 carbon atoms which has an oxygen atom (=O) as a substituent; and n'' represents 0 or 1).

The expression "has an oxygen atom as a substituent" means that two hydrogen atoms bonded to a carbon atom constituting the cyclic alkyl group of 4 to 20 carbon atoms are substituted with an oxygen atom (=O).

The cyclic alkyl group represented by $R^{10''}$ is not particularly limited as long as it has 4 to 20 carbon atoms, and may be either polycyclic or monocyclic. Examples thereof include a group in which one hydrogen atom has been removed from a monocycloalkane or a polycycloalkane such as a bicycloalkane, tricycloalkane or tetracycloalkane. As the monocyclic group, a group in which one hydrogen atom has been removed from a monocycloalkane of 3 to 8 carbon atoms is preferable, and specific examples thereof include a cyclopentyl group, a cyclohexyl group, a cycloheptyl group and a cyclooctyl group. The polycyclic group preferably has 7 to 12 carbon atoms, and specific examples thereof include an adamantyl group, a norbornyl group, an isobornyl group, a tricyclodecanyl group and a tetracyclododecanyl group.

As $R^{10''}$, a polycyclic alkyl group of 4 to 20 carbon atoms that has an oxygen atom (=O) as a substituent is preferable. From an industrial viewpoint, a group in which two hydrogen atoms bonded to a carbon atom constituting an adamantyl group, a norbornyl group or a tetracyclododecyl group are substituted with an oxygen atom (=O) is preferable, and a norbornyl group having an oxygen atom (=O) as a substituent is particularly desirable.

The alkyl group for $R^{10''}$ may have a substituent other than oxygen. As an example of such a substituent, a lower alkyl group of 1 to 5 carbon atoms can be given.

In the formula: $R^{10''}$—$(CH_2)_{n''}$—, n" represents 0 or 1, and preferably 1.

When $R^{4''}$ is a group represented by the formula $R^{10''}$—$(CH_2)_{n''}$—, $X^-$ is preferably a camphorsulfonate ion (an ion in which one hydrogen within camphor has been substituted with —$SO_3^-$, and an ion represented by chemical formula (x-12-1) (a group in which a sulfonate ion (—$SO_3^-$) is bonded to the carbon atom of a methyl group bonded to the first position of the norbornane ring) is particularly desirable.

[Chemical Formula 57]

(x-12-1)

Further examples of anions other than those described above which are usable as $X^-$ include anions represented by general formula (b-3) or (b-4) shown below.

[Chemical Formula 58]

In the formulas, X" represents an alkylene group of 2 to 6 carbon atoms in which at least one hydrogen atom has been substituted with a fluorine atom; and each of Y" and Z" independently represents an alkyl group which may have a substituent or a halogenated alkyl group which may have a substituent. The —$SO_2$— group bonded to Z" may be substituted with —C(=O)—.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

The smaller the number of carbon atoms of the alkylene group for X" within the above-mentioned range of the number of carbon atoms, the more the solubility in a resist solvent is improved.

Further, in the alkylene group for X", it is preferable that the number of hydrogen atoms substituted with fluorine atoms is as large as possible because the acid strength increases and the transparency to high energy radiation of 200 nm or less or electron beam is improved. The fluorination ratio of the alkylene group or alkyl group is preferably from 70 to 100%, more preferably from 90 to 100%, and it is particularly desirable that the alkylene group or alkyl group be a perfluoroalkylene group or perfluoroalkyl group in which all hydrogen atoms are substituted with fluorine atoms.

The alkyl group for Y" and Z" may be linear, branched or cyclic, and examples thereof include the same alkyl groups as those described above for $R^{4''}$.

As the halogenated alkyl group for Y" and Z", a group in which part of or all of the hydrogen atoms of an alkyl group have been substituted with halogen atoms can be mentioned, and examples thereof include the same halogenated alkyl groups as those described above for $R^{4''}$.

In the halogenated alkyl group, the percentage of the number of halogen atoms based on the total number of halogen atoms and hydrogen atoms (halogenation ratio (%)) is preferably 10 to 100%, more preferably 50 to 100%, and most preferably 100%. Higher halogenation ratio is preferable because the acid strength increases.

As the halogenated alkyl group, a fluorinated alkyl group is particularly desirable.

The alkyl group or the halogenated alkyl group for Y" and Z" may have a substituent.

The alkyl group for Y" and Z" "may have a substituent" means that part or all of the hydrogen atoms within the aforementioned alkyl group may be substituted with a substituent. The halogenated alkyl group for Y" and Z" "may have a substituent" means that part or all of the hydrogen atoms within the aforementioned halogenated alkyl group may be substituted with a substituent. Y" and Z" may have one substituent, or two or more substituents.

The substituent for the alkyl group or the halogenated alkyl group represented by Y" or Z" may be any atom or group other than carbon, hydrogen and halogen, and examples thereof include a hetero atom, an alkyl group and a group represented by the formula: $Z^5$-$Q^4$- (in the formula, $Q^4$ represents a divalent linking group containing an oxygen atom, and $Z^5$ represents a hydrocarbon group of 3 to 30 carbon atoms which may have a substituent).

Among these substituents, as the hetero atom and the alkyl group, the same hetero atom and alkyl group as those described above as a substituent for $R^{4''}$ can be given, respectively.

In the group represented by the formula $Z^5$-$Q^4$-, $Q^4$ represents a divalent linking group containing an oxygen atom.

Examples of $Q^4$ include the same groups as those described above for $Q^1$ in the group represented by the formula Z-$Q^1$-.

$Q^4$ is preferably a divalent linking group containing an ester bond and/or ether bond, and more preferably a group of —O—, —$R^{91}$—O—, —$R^{92}$—O—C(=O)—, —C(=O)—O—, —C(=O)—O—$R^{93}$—, or —C(=O)—O—$R^{93}$—O—C(=O)—. $R^{91}$ to $R^{93}$ are the same as defined above.

In the group represented by the formula $Z^5$-$Q^4$-, $Z^5$ represents a hydrocarbon group of 3 to 30 carbon atoms which may have a substituent.

Examples of $Z^5$ include the same groups as those described above for Z in the group represented by the formula Z-$Q^1$-.

As $Z^5$, an aliphatic hydrocarbon group is preferable, a linear or cyclic aliphatic hydrocarbon group is more preferable, and a cyclic aliphatic hydrocarbon group is still more preferable.

In formula (b-4), the —SO$_2$— group bonded to Z" may be substituted with —C(=O)—. That is, the anion moiety represented by the formula (b-4) may be represented by general formula (b-4') shown below.

[Chemical Formula 59]

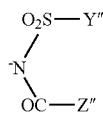

(b-4')

In the formula, Y" and Z" are the same as defined above.

In the present invention, in the formulas (b-4) and (b-4'), it is preferable that at least one of Y" and Z" is a fluorinated alkyl group which may have a substituent.

In formula (b-4), it is particularly desirable that at least one of Y" and Z" is a perfluoroalkyl group, and the other represents an alkyl group which may have a substituent or a fluorinated alkyl group which may have a substituent. In the formula (b-4'), it is preferable that at least one of Y" and Z" is a perfluoroalkyl group, and the other is an alkyl group which may have a substituent. It is particularly desirable that Y" represents a perfluoroalkyl group, and Z" represents an alkyl group which may have a substituent.

Examples of the anion represented by the formula (b-4) or (b-4') in such a case include anions represented by formulas (b-4-1) to (b-4-8) shown below.

[Chemical Formula 60]

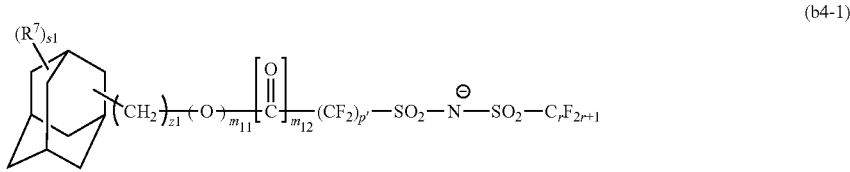
(b4-1)

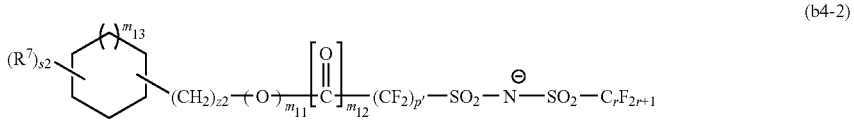
(b4-2)

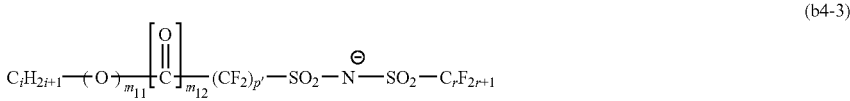
(b4-3)

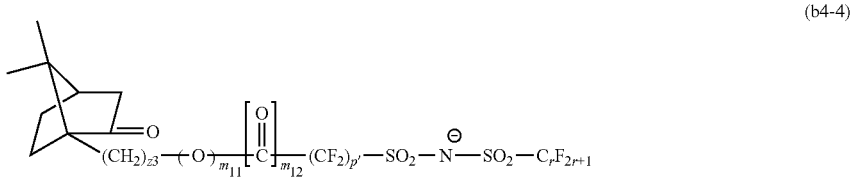
(b4-4)

[Chemical Formula 61]

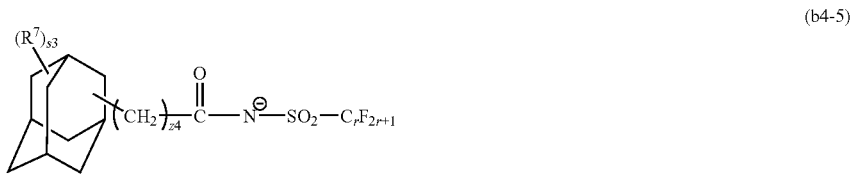
(b4-5)

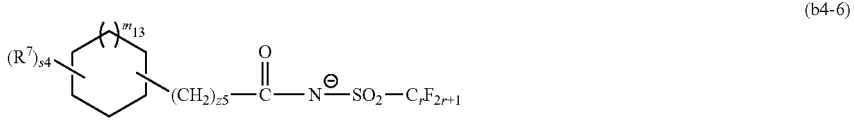
(b4-6)

(b4-7)

(b4-8)

In the formulas, $R^7$ represents a substituent; each of s1 to s4 independently represents an integer of 0 to 3; each of z1 to z6 independently represents an integer of 0 to 3; p' represents an integer of 0 to 4; each of $m_{11}$ to $m_{13}$ independently represents 0 or 1; r represents an integer of 1 to 4; and i represents an integer of 1 to 20.

In the formulas, as the substituent for $R^7$, the same substituents as those which an aliphatic hydrocarbon group for Z in the group represented by the formula $Z-Q^1$- may have can be mentioned.

If there are two or more of the $R^7$ group, as indicated by the values s1 to s4, then the two or more of the $R^7$ groups may be the same or different from each other.

s1 to s4 is preferably 0 or 1, and most preferably 0.
z1 to z6 is preferably 0 or 1.
p' is preferably 0 to 2.
$m_{12}$ is preferably 0.
r is preferably 1 or 2, and most preferably 1.
i is preferably 1 to 15, more preferably 3 to 12.

In the present invention, anions represented by formulas (b-4-1) to (b-4-4) are particularly desirable.

In addition, further examples of anions other than those described above which are usable as $X^-$ include methide anions. Examples of the methide anion include an anion represented by general formula (b-c1) shown below.

[Chemical Formula 62]

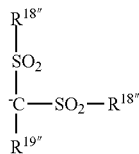

(b-c1)

In the formula, $R^{18''}$ represents an alkyl group of 1 to 10 carbon atoms in which at least one hydrogen atom has been substituted with a fluorine atom; and $R^{19''}$ represents $-SO_2-R^{18''}$ or a hydrocarbon group which may have a substituent.

In general formula (b-c1), $R^{18''}$ represents an alkyl group of 1 to 10 carbon atoms in which at least one hydrogen atom has been substituted with a fluorine atom. The alkyl group may be any of linear, branched or cyclic. In the present invention, as $R^{18''}$, a linear or branched alkyl group is preferable, and a linear alkyl group is more preferable.

In general formula (b-c1), when $R^{19''}$ represents a hydrocarbon group which may have a substituent (herein, "a hydrocarbon group which may have a substituent" means that part or all of the hydrogen atoms constituting the hydrocarbon group may be substituted with a substituent), the hydrocarbon group for $R^{19''}$ may be either an aliphatic hydrocarbon group or an aromatic hydrocarbon group. Specifically, the same groups as those described above for Z in the aforementioned formula: $Z-Q^1$- can be mentioned.

As $R^{19''}$, an aryl group which has a halogen atom as a substituent (halogenated aryl group) or $-SO_2-R^{18''}$ is preferable. Examples of the aryl group within the halogenated aryl group include groups in which part or all of the hydrogen atoms within an aryl group of 6 to 10 carbon atoms such as a phenyl group or a naphthyl group has been substituted with a halogen atom. As the halogen atom within the halogenated aryl group, a fluorine atom is preferable.

Among the aforementioned examples, as $X^-$, an anion represented by general formula (x-1) is preferable.

Among the anions represented by general formula (x-1), a group in which $R^{4''}$ in formula (x-1) represents a fluorinated alkyl group which may have a substituent, i.e., a fluorinated alkylsulfonate ion which may have a substituent is preferable.

Further, as the anion represented by formula (x-1), an anion represented by general formula (x-11) is preferable, and an anion in which $Y^1$ in formula (x-11) represents a fluorinated alkylene group of 1 to 4 carbon atoms is particularly desirable.

Moreover, as $X^-$, an anion represented by general formula (b-3) or (b-4), or an anion represented by general formula (x-12-1) is also preferable.

As the component (B1), one type of acid generator may be used alone, or two or more types may be used in combination.

In the component (B), the amount of the component (B1) may be 100% by weight. When the component (B1) is used in combination with an acid-generator component that does not fall under the category of the component (B1), the amount of the component (B1) is preferably in the range of 1 to 99% by weight, more preferably 10 to 99% by weight, still more preferably 20 to 90% by weight, and most preferably 40 to 85% by weight.

Furthermore, the total amount of the component (B1) within the resist composition of the present invention, relative to 100 parts by weight of the component (A) is preferably 0.1 to 60 parts by weight, and more preferably 1 to 40 parts by weight. When the amount is at least as large as the lower limit of the above-mentioned range, defects can be reduced, and a resist pattern having an excellent shape can be formed. On the other hand, when the amount is no more than the upper limit of the above-mentioned range, a uniform solution can be obtained and the storage stability becomes satisfactory.

The resist composition of the present invention may also contain, as the component (B), an acid-generator component other than the aforementioned component (B1) (hereafter, referred to as "component (B2)").

As the component (B2), there is no particular limitation, and any of the known acid generators used in conventional chemically amplified resist compositions can be used. Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators.

As an onium salt acid generator, a compound represented by general formula (b-1) or (b-2) shown below can be used.

[Chemical Formula 63]

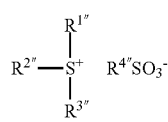

(b-1)

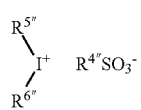

(b-2)

In the formulas, each of $R^{1''}$ to $R^{3''}$, $R^{5''}$ and $R^{6''}$ independently represents an aryl group or an alkyl group; in formula (b-1), two of $R^{1''}$ to $R^{3''}$ may be bonded to each other to form a ring with the sulfur atom; at least one of $R^{1''}$ to $R^{3''}$ represents an aryl group, and at least one of $R^{5\prime\prime\prime}$ and $R^{6\prime\prime\prime}$ represents an aryl group; and $R^{4\prime\prime\prime}$ is the same as defined above.

In formula (b-1), $R^{1\prime\prime\prime}$ to $R^{3\prime\prime\prime}$ each independently represents an aryl group or an alkyl group. In formula (b-1), two of $R^{1\prime\prime\prime}$ to $R^{3\prime\prime\prime}$ may be bonded to each other to form a ring with the sulfur atom.

Further, among $R^{1\prime\prime\prime}$ to $R^{3\prime\prime\prime}$, at least one group represents an aryl group. Among $R^{1\prime\prime\prime}$ to $R^{3\prime\prime\prime}$, two or more groups are preferably aryl groups, and it is particularly desirable that all of $R^{1\prime\prime\prime}$ to $R^{3\prime\prime\prime}$ are aryl groups.

The aryl group for $R^{1\prime\prime\prime}$ to $R^{3\prime\prime\prime}$ is not particularly limited. For example, an aryl group having 6 to 20 carbon atoms may be used in which part or all of the hydrogen atoms of the aryl group may or may not be substituted with an alkyl group, an alkoxy group, an ether group, a halogen atom, a halogenated alkyl group or a hydroxyl group. The aryl group is preferably an aryl group having 6 to 10 carbon atoms because it can be synthesized at a low cost. Specific examples thereof include a phenyl group and a naphthyl group.

As the alkyl group, the ether group, the halogen atom and the halogenated alkyl group that may substitute the hydrogen atom(s) within the aforementioned aryl group, the same alkyl group, ether group, halogen atom and halogenated alkyl group as those described above as substituents for the aforementioned aryl group for $R^{7\prime\prime\prime}$ to $R^{9\prime\prime\prime}$ can be mentioned.

The alkyl group for $R^{1\prime\prime\prime}$ to $R^{3\prime\prime\prime}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group, and a methyl group is most preferable because it is excellent in resolution and can be synthesized at a low cost.

It is particularly desirable that each of $R^{1\prime\prime\prime}$ to $R^{3\prime\prime\prime}$ independently represent a phenyl group or a naphthyl group.

When two of $R^{1\prime\prime\prime}$ to $R^{3\prime\prime\prime}$ in formula (b-1) are bonded to each other to form a ring with the sulfur atom, it is preferable that the two of $R^{1\prime\prime\prime}$ to $R^{3\prime\prime\prime}$ form a 3 to 10-membered ring including the sulfur atom, and it is particularly desirable that the two of $R^{1\prime\prime\prime}$ to $R^{3\prime\prime\prime}$ form a 5 to 7-membered ring including the sulfur atom.

When two of $R^{1\prime\prime\prime}$ to $R^{3\prime\prime\prime}$ in formula (b-1) are bonded to each other to form a ring with the sulfur atom, the remaining one of $R^{1\prime\prime\prime}$ to $R^{3\prime\prime\prime}$ is preferably an aryl group. As examples of the aryl group, the same as the above-mentioned aryl groups for $R^{1\prime\prime\prime}$ to $R^{3\prime\prime\prime}$ can be given.

In formula (b-2), $R^{5\prime\prime\prime}$ and $R^{6\prime\prime\prime}$ each independently represent an aryl group or alkyl group. At least one of $R^{5\prime\prime\prime}$ and $R^{6\prime\prime\prime}$ represents an aryl group. It is preferable that both of $R^{5\prime\prime\prime}$ and $R^{6\prime\prime\prime}$ represent an aryl group.

As the aryl group for $R^{5\prime\prime\prime}$ and $R^{6\prime\prime\prime}$, the same as the aryl groups for $R^{1\prime\prime\prime}$ to $R^{3\prime\prime\prime}$ can be used.

As the alkyl group for $R^{5\prime\prime\prime}$ and $R^{6\prime\prime\prime}$, the same as the alkyl groups for $R^{1\prime\prime\prime}$ to $R^{3\prime\prime\prime}$ can be used.

It is particularly desirable that both of $R^{5\prime\prime\prime}$ and $R^{6\prime\prime\prime}$ represents a phenyl group.

As $R^{4\prime\prime\prime}$ in formula (b-2), the same groups as those mentioned above for $R^{4\prime\prime\prime}$ in formula (b-1) can be used.

Specific examples of suitable onium salt acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts are replaced by methanesulfonate, n-propanesulfonate, n-butanesulfonate, or n-octanesulfonate.

Further, onium salt-based acid generators in which the anion moiety in general formula (b-1) or (b-2) is replaced by an anion moiety represented by general formula (b-3) or (b-4) (the cation moiety is the same as (b-1) or (b-2)) may also be used.

Furthermore, as an onium salt-based acid generator, a sulfonium salt having a cation moiety represented by general formula (b-5) or (b-6) shown below may be used.

[Chemical Formula 64]

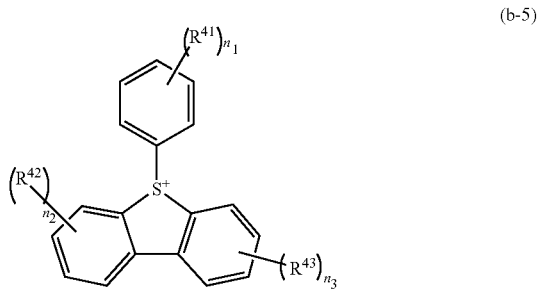

(b-5)

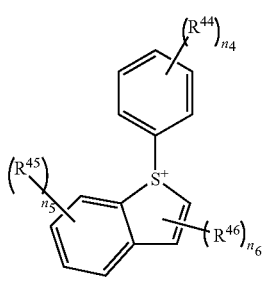

(b-6)

In formulas (b-5) and (b-6) above, each of $R^{41}$ to $R^{46}$ independently represents an alkyl group, an acetyl group, an alkoxy group, a carboxy group, a hydroxyl group or a hydroxyalkyl group; each of $n_1$ to $n_5$ independently represents an integer of 0 to 3; and $n_6$ represents an integer of 0 to 2.

With respect to $R^{41}$ to $R^{46}$, the alkyl group is preferably an alkyl group of 1 to 5 carbon atoms, more preferably a linear or branched alkyl group, and most preferably a methyl group, ethyl group, propyl group, isopropyl group, n-butyl group or tert-butyl group.

The alkoxy group is preferably an alkoxy group of 1 to 5 carbon atoms, more preferably a linear or branched alkoxy group, and most preferably a methoxy group or ethoxy group.

The hydroxyalkyl group is preferably the aforementioned alkyl group in which one or more hydrogen atoms have been substituted with hydroxy groups, and examples thereof include a hydroxymethyl group, a hydroxyethyl group and a hydroxypropyl group.

If there are two or more of an individual $R^{41}$ to $R^{46}$ group, as indicated by the corresponding value of $n_1$ to $n_6$, then the two or more of the individual $R^{41}$ to $R^{46}$ group may be the same or different from each other.

$n_1$ is preferably 0 to 2, more preferably 0 or 1, and still more preferably 0.

It is preferable that $n_2$ and $n_3$ each independently represent 0 or 1, and more preferably 0.

$n_4$ is preferably 0 to 2, and more preferably 0 or 1.

$n_5$ is preferably 0 or 1, and more preferably 0.

$n_6$ is preferably 0 or 1, and more preferably 1.

The anion moiety of the sulfonium salt having a cation moiety represented by general formula (b-5) or (b-6) is not particularly limited, and the same anion moieties for onium salt-based acid generators which have been proposed may be used. Examples of such anion moieties include fluorinated alkylsulfonic acid ions such as anion moieties ($R^{4''}SO_3^-$) for onium salt-based acid generators represented by general formula (b-1) or (b-2) shown above; and anion moieties represented by general formula (b-3) or (b-4) shown above. Among these, a fluorinated alkylsulfonate ion is preferable, a fluorinated alkylsulfonate ion of 1 to 4 carbon atoms is more preferable, and a linear perfluoroalkylsulfonate ion of 1 to 4 carbon atoms is particularly desirable. Specific examples thereof include a trifluoromethylsulfonate ion, a heptafluoro-n-propanesulfonate ion and a nonafluoro-n-butanesulfonate ion.

In the present description, an oximesulfonate-based acid generator is a compound having at least one group represented by general formula (B-1) shown below, and has a feature of generating acid by irradiation. Such oxime-sulfonate acid generators are widely used for a chemically amplified resist composition, and can be appropriately selected.

[Chemical Formula 65]

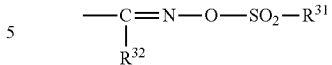

(B-1)

In the formula, each of $R^{31}$ and $R^{32}$ independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The alkyl group or the aryl group "has a substituent" means that part or all of the hydrogen atoms of the alkyl group or the aryl group is substituted with a substituent.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which part of the hydrogen atoms are substituted with halogen atoms and the "completely halogenated alkyl group" refers to an alkyl group in which all of the hydrogen atoms are substituted with halogen atoms. Examples of halogen atoms include fluorine atoms, chlorine atoms, bromine atoms and iodine atoms, and fluorine atoms are particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. Examples of the alkyl group and the aryl group for $R^{32}$ include the same alkyl groups and aryl groups as those described above for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate acid generator include compounds represented by general formula (B-2) or (B-3) shown below.

[Chemical Formula 66]

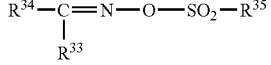

(B-2)

In the formula, $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 67]

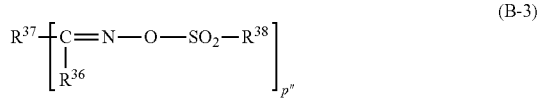
(B-3)

In the formula, $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenanthryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. Further, the halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), as the alkyl group having no substituent and the halogenated alkyl group for $R^{36}$, the same alkyl group having no substituent and the halogenated alkyl group described above for $R^{33}$ can be used.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate acid generators disclosed in Japanese Unexamined Patent Application, First Publication No. Hei 9-208554 (Chemical Formulas 18 and 19 shown in paragraphs [0012] to [0014]) and oxime sulfonate acid generators disclosed in WO 20041074242A2 (Examples 1 to 40 described at pages 65 to 85) may be preferably used.

Furthermore, as preferable examples, the following can be used.

[Chemical Formula 68]

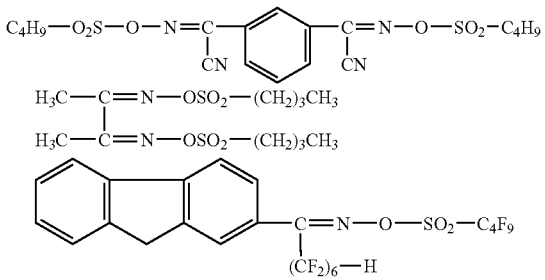

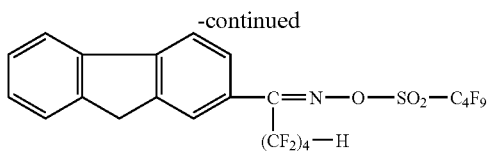

Of the aforementioned diazomethane acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as examples of poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be given.

As the component (B2), one type of acid generator may be used, or two or more types of acid generators may be used in combination.

Among the aforementioned examples, as the component (B2), an acid generator having an anion in which $R^{4''}$ represents a fluorinated alkyl group which may have a substituent is preferable, and an onium salt acid generator having a fluorinated alkylsulfonate ion which may have a substituent is more preferable.

When the component (B) includes the component (B2), the amount of the (B2) within the component (B) is preferably in the range of 1 to 90% by weight, more preferably 5 to 70% by weight, and still more preferably 10 to 60% by weight.

In the component (B), the mixing ratio of the component (B1) to the component (B2) ((B1):(B2)) is preferably in the range of 90:10 to 10:90, more preferably 80:20 to 20:80, still more preferably 70:30 to 25:75, and most preferably 65:35 to 30:70.

In the resist composition of the present invention, the total amount of the component (B), relative to 100 parts by weight of the component (A) is preferably 0.5 to 60 parts by weight, and more preferably 1 to 40 parts by weight. When the amount of the component (B) is within the above-mentioned range, formation of a resist pattern can be satisfactorily performed. Further, by virtue of the above-mentioned range, a uniform solution can be obtained and the storage stability becomes satisfactory.

<Optional Components>
[Component (D)]

It is preferable that the resist composition of the present invention further includes a nitrogen-containing organic compound (D) (hereafter referred to as the component (D)) as an optional component.

As the component (D), there is no particular limitation as long as it functions as an acid diffusion control agent, i.e., a quencher which traps the acid generated from the component (B) upon exposure. A multitude of these components (D) have already been proposed, and any of these known compounds may be used, although an aliphatic amine, and particularly a secondary aliphatic amine or tertiary aliphatic amine is preferable. The term "aliphatic cyclic group" refers to a monocyclic group or polycyclic group that has no aromaticity. An aliphatic amine is an amine having one or more aliphatic groups, and the aliphatic groups preferably have 1 to 20 carbon atoms.

Examples of these aliphatic amines include amines in which at least one hydrogen atom of ammonia ($NH_3$) has been substituted with an alkyl group or hydroxyalkyl group of no more than 20 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, tri-n-octanolamine, stearyldiethanolamine and laurildiethanolamine. Among these, trialkylamines and/or alkylalcoholamines are preferable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of aromatic amines include aniline, pyridine, 4-dimethylaminopyridine, pyrrole, indole, pyrazole, imidazole and derivatives thereof, as well as diphenylamine, triphenylamine and tribenzylamine.

Examples of other aliphatic amines include tris(2-methoxymethoxyethyl)amine, tris {2-(2-methoxyethoxy)ethyl}amine, tris {2-(2-methoxyethoxymethoxy)ethyl}amine, tris {2-(1-methoxyethoxy)ethyl}amine, tris {2-(1-ethoxyethoxy)ethyl}amine, tris{2-(1-ethoxypropoxy)ethyl}amine and tris[2-{2-(2-hydroxyethoxy)ethoxy}ethyl]amine.

These compounds can be used either alone, or in combinations of two or more different compounds.

The component (D) is typically used in an amount within a range from 0.01 to 5.0 parts by weight, relative to 100 parts by weight of the component (A). When the amount of the component (D) is within the above-mentioned range, the shape of the resist pattern and the post exposure stability of the latent image formed by the pattern-wise exposure of the resist layer are improved.

[Component (F)]

The resist composition of the present invention may further include a fluorine-containing compound component (F) (hereafter, referred to as "component (F)"). By including the component (F), the hydrophobicity of the surface of the resist film improves, thereby yielding a resist composition that is suitable also for immersion exposure.

The component (F) is not particularly limited and may be either a polymeric compound (polymer or copolymer) including a recurring unit, or a low molecular weight compound (non-polymer).

Examples of the polymeric compounds (polymers or copolymers) used as the component (F) include a polymeric compound having a recurring unit that contains a fluorine atom. More specifically, a polymeric compound including one or more recurring units that contain a fluorine atom; and a polymeric compound including recurring units consisting of a structural unit containing a fluorine atom and a structural unit with no fluorine atom, can be mentioned.

Further, examples of the low molecular weight compounds (non-polymers) used as the component (F) include a monomer for deriving structural units containing a fluorine atom which constitute the aforementioned polymeric compounds (polymers or copolymers).

Among these, the component (F) is preferably a polymeric compound (polymer or copolymer).

Structural Unit Containing a Fluorine Atom (Structural Unit (f1))

The structural unit containing a fluorine atom (hereafter, referred to as "structural unit (f1)") is not particularly limited as long as it is a structural unit containing a fluorine atom. For example, in the structural unit, a fluorine atom may be included within the side chain or may be directly bonded to the main chain, or a fluorine atom may be included in a substituent which is directly bonded to the main chain.

Of these various possibilities, as the structural unit (f1), a structural unit containing a fluorine atom within the side chain thereof is preferable. Specific examples include a structural unit having a group represented by general formula (f1-1-0) shown below; a structural unit having a fluorine atom and a group that contains an acid dissociable, dissolution inhibiting group; and a structural unit having a non-acid-dissociable fluorinated alkyl group of 1 to 20 carbon atoms, and a structural unit having a group represented by general formula (f1-1-0) is more preferable.

[Chemical Formula 69]

(f1-1-0)

In formula (f1-1-0), $R^8$ represents an organic group having a fluorine atom, provided that the carbon atom within the —C(=O)— moiety is not directly bonded to the main chain.

(Structural Unit Having a Group Represented by General Formula (f1-1-0))

In the formula (f1-1-0) above, $R^8$ represents an organic group having a fluorine atom.

An "organic group" is a group containing at least one carbon atom.

In the organic group having a fluorine atom for $R^8$, the structure of $R^8$ may be linear, branched or cyclic, and is preferably linear or branched.

In $R^8$, the organic group preferably has 1 to 20 carbon atoms, more preferably 1 to 15 carbon atoms, still more preferably 1 to 10 carbon atoms, and most preferably 1 to 5 carbon atoms.

In $R^8$, the fluorination ratio of the organic group is preferably 25% or more, more preferably 50% or more, and most preferably 60% or more, as the hydrophobicity of the resist film is enhanced.

The term "fluorination ratio" refers to the percentage (%) of the number of fluorine atoms relative to the total number of hydrogen atoms and fluorine atoms contained within the organic group.

More specifically, preferable examples of $R^8$ include a fluorinated hydrocarbon group which may have a substituent.

In the fluorinated hydrocarbon group, the hydrocarbon group (a hydrocarbon group which is not fluorinated) may be either an aliphatic hydrocarbon group or an aromatic hydrocarbon group, and an aliphatic hydrocarbon group is preferable.

An aliphatic hydrocarbon group refers to a hydrocarbon group having no aromaticity. The aliphatic hydrocarbon group may be either saturated or unsaturated, but in general, the aliphatic hydrocarbon group is preferably saturated.

As $R^8$, a fluorinated, saturated hydrocarbon group or a fluorinated, unsaturated hydrocarbon group is preferable, more preferably a fluorinated, saturated hydrocarbon group, and most preferably a fluorinated alkyl group.

Examples of fluorinated alkyl groups include groups in which part or all of the hydrogen atoms within the below described unsubstituted alkyl groups (below-described groups which do not have a substituent) have been substituted with a fluorine atom.

The fluorinated alkyl group may be either a group in which part of the hydrogen atoms within an unsubstituted alkyl group described below has been substituted with a fluorine atom, or a group in which all of the hydrogen atoms within an unsubstituted alkyl group described below has been substituted with a fluorine atom (i.e., a perfluoroalkyl group).

The unsubstituted alkyl group may be any of linear, branched or cyclic. Alternatively, the unsubstituted alkyl group may be a combination of a linear or branched alkyl group with a cyclic alkyl group.

The unsubstituted linear alkyl group preferably has 1 to 10 carbon atoms, and more preferably 1 to 8. Specific examples include a methyl group, an ethyl group, an n-propyl group, an n-butyl group, an n-pentyl group, an n-hexyl group, an n-heptyl group, an n-octyl group, an n-nonyl group and an n-decyl group.

The unsubstituted branched alkyl group preferably has 3 to 10 carbon atoms, and more preferably 3 to 8. As the branched alkyl group, a tertiary alkyl group is preferable.

As an example of an unsubstituted cyclic alkyl group, a group in which one hydrogen atom has been removed from a monocycloalkane or a polycycloalkane such as a bicycloalkane, tricycloalkane or tetracycloalkane can be given. Specific examples include monocycloalkyl groups such as a cyclopentyl group and a cyclohexyl group; and polycycloalkyl groups such as an adamantyl group, a norbornyl group, an isobornyl group, a tricyclodecyl group and a tetracyclododecyl group.

Examples of the combination of a linear or branched alkyl group with a cyclic alkyl group include groups in which a cyclic alkyl group as a substituent is bonded to a linear or branched alkyl group, and groups in which a linear or branched alkyl group as a substituent is bonded to a cyclic alkyl group.

Examples of the substituent for the fluorinated hydrocarbon group include alkyl groups of 1 to 5 carbon atoms.

As the fluorinated alkyl group for $R^8$, a linear or branched fluorinated alkyl group is preferable. In particular, a group represented by general formula (VII-1) or (VII-2) shown below is desirable, and a group represented by general formula (VII-1) is most preferable.

[Chemical Formula 70]

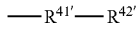 (VII-1)

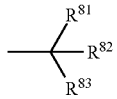 (VII-2)

In general formula (VII-1), $R^{41'}$ represents an unsubstituted alkylene group of 1 to 9 carbon atoms, and $R^{42'}$ represents a fluorinated alkyl group of 1 to 9 carbon atoms, provided that the total number of carbon atoms of $R^{41'}$ and $R^{42'}$ is no more than 10. In general formula (VII-2), each of $R^{81}$ to $R^{83}$ independently represents a linear alkyl group of 1 to 5 carbon atoms, provided that at least one of $R^{81}$ to $R^{83}$ represents an alkyl group having a fluorine atom.

In general formula (VII-1), the alkylene group for $R^{41'}$ may be linear, branched or cyclic, and is preferably linear or branched. Further, the number of carbon atoms within the alkylene group is preferably within a range of from 1 to 5.

As $R^{41'}$, a methylene group, an ethylene group or a propylene group is particularly desirable.

As $R^{42'}$, a linear or branched fluorinated alkyl group of 1 to 5 carbon atoms is preferable, and a perfluoroalkyl group is particularly desirable. Among perfluoroalkyl groups, a trifluoromethyl group and a pentafluoroethyl group are preferable.

In general formula (VII-2), as the alkyl group for $R^{81}$ to $R^{83}$, an ethyl group or a methyl group is preferable, and a methyl group is particularly desirable. At least one of the alkyl groups for $R^{81}$ to $R^{83}$ is a fluorinated alkyl group, and all of the alkyl groups for $R^{81}$ to $R^{83}$ may be fluorinated alkyl groups.

In general formula (f1-1-0), the carbon atom within the —C(=O)— moiety is not directly bonded to the main chain. As a result, the "—O—$R^8$" group may be dissociated satisfactorily by the action of an alkali developing solution which is weakly basic.

In other words, the "—O—$R^8$" group is dissociated from a group represented by general formula (f1-1-0) due to hydrolysis caused by the action of an alkali developing solution. Therefore, in the group represented by general formula (f1-1-0), a hydrophilic group [—C(=O)—OH] is formed when the "—O—$R^8$"group dissociates. Accordingly, the hydrophilicity of the component (F) is enhanced, and hence, the compatibility of the component (F) with the alkali developing solution is improved. As a result, the hydrophilicity of the resist film surface is enhanced during developing.

In the resist composition of the present invention, as the structural unit (f1), a structural unit (f1-1) represented by general formula (f1-1-1) shown below can be mentioned as a preferable example, because favorable solubility of the composition in organic solvents can be achieved, and the hydrophobicity of the surface of the resist film can be enhanced.

[Chemical Formula 71]

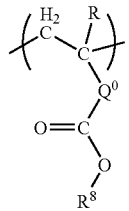 (f1-1-1)

In formula (f1-1-1), R represents a hydrogen atom, a lower alkyl group of 1 to 5 carbon atoms or a halogenated lower alkyl group of 1 to 5 carbon atoms; $Q^0$ represents a single bond or a divalent linking group; and $R^8$ represents an organic group having a fluorine atom.

Structural Unit (f1-1)

The structural unit (f1-1) is a structural unit represented by the aforementioned general formula (f1-1-1).

In general formula (f1-1-1), R represents a hydrogen atom, a lower alkyl group of 1 to 5 carbon atoms or a halogenated lower alkyl group of 1 to 5 carbon atoms.

The lower alkyl group and halogenated lower alkyl group for R are the same as defined for the lower alkyl group and halogenated lower alkyl group which may be bonded to the α-position of the aforementioned acrylate ester.

In general formula (f1-1-1), $Q^0$ represents a single bond or a divalent linking group.

Preferable examples of the divalent linking group for $Q^0$ include a hydrocarbon group which may have a substituent, and a group containing a hetero atom.

(Hydrocarbon Group which May have a Substituent)

With respect to the divalent linking group for $Q^0$, the hydrocarbon group may "have a substituent" means that part or all of the hydrogen atoms of the hydrocarbon group may be substituted with groups or atoms other than hydrogen atoms.

The hydrocarbon group for $Q^0$ may be either an aliphatic hydrocarbon group, or an aromatic hydrocarbon group.

Here, an aliphatic hydrocarbon group refers to a hydrocarbon group that has no aromaticity. The aliphatic hydrocarbon group may be either saturated or unsaturated, but in general, the aliphatic hydrocarbon group is preferably saturated.

Specific examples of the aliphatic hydrocarbon group include a linear or branched aliphatic hydrocarbon group and an aliphatic hydrocarbon group containing a ring in the structure thereof.

The linear or branched aliphatic hydrocarbon group for $Q^0$ preferably has 1 to 10 carbon atoms, more preferably 1 to 8 carbon atoms, still more preferably 1 to 5 carbon atoms, and most preferably 1 to 3 carbon atoms.

As a linear aliphatic hydrocarbon group, a linear alkylene group is preferable, and specific examples include a methylene group, an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, a branched alkylene group is preferable, and specific examples include alkylalkylene groups, e.g., alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—; alkylethylene groups such as —CH($CH_3$)$CH_2$—, —CH($CH_3$)CH($CH_3$)—, —C($CH_3$)$_2CH_2$— and —CH($CH_2CH_3$)$CH_2$—; alkyltrimethylene groups such as —CH($CH_3$)$CH_2CH_2$— and —$CH_2$CH($CH_3$)$CH_2$—; and alkyltetramethylene groups such as —CH($CH_3$)

CH$_2$CH$_2$CH$_2$— and —CH$_2$CH(CH$_3$)CH$_2$CH$_2$—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of the substituent include a fluorine atom, a fluorinated lower alkyl group of 1 to 5 carbon atoms, and an oxygen atom (=O).

Examples of the aliphatic hydrocarbon group containing a ring represented by Q$^0$ include a cyclic aliphatic hydrocarbon group (an aliphatic hydrocarbon ring having 2 hydrogen atoms removed therefrom), a group in which the cyclic aliphatic hydrocarbon group is bonded to the terminal of the aforementioned chain-like aliphatic hydrocarbon group or interposed within the chain-like aliphatic hydrocarbon group.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group.

As the monocyclic group, a group in which two or more hydrogen atoms have been removed from a monocycloalkane of 3 to 6 carbon atoms is preferable. Examples of the monocycloalkane include cyclopentane and cyclohexane.

As the polycyclic group, a group in which two or more hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent.

Examples of the substituent include a lower alkyl group of 1 to 5 carbon atoms, a fluorine atom, a fluorinated lower alkyl group of 1 to 5 carbon atoms, and an oxygen atom (=O).

Examples of the aromatic hydrocarbon group for Q$^0$ include a divalent aromatic hydrocarbon group in which one hydrogen atom has been removed from a benzene ring of a monovalent aromatic hydrocarbon group such as a phenyl group, a biphenyl group, a fluorenyl group, a naphthyl group, an anthryl group or a phenanthryl group;

an aromatic hydrocarbon group in which part of the carbon atoms constituting the ring of the aforementioned divalent aromatic hydrocarbon group has been substituted with a hetero atom such as an oxygen atom, a sulfur atom or a nitrogen atom; and an aromatic hydrocarbon group in which one hydrogen atom has been removed from a benzene ring of an arylalkyl group such as a benzyl group, a phenethyl group, a 1-naphthylmethyl group, a 2-naphthylmethyl group, a 1-naphthylethyl group or a 2-naphthylethyl group.

Among these examples, the aforementioned divalent aromatic hydrocarbon group is preferable, and an aromatic hydrocarbon group in which one hydrogen atom has been removed from a phenyl group, or an aromatic hydrocarbon group in which one hydrogen atom has been removed from a naphthyl group is particularly desirable.

The alkyl chain within the arylalkyl group preferably has 1 to 4 carbon atom, more preferably 1 or 2, and most preferably 1.

The aromatic hydrocarbon group may or may not have a substituent. Examples of the substituent include a lower alkyl group of 1 to 5 carbon atoms, a fluorine atom, a fluorinated lower alkyl group of 1 to 5 carbon atoms, and an oxygen atom (=O).

Among the above-mentioned examples, as the hydrocarbon group which may have a substituent, a linear, branched or cyclic aliphatic hydrocarbon group or a divalent aromatic hydrocarbon group is preferable, and a methylene group, and ethylene group, —CH(CH$_3$)—, a group in which one hydrogen atom has been removed from a tetracyclododecyl group, or an aromatic hydrocarbon group in which one hydrogen atom has been removed from a phenyl group is particularly desirable.

(Group Containing a Hetero Atom)

A hetero atom is an atom other than carbon and hydrogen, and examples thereof include an oxygen atom, a nitrogen atom, a sulfur atom and a halogen atom.

Examples of the group containing a hetero atom include —O—, —C(=O)—, —C(=O)—O—, a carbonate bond (—O—C(=O)—O—), —NH—, —NR$^{05}$— (wherein R$^{05}$ represents an alkyl group), —NH—C(=O)—, =N—, and a combination of any of these "groups" with a divalent hydrocarbon group.

As examples of the divalent hydrocarbon group, the same groups as those described above for the hydrocarbon group which may have a substituent can be given, and a linear or branched aliphatic hydrocarbon group is preferable.

Among the above-mentioned examples, as the group containing a hetero atom, a combination of any of the aforementioned "groups" with a divalent hydrocarbon group is preferable. More specifically, it is particularly desirable to use a combination of any of the aforementioned "groups" with the aforementioned aliphatic hydrocarbon group, or a combination of the aforementioned aliphatic hydrocarbon group, any of the aforementioned "groups" and the aforementioned aliphatic hydrocarbon group.

In general formula (f1-1-1), R$^8$ represents an organic group having a fluorine atom, and is the same defined for R$^8$ in general formula (f1-1-0).

Preferable examples of the structural unit (f1-1) include structural units represented by general formula (f1-1-10) or (f1-1-20) shown below.

[Chemical Formula 72]

(f1-1-10)

(f1-1-20)

In the formulas, each R independently represents a hydrogen atom, a lower alkyl group of 1 to 5 carbon atoms or a halogenated lower alkyl group of 1 to 5 carbon atoms; X represents a divalent organic group; A$_{aryl}$ represents a divalent aromatic cyclic group which may have a substituent; X$_{01}$ represents a single bond or a divalent linking group; and each R$^8$ independently represents an organic group having a fluorine atom.

In formulas (f1-1-10) and (f1-1-20), R$^8$ is the same as defined above.

In formulas (f1-1-10) and (f1-1-20), as R$^8$, a fluorinated hydrocarbon group is preferable, a fluorinated alkyl group is more preferable, a fluorinated alkyl group of 1 to 5 carbon atoms is still more preferable, and —CH$_2$—CF$_3$, —CH$_2$—

$CF_2$—$CF_3$, —$CH(CF_3)_2$, —$CH_2$—$CF_2$—$CF_2$—$CF_3$, —$CH_2$—$CH_2$—$CF_2$—$CF_2$—$CF_3$, —$CH_2$—$CH_2$—$CF_2$—$CF_2$—$CF_2$—$CF_3$ are most preferable.

As the lower alkyl group for R, a linear or branched lower alkyl group is preferable, and specific examples thereof include a methyl group, an ethyl group, a propyl group, an isopropyl group, an n-butyl group, an isobutyl group, a tert-butyl group, a pentyl group, an isopentyl group and a neopentyl group.

Specific examples of the halogenated lower alkyl group include groups in which part or all of the hydrogen atoms of the aforementioned "lower alkyl group" have been substituted with a halogen atom. Examples of the halogen atom include a fluorine atom, a chlorine atom, a bromine atom and an iodine atom, and a fluorine atom is particularly desirable.

In the present invention, as R, a hydrogen atom, a lower alkyl group or a fluorinated lower alkyl group is preferable, and a hydrogen atom or a methyl group is more preferable in terms of industrial availability.

In general formula (f1-1-10), X represents a divalent organic group.

Preferable examples of X include a hydrocarbon group which may have a substituent, and a group containing a hetero atom, and the same hydrocarbon groups (which may have a substituent) and groups containing a hetero atom described above in the explanation of the divalent linking group for $Q^0$ can be used.

In general formula (f1-1-20), $A_{aryl}$ represents a divalent aromatic cyclic group which may have a substituent. A specific example of $A_{aryl}$ includes an aromatic hydrocarbon ring (which may have a substituent) having two or more hydrogen atoms removed therefrom.

The ring skeleton of the aromatic cyclic group for $A_{aryl}$ preferably has 6 to 15 carbon atoms. Examples of the ring skeleton include a benzene ring, a naphthalene ring, a phenanthrene ring and an anthracene ring. Among these, a benzene ring or a naphthalene ring is particularly desirable.

Examples of the substituent for the aromatic cyclic group represented by $A_{aryl}$ include a halogen atom, an alkyl group, an alkoxy group, a halogenated lower alkyl group and an oxygen atom (=O). Examples of the halogen atom include a fluorine atom, a chlorine atom, an iodine atom and a bromine atom. As the substituent for the aromatic cyclic group represented by $A_{aryl}$, a fluorine atom is preferable.

$A_{aryl}$ may be either an aromatic cyclic group having no substituent, or an aromatic cyclic group having a substituent, although an aromatic cyclic group having no substituent is preferable.

When $A_{aryl}$ represents an aromatic cyclic group having a substituent, the number of the substituent may be either 1 or at least 2, preferably 1 or 2, and more preferably 1.

In general formula (f1-1-20), $X_{01}$ represents a single bond or a divalent linking group.

Examples of the divalent linking group include an alkylene group of 1 to 10 carbon atoms, —O—, —C(=O)—, —C(=O)—O—, a carbonate bond (—O—C(=O)—O—), —NH—C(=O)—, and a combination of these groups, and a combination of —O— with an alkylene group of 1 to 10 carbon atoms or a combination of —C(=O)—O— with an alkylene group of 1 to 10 carbon atoms is more preferable.

Examples of alkylene groups of 1 to 10 carbon atoms include linear, branched or cyclic alkylene groups, and a linear or branched alkylene group of 1 to 5 carbon atoms and a cyclic alkylene group of 4 to 10 carbon atoms are preferable.

Among structural units represented by the aforementioned general formula (f1-1-10), structural units represented by general formulas (f1-1-11) to (f1-1-16) shown below are preferable.

Further, among structural units represented by the aforementioned general formula (f1-1-20), structural units represented by general formulas (f1-1-21) to (f1-1-26) shown below are preferable.

[Chemical Formula 73]

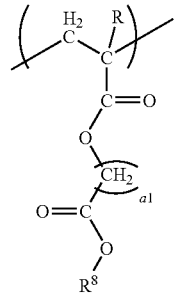

(f1-1-11)

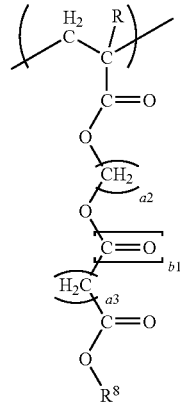

(f1-1-12)

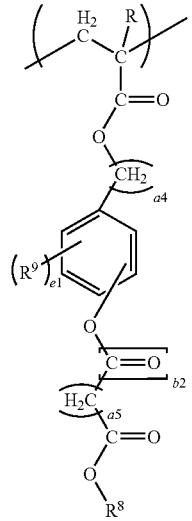

(f1-1-13)

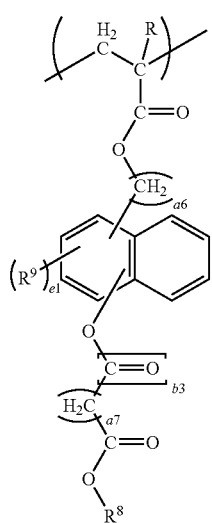
(f1-1-14)
[Chemical Formula 74]
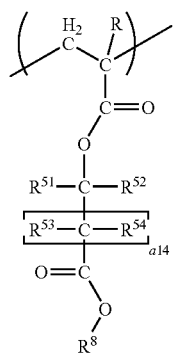
(f1-1-16)
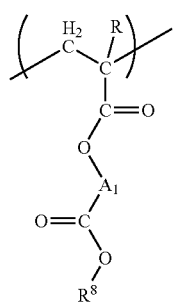
[Chemical Formula 75]
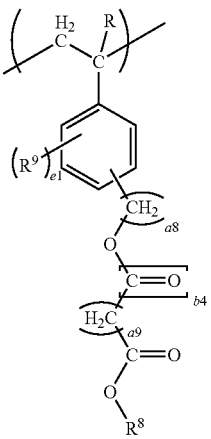
(f1-1-21)
(f1-1-15)
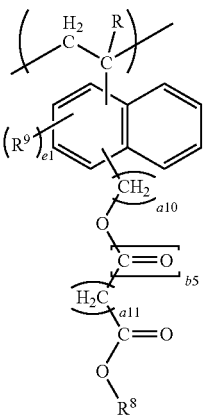
(f1-1-22)
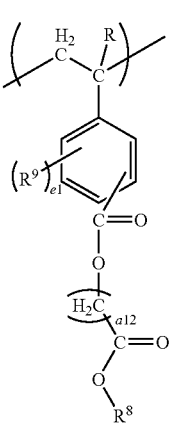
(f1-1-23)

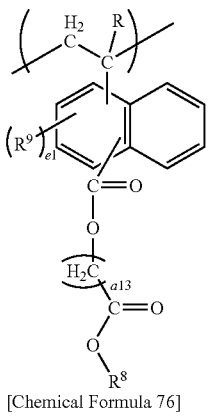

(f1-1-24)

[Chemical Formula 76]

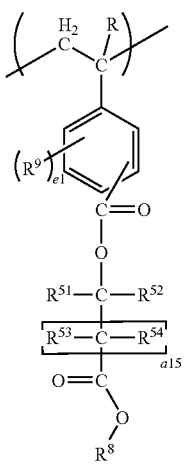

(f1-1-25)

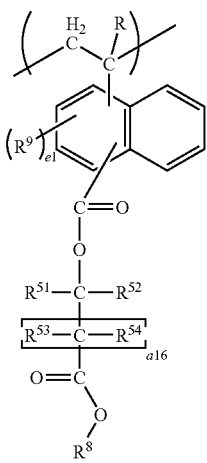

(f1-1-26)

In general formulas (f1-1-11) to (f1-1-16) and (f1-1-21) to (f1-1-26), R and $R^8$ are the same as defined above; each of $R^{51}$ and $R^{52}$ independently represents an alkyl group of 1 to 10 carbon atoms; each of $R^{53}$ and $R^{54}$ independently represents a hydrogen atom or an alkyl group of 1 to 10 carbon atoms; each of a1, a2, a3, a5, a7 a9 and a11 to a13 independently represents an integer of 1 to 5; each of a4, a6, a8 and a10 independently represents an integer of 0 to 5; each of a14 to a16 independently represents an integer of 1 to 5; each of b1 to b5 independently represents 0 or 1; each $R^9$ represents a substituent; e1 represents an integer of 0 to 2; and $A_1$ represents a cyclic alkylene group of 4 to 20 carbon atoms.

In formulas (f1-1-11) to (f1-1-16) and (f1-1-21) to (f1-1-26), as R, a hydrogen atom or a methyl group is preferable.

In formula (f1-1-11), a1 is preferably an integer of 1 to 3, and more preferably 1 or 2.

In formula (f1-1-12), it is preferable that each of a2 and a3 independently represent an integer of 1 to 3, and more preferably 1 or 2.

b1 is preferably 0.

In formula (f1-1-13), a4 is preferably an integer of 0 to 3, more preferably an integer of 0 to 2, and most preferably 0 or 1.

a5 is preferably an integer of 1 to 3, and more preferably 1 or 2.

Examples of the substituent for $R^9$ include a halogen atom, a lower alkyl group, an alkoxy group of 1 to 5 carbon atoms, a halogenated lower alkyl group, and an oxygen atom (=O). As the lower alkyl group, the same lower alkyl groups as those described above for R can be mentioned. Examples of the halogen atom include a fluorine atom, a chlorine atom, an iodine atom and a bromine atom. As the halogenated lower alkyl group, the same halogenated lower alkyl groups as those described above for R can be mentioned.

e1 is preferably 0 or 1, and most preferably 0 from an industrial viewpoint.

b2 is preferably 0.

In general formula (f1-1-14), a6 is preferably an integer of 0 to 3, more preferably an integer of 0 to 2, and most preferably 0 or 1.

a7 is preferably an integer of 1 to 3, and more preferably 1 or 2.

b3 is preferably 0.

$R^9$ and e1 are the same as defined above.

In formula (f1-1-15), a14 is preferably an integer of 0 to 3, more preferably an integer of 0 to 2, and most preferably 0 or 1.

It is preferable that each of $R^{51}$ and $R^{52}$ independently represents a linear, branched or cyclic alkyl group of 1 to 10 carbon atoms, and specific examples thereof include a methyl group, an ethyl group, an n-propyl group, an isopropyl group, an n-butyl group, an isobutyl group, a tert-butyl group, a tert-pentyl group, a cyclopentyl group, a cyclohexyl group, a cyclooctyl group, a norbornyl group, an isobornyl group, a tricyclodecyl group, an adamantyl group and a tetracyclododecyl group. Of these, an alkyl group of 1 to 6 carbon atoms is preferable, more preferably an alkyl group of 1 to 4 carbon atoms, and most preferably a methyl group or an ethyl group.

It is preferable that each of $R^{53}$ and $R^{54}$ independently represents a hydrogen atom, or a linear, branched or cyclic alkyl group of 1 to 10 carbon atoms. For $R^{53}$ and $R^{54}$, the linear, branched or cyclic alkyl group of 1 to 10 carbon atoms is the same as defined above for $R^{51}$ and $R^{52}$.

In formula (f1-1-16), $A_1$ represents a cyclic alkylene group of 4 to 20 carbon atoms, and is preferably a cyclic alkylene group of 5 to 15 carbon atoms, and more preferably a cyclic alkylene group of 6 to 12 carbon atoms. Specific examples of the cyclic alkylene group include those described above as the "cyclic aliphatic hydrocarbon group" for the aforementioned hydrocarbon group which may have a substituent, and the cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane.

As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of the substituent include a lower alkyl group of 1 to 5 carbon atoms, a fluorine atom, a fluorinated lower alkyl group of 1 to 5 carbon atoms, and an oxygen atom (=O).

In formula (f1-1-21), a8 is preferably an integer of 0 to 3, more preferably an integer of 0 to 2, and most preferably 0 or 1.

a9 is preferably an integer of 1 to 3, and more preferably 1 or 2.

b4 is preferably 0.

$R^9$ and e1 are the same as defined above.

In formula (f1-1-22), a10 is preferably an integer of 0 to 3, more preferably an integer of 0 to 2, and most preferably 0 or 1.

a11 is preferably an integer of 1 to 3, and more preferably 1 or 2.

b5 is preferably 0.

$R^9$ and e1 are the same as defined above.

In formula (f1-1-23), a12 is preferably an integer of 1 to 3, and more preferably 1 or 2.

$R^9$ and e1 are the same as defined above.

In formula (f1-1-24), a13 is preferably an integer of 1 to 3, and more preferably 1 or 2.

$R^9$ and e1 are the same as defined above.

In formulas (f1-1-25) and (f1-1-26), each of a15 and a16 is preferably an integer of 0 to 3, more preferably an integer of 0 to 2, and most preferably 0 or 1.

Each of $R^{51}$, $R^{52}$, $R^{53}$ and $R^{54}$ are the same as defined above.

$R^9$ and e are the same as defined above.

Specific examples of structural units represented by the above general formulas (f1-1-11) to (f1-1-16) and (f1-1-21) to (f1-1-26) are shown below.

[Chemical Formula 77]

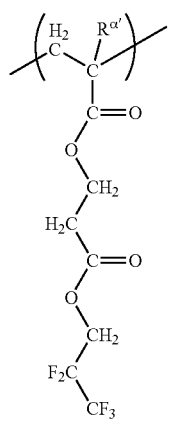
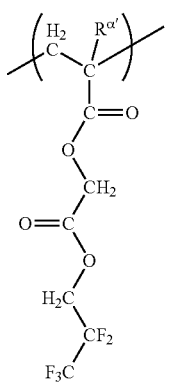
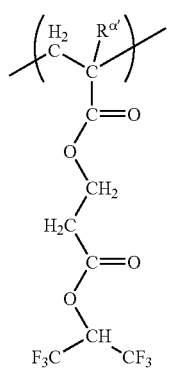
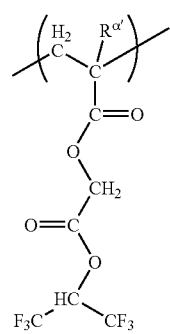

-continued

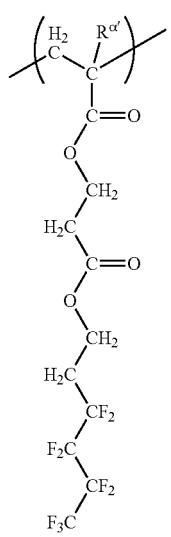
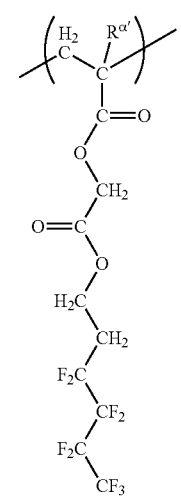
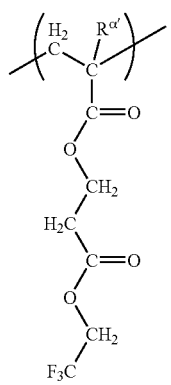
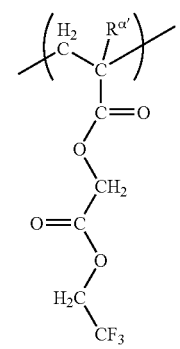

-continued
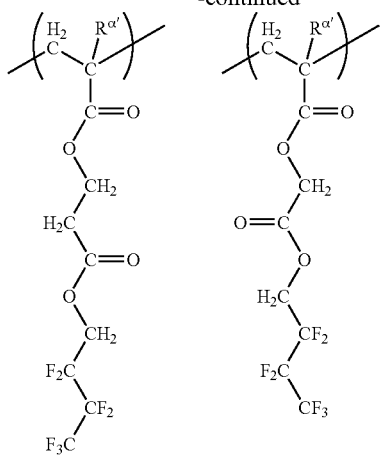
In the formulas, $R^{\alpha'}$ represents a hydrogen atom or a methyl group.
[Chemical Formula 78]
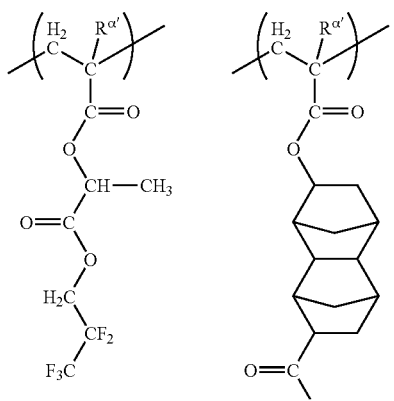
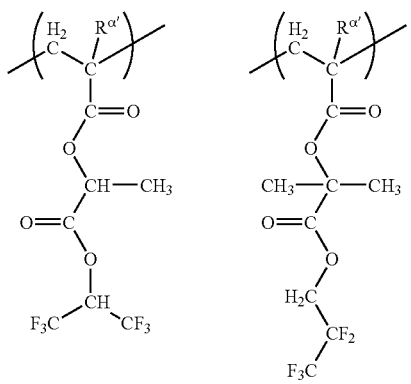
-continued
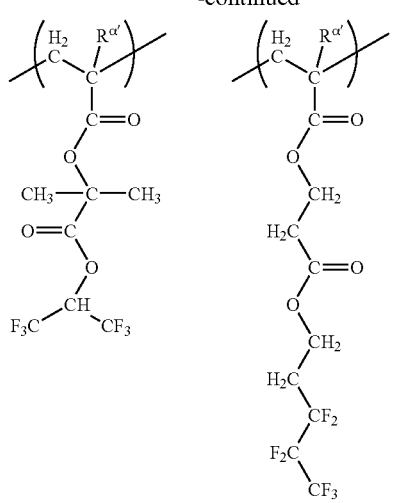
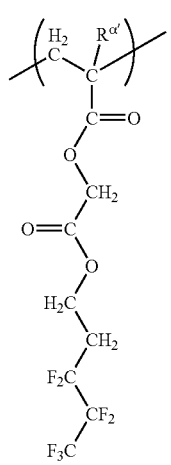
In the formulas, $R^{\alpha'}$ represents a hydrogen atom or a methyl group.
[Chemical Formula 79]
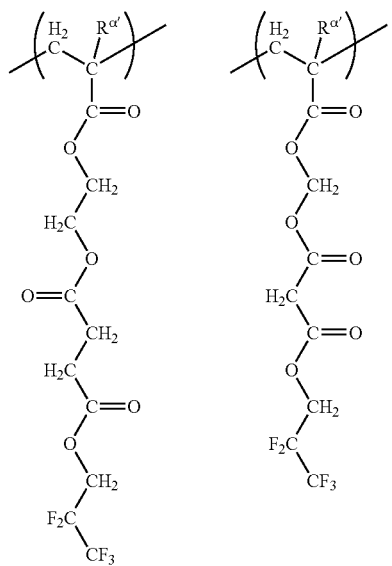

-continued
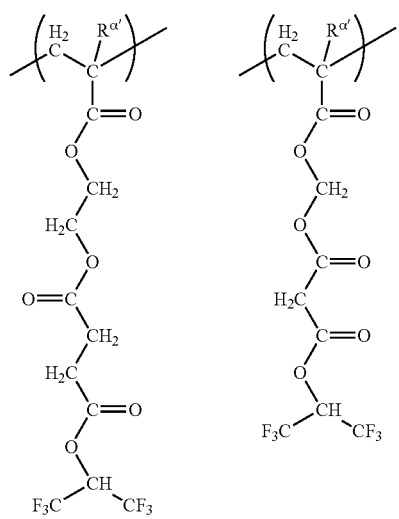 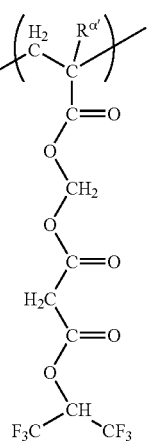
[Chemical Formula 80]
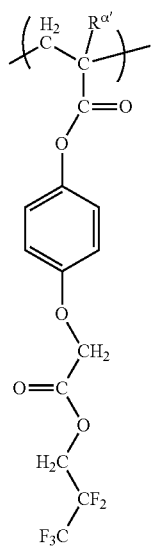 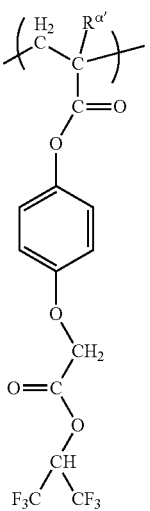
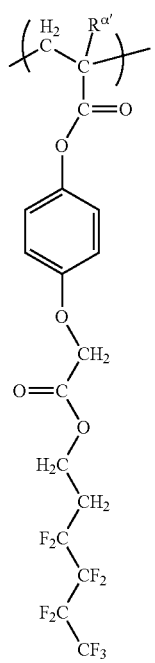 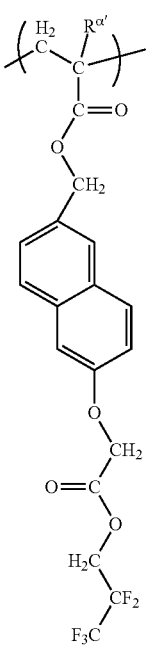
In the formulas, $R^{\alpha'}$ represents a hydrogen atom or a methyl group.

-continued

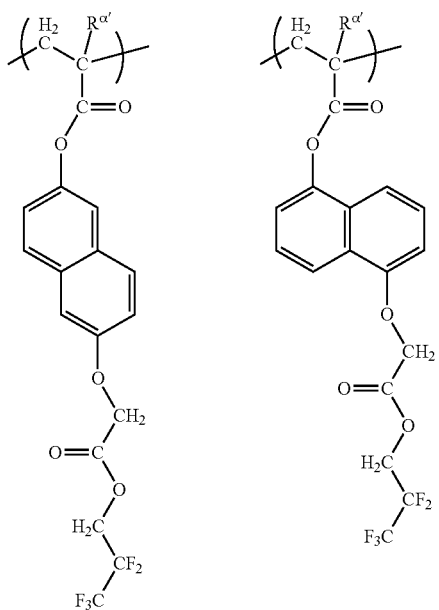

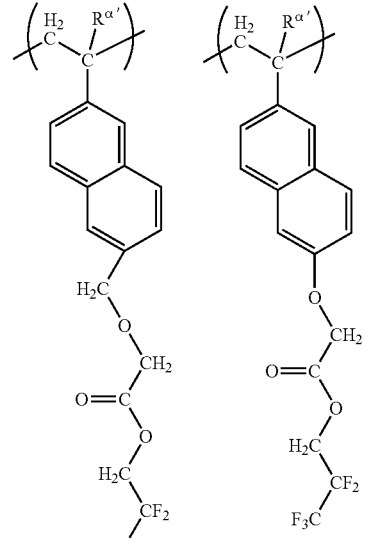

In the formulas, $R^{\alpha\prime}$ represents a hydrogen atom or a methyl group.

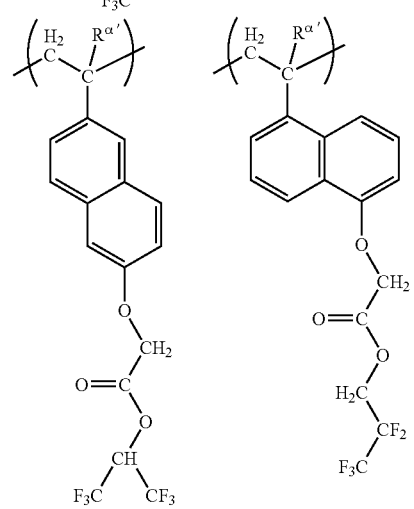

[Chemical Formula 81]

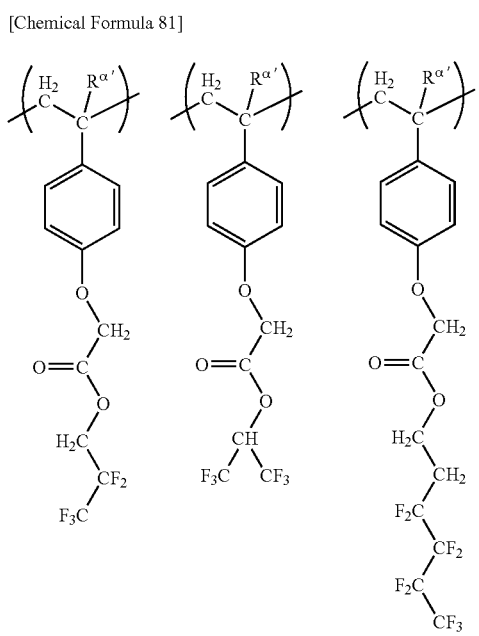

In the formulas, $R^{\alpha\prime}$ represents a hydrogen atom or a methyl group.

As the structural unit (f1-1), at least one structural unit selected from the group consisting of structural units represented by the aforementioned general formulas (f1-1-11) to (f1-1-16) and (f1-1-21) to (f1-1-26) is preferable, more preferably at least one structural unit selected from the group consisting of structural units represented by the aforementioned general formulas (f1-1-11) to (f1-1-13), (f1-1-21) and (f1-1-22), still more preferably at least one structural unit selected from the group consisting of structural units represented by the aforementioned general formulas (f1-1-11) and (f1-1-22), and most preferably structural units represented by the aforementioned general formula (f1-1-11).

In the component (F), as the structural unit (f1), one type of structural unit may be used alone, or two or more types may be used in combination.

In the component (F), the amount of the structural unit (f1) based on the combined total of all structural units constituting the component (F) is preferably 30 to 95 mol %, more preferably 40 to 90 mol %, and still more preferably 50 to 85 mol %.

When the amount of the structural unit (f1) is at least as large as the lower limit of the above-mentioned range, during resist pattern formation, the characteristic feature of enhancing hydrophobicity of the resist film is improved. On the other hand, when the amount of the structural unit (f1) is no more than the upper limit of the above-mentioned range, a good balance can be achieved with the other structural units.

When the structural unit (f1-1) is used as the structural unit (1), in the component (F), the amount of the structural unit (f1-1) based on the combined total of all structural units constituting the component (F) is preferably 30 to 95 mol %, more preferably 40 to 90 mol %, and still more preferably 50 to 85 mol %. When the amount of the structural unit (f1-1) is at least as large as the lower limit of the above-mentioned range, the characteristic feature of enhancing hydrophobicity of the resist film is improved. On the other hand, when the amount of the structural unit (f1) is no more than the upper limit of the above-mentioned range, a good balance can be achieved with the other structural units.

Other Structural Unit (Structural Unit (f2))

The component (F) may include a structural unit other than the structural unit (f1) (hereafter, referred to as "structural unit f2)"), as long as the effects of the present invention are not impaired.

There are no particular limitations on the structural unit (f2), provided the structural unit is derived from a compound that is copolymerizable with the compound that gives rise to the structural unit (f1).

Examples of the structural unit (f2) include structural units which have been proposed for the base resin of a conventional chemically amplified resist (such as the aforementioned structural units (a1) to (a4) in the component (A1)). When used in a positive resist composition, the structural unit (a1) can be mentioned as a preferable example of the structural unit (f2).

In the component (F), as the structural unit (f2), one type of structural unit may be used alone, or two or more types may be used in combination.

For example, when the structural unit (a1) is used as the structural unit (f2), of the various structural units classified as the structural unit (a1), structural units represented by general formulas (a1-1) and (a1-3) are preferable, structural units represented by general formula (a1-1) are more preferable, and structural units represented by general formulas (a1-1-16) to (a1-1-23), (a1-1-27) and (a1-1-31) to (a1-1-33) are particularly desirable.

In the component (F), the amount of the structural unit (a1) based on the combined total of all structural units constituting the component (F) is preferably 1 to 40 mol %, and more preferably 5 to 30 mol %.

When the amount of the structural unit (a1) is within the above-mentioned range, the water repellency is improved, and a good balance can be achieved with the other structural units.

In the resist composition of the present invention, the component (F) is preferably a polymeric compound that includes the structural unit (f1) (hereafter, referred to as "fluorine-containing resin (F1-1)").

Examples of such a fluorine-containing resin (F1-1) include a copolymer containing the structural unit (11) and the structural unit (12). More specifically, a copolymer containing the structural unit (1) and the structural unit (a1) can be mentioned as a preferable example.

Among the above-mentioned examples, it is particularly desirable that the fluorine-containing resin (F1-1) be a copolymer consisting of the structural unit (f1-1) and the structural unit (a1).

In the component (F), as the fluorine-containing resin (F1-1), one type may be used alone, or two or more types may be used in combination.

In the resist composition of the present invention, as the fluorine-containing resin (F1-1) usable in the case of a positive resist composition, a resin that includes a combination of structural units such as that shown below is particularly desirable.

[Chemical Formula 82]

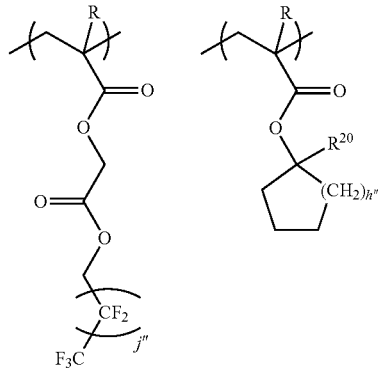

Flourine-containing resin (F1-1-10)

In the formula, R is the same as defined above, and the plurality of R may be either the same or different from each other; j" represents an integer of 1 to 3, preferably 1 or 2, and most preferably 1; $R^{20}$ represents a lower alkyl group of 1 to 5 carbon atoms and is the same as the lower alkyl group for R above, and is preferably a methyl group or an ethyl group, and most preferably an ethyl group; h" represents an integer of 1 to 6 and is preferably 3 or 4, and is most preferably 4.

The weight average molecular weight (Mw) (the polystyrene equivalent value determined by gel permeation chromatography) of the component (F) is not particularly limited, but is preferably 2,000 to 50,000, more preferably 3,000 to 30,000, and most preferably 4,000 to 25,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (F) is preferably 1.0 to 5.0, more preferably 1.0 to 3.0, and most preferably 1.2 to 2.5. Here, Mn is the number average molecular weight.

The component (F) can be produced, for example, by a conventional radical polymerization or the like of the monomers corresponding with each of the structural units that constitute the component (F), using a radical polymerization initiator such as azobisisobutyronitrile (AIBN) or dimethyl 2,2'-azobis(isobutyrate) (V-601).

In the resist composition of the present invention, the amount of the component (F), relative to 100 parts by weight of the component (A) is preferably from 0.5 to 30 parts by weight, more preferably from 1 to 20 parts by weight, and most preferably from 1 to 10 parts by weight. When the amount of the component (F) is at least as large as the lower limit of the above-mentioned range, the hydrophobicity of a resist film formed using the resist composition is enhanced.

Further, the hydrophobicity of a resist film formed using the resist composition is also suitable for immersion exposure. On the other hand, when the amount of the component (F) is no more than the upper limit of the above-mentioned range, solubility of the component (F) in a resist solvent (organic solvent) is improved. Further, the lithographic properties are also improved.

[Component (E)]

Furthermore, in the resist composition for immersion exposure according to the present invention, for preventing any deterioration in sensitivity, and improving the resist pattern shape and the post exposure stability of the latent image formed by the pattern-wise exposure of the resist layer, at least one compound (E) (hereafter referred to as "component (E)") selected from the group consisting of organic carboxylic acids, and phosphorus oxo acids and derivatives thereof can be added.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one type may be used alone, or two or more types may be used in combination.

As the component (E), an organic carboxylic acid is preferable, and salicylic acid is particularly desirable.

The component (E) is typically used in an amount within a range from 0.01 to 5.0 parts by weight, relative to 100 parts by weight of the component (A).

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

[Component (S)]

The resist composition of the present invention can be prepared by dissolving the materials for the resist composition in an organic solvent (hereafter, referred to as "component (S)").

The component (S) may be any organic solvent which can dissolve the respective components to give a uniform solution, and any one or more kinds of organic solvents can be appropriately selected from those which have been conventionally known as solvents for a chemically amplified resist.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

These solvents can be used individually, or in combination as a mixed solvent.

Among these, propylene glycol monomethyl ether acetate (PGMEA), propylene glycol monomethyl ether (PGME) and ethyl lactate (EL) are preferable.

Further, among the mixed solvents, a mixed solvent obtained by mixing PGMEA or PGME with a polar solvent is preferable. The mixing ratio (weight ratio) of the mixed solvent can be appropriately determined, taking into consideration the compatibility of the PGMEA or PGME with the polar solvent, but is preferably in a range from 1:9 to 9:1, and more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

Further, a mixed solvent of PGME with dimethyl sulfoxide is also preferable. In this case, the mixing ratio (former:latter) of such a mixed solvent is preferably from 9:1 to 1:9, more preferably from 8:2 to 2:8, and most preferably from 7:3 to 5:5.

The amount of the component (S) is not particularly limited, and is adjusted appropriately to a concentration that enables application of a coating solution to a substrate in accordance with the thickness of the coating film. In general, the component (S) is used in an amount that yields a solid content for the resist composition that is within a range from 2 to 20% by weight, and preferably from 3 to 15% by weight.

Dissolving of the materials for a resist composition in the component (S) can be conducted by simply mixing and stirring each of the above components together using conventional methods, and where required, the composition may also be mixed and dispersed using a dispersion device such as a dissolver, a homogenizer, or a triple roll mill. Furthermore, following mixing, the composition may also be filtered using a mesh, or a membrane filter or the like.

The resist composition of the present invention described above is a novel composition essentially unknown in the art.

According to the resist composition of the present invention, both of an excellent solubility in a developing solution and excellent lithography properties can be achieved. Especially, due to the high solubility of the component (B1) in an alkali developing solution after exposure, there is a low risk of the component (B 1) precipitating, thereby enabling the formation of a resist pattern with reduced defects. The reason why these effects can be achieved has not been elucidated yet, but is presumed as follows.

In the resist composition of the present invention, an acid generator (B1) including a compound having a group represented by general formula (I) on a cation moiety thereof is used. In the component (B1), by the action of an alkali developing solution (aqueous alkali solution), the single bond of O—C within "—O—C(=O)—" in the group represented by general formula (I) is broken (hydrolyzed), and "—C(=O)—CH$_2$-Q$^5$-R$^5$" is dissociated from the cation moiety of the component (B1). As a result, a compound having an "—OH" group on the terminal thereof and a carboxylic acid represented by the formula "HO—C(=O)—CH$_2$-Q$^5$-R$^5$" are formed. Since the generated compound and carboxylic acid exhibit high solubility in an alkali developing solution, with respect to the component (B1) after development, possibility of risks such as precipitating, not dissolving completely, and adhering becomes low, as compared to a conventional acid generator. For this reason, it is presumed that the aforementioned effects can be achieved.

Further, according to the resist composition of the present invention, in the formation of a line and space pattern for example, the removability of the space portions (extent to which the material at the space portions is removed) is excellent, and a resist pattern having a dimension close to the target space size can be formed.

Furthermore, according to the resist composition of the present invention, lithography properties such as exposure latitude (EL margin) are excellent. The larger the value of the "EL margin", the smaller the change in the pattern size by the variation of the exposure dose, meaning that the process margin is high.

<<Method of Forming a Resist Pattern>>

The method of forming a resist pattern according to the present invention includes: forming a resist film on a substrate using a resist composition of the present invention; conducting exposure of the resist film; and alkali-developing the resist film to form a resist pattern.

More specifically, the method for forming a resist pattern according to the present invention can be performed, for example, as follows.

More specifically, the method for forming a resist pattern according to the present invention can be performed, for example, as follows. Firstly, a resist composition of the present invention is applied onto a substrate using a spinner or the like, and a prebake (post applied bake (PAB)) is conducted under temperature conditions of 80 to 150° C. for 40 to 120 seconds, preferably 60 to 90 seconds to form a resist film. Then, for example, using an ArF exposure apparatus or the like, the resist film is selectively exposed with an ArF exposure apparatus, an electron beam exposure apparatus, an EUV exposure apparatus or the like through a mask pattern or directly irradiated with electron beam without a mask pattern, followed by post exposure bake (PEB) under temperature conditions of 80 to 150° C. for 40 to 120 seconds, preferably 60 to 90 seconds. Subsequently, developing is conducted using an alkali developing solution such as a 0.1 to 10% by weight aqueous solution of tetramethylammonium hydroxide (TMAH), preferably followed by rinsing with pure water, and drying. If desired, bake treatment (post bake) can be conducted following the developing. In this manner, a resist pattern that is faithful to the mask pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) can be used.

The wavelength to be used for exposure is not particularly limited and the exposure can be conducted using radiation such as ArF excimer laser, KrF excimer laser, F$_2$ excimer laser, extreme ultraviolet rays (EUV), vacuum ultraviolet rays (VUV), electron beam (EB), X-rays, and soft X-rays. The positive resist composition of the present invention is effective to KrF excimer laser, ArF excimer laser, EB and EUV, and particularly effective to ArF excimer laser, EB or EUV.

The exposure of the resist film can be either a general exposure (dry exposure) conducted in air or an inert gas such as nitrogen, or immersion exposure (immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

<<Compound>>

The compound according to a third aspect of the present invention is a compound represented by the aforementioned general formula (b1-11) (hereafter, this compound is referred to as "compound (b1-11)").

The compound (b1-11) is the same as the component (B1) for the resist composition according to the first aspect of the present invention.

The compound (b1-11) can be produced by a normal method.

Specifically, for example, when $R^{7\prime\prime}$ represents an aryl group having one group represented by general formula (I), such a compound (hereafter, referred to as "compound (b1-11-a)") can be produced as follows.

Firstly, for example, a compound represented by general formula (b1-01) shown below and a compound represented by general formula (b1-02) shown below are added to and reacted in a solution of an organic acid $H^+B^-$ ($B^-$ represents an anion moiety of an organic acid, such as a methanesulfonate ion). Then, pure water and an organic solvent (e.g., dichloromethane, tetrahydrofuran, or the like) are added thereto, and the organic phase is collected. From the organic phase, a compound represented by general formula (b1-03) is collected.

[Chemical Formula 83]

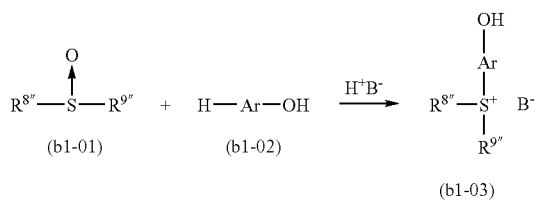

Subsequently, the compound represented by general formula (b1-03) is added to an organic solvent (e.g., acetone, dichloromethane, tetrahydrofuran, or the like), followed by cooling. Then, a compound represented by general formula (b1-04) shown below is added thereto and reacted, followed by liquid separation and washing with water. From the resulting organic phase, a compound represented by general formula (b1-05) shown below is obtained.

[Chemical Formula 84]

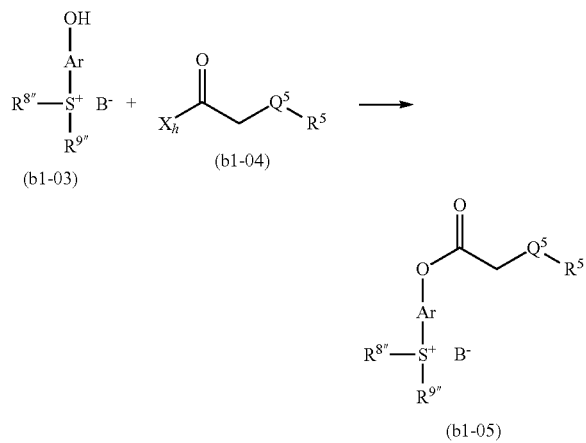

Thereafter, a compound represented by the formula (b1-05) is dissolved in a mixed solvent containing an organic solvent (e.g., dichloromethane, tetrahydrofuran, or the like) and water, and an alkali metal salt $L^+X^-$ containing a desired anion $X^-$ ($L^+$ represents an alkali metal cation such as a lithium ion, a sodium ion or a potassium ion) is added thereto to effect a reaction. The resultant is subjected to liquid separation and washing with water, and a compound (b1-11-a) is collected from the organic phase.

[Chemical Formula 85]

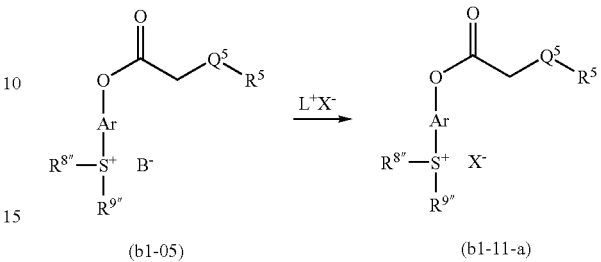

In the formulas, $R^{8\prime\prime}$, $R^{9\prime\prime}$, $Q^5$, $R^5$ and $X^-$ are the same as defined above, Ar represents an arylene group, B represents an anion moiety of an organic acid, $L^+$ represents an alkali metal cation and $X_h$ represents a halogen atom.

As the arylene group for Ar, a group in which one hydrogen atom has been removed from an aryl group for $R^{7\prime\prime}$ to $R^{9\prime\prime}$ which may have a substituent can be mentioned.

The halogen atom for $X_h$ is preferably a bromine atom or a chlorine atom.

The structure of the thus obtained compound can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

The compound (b1-11) described above is a novel compound essentially unknown in the art.

Further, the compound (b1-11) is a novel compound useful as an acid generator for a resist composition, and can be blended in a resist composition as an acid generator.

<<Acid Generator>>

The acid generator according to a fourth aspect of the present invention is an acid generator including the compound (b1-11).

The acid generator is useful for a chemically amplified resist composition, for example, the acid-generator component (B) of the resist composition according to the first aspect of the present invention.

EXAMPLES

As follows is a description of examples of the present invention, although the scope of the present invention is by no way limited by these examples.

In the following examples, a unit represented by a chemical formula (1) is designated as "compound (1)", and the same applies for compounds represented by other formulas.

<Synthesis of Base Component (A)>

The resin component (A1) used as the base component (A) in the present examples was synthesized in accordance with the following Synthesis Example 2, using the compound (1) synthesized in accordance with the following Synthesis Example 1.

Synthesis Example 1

Synthesis of Compound (1)

300 ml of a THF solution containing 20 g (105.14 mmol) of an alcohol (1), 30.23 g (157.71 mmol) of ethyldiisopropylaminocarbodiimide (EDCI) hydrochloride and 0.6 g (5 mmol) of dimethylaminopyridine (DMAP) was added to a 500 ml three-necked flask in a nitrogen atmosphere, and 16.67 g (115.66 mmol) of a precursor (1) was added thereto while cooling with ice (0° C.), followed by stirring at room temperature for 12 hours.

After conducting thin-layer chromatography (TLC) to confirm that the raw materials had been consumed, 50 ml of water was added to stop the reaction. Then, the reaction solvent was concentrated under reduced pressure, and extraction was conducted with ethyl acetate three times. The obtained organic phase was washed with water, saturated sodium hydrogencarbonate and 1N—HClaq in this order. Thereafter, the solvent was distilled off under reduced pressure, and the resulting product was dried, thereby obtaining the compound (1).

[Chemical Formula 86]

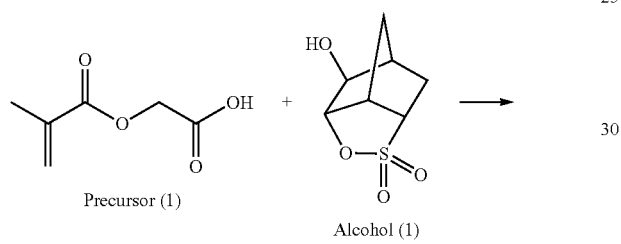

Precursor (1)  Alcohol (1)

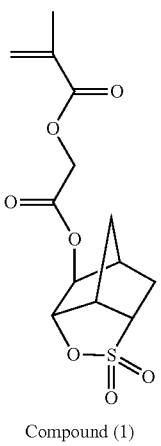

Compound (1)

The results of instrumental analysis of the obtained compound (1) were as follows.

$^1$H-NMR (CDCl$_3$, 400 MHz): δ(ppm)=6.22 (s, 1H,H$^a$), 5.70 (s, 1H,H$^b$), 4.71-4.85 (m, 2H,H$^{c,d}$), 4.67 (s, 2H,H$^k$), 3.40-3.60 (m, 2H,H$^{e,f}$), 2.58-2.70 (m, 1H,H$^g$), 2.11-2.21 (m, 2H,H$^h$), 2.00 (s, 3H,H$^i$), 1.76-2.09 (m, 2H,H$^j$).

From the results shown above, it was confirmed that the compound (1) had a structure shown below.

[Chemical Formula 87]

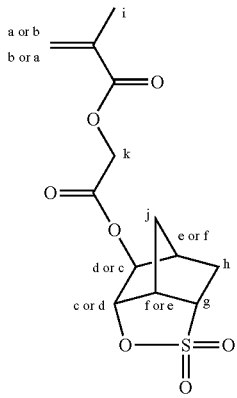

Synthesis Example 2

Synthesis of Polymeric Compound 1

In a three-necked flask equipped with a thermometer and a reflux tube, 11.77 g (69.23 mmol) of a compound (2), 15.00 g (47.47 mmol) of a compound (1), 16.58 g (63.29 mmol) of a compound (4), 4.65 g (27.69 mmol) of a compound (5) and 3.27 g (13.85 mmol) of a compound (3) were dissolved in 76.91 g of methyl ethyl ketone (MEK) to obtain a solution. Then, 22.1 mmol of dimethyl 2,2'-azobis(isobutyrate) (V-601) was added and dissolved in the obtained solution. The resultant was dropwise added to 42.72 g of MEK heated to 78° C. in a nitrogen atmosphere over 3 hours. The resulting reaction solution was heated while stirring for 4 hours, and then cooled to room temperature. The obtained reaction polymer solution was dropwise added to an excess amount of n-heptane, and an operation to deposit a polymer was conducted. Thereafter, the precipitated white powder was separated by filtration, followed by washing with an n-heptane/isopropylalcohol mixed solvent and drying, thereby obtaining 41 g of a polymeric compound 1 as an objective compound.

With respect to the polymeric compound 1, the weight average molecular weight (Mw) and the dispersity (Mw/Mn) were determined by the polystyrene equivalent value as measured by gel permeation chromatography (GPC). As a result, it was found that the weight average molecular weight was 7,900, and the dispersity was 1.78. Further, as a result of an analysis by carbon 13 nuclear magnetic resonance spectroscopy (600 MHz, $^{13}$C-NMR), it was found that the composition of the copolymer (ratio (molar ratio) of the respective structural units within the structural formula) was a2/a0/a11/a12/a3=35.0/26.5/17.9/13.2/7.4.

[Chemical Formula 88]

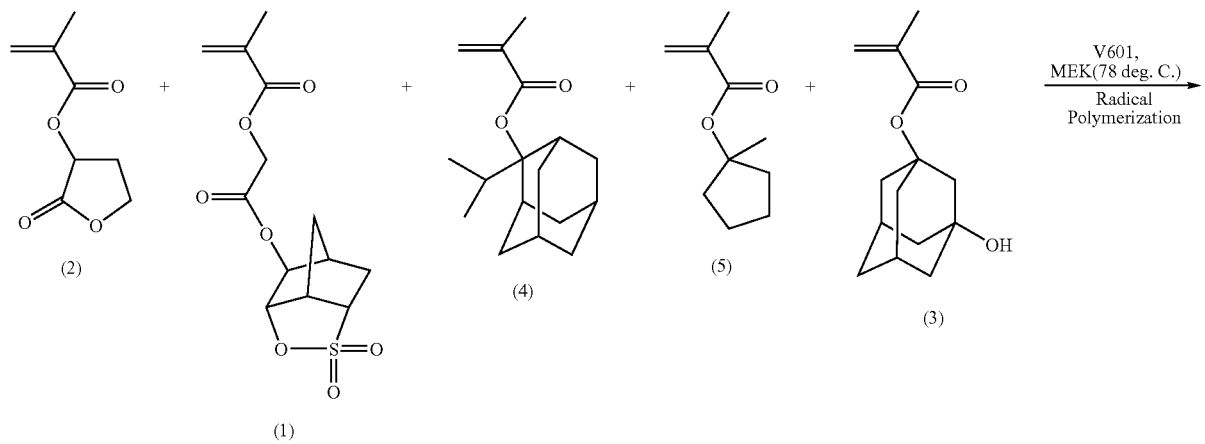

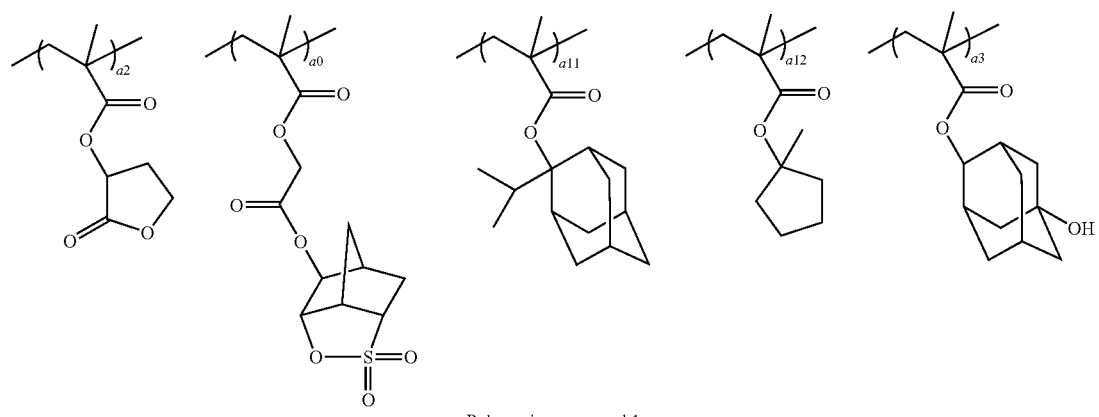

Polymeric compound 1

<Synthesis of Fluorine-containing Compound Component (F)>

The polymeric compound used as the fluorine-containing compound component (F) in the present examples (fluorine-containing resin 1) was synthesized in accordance with the following Synthesis Example 3.

Synthesis Example 3

Synthesis of Fluorine-containing Resin 1

15.00 g (54.32 mmol) of the compound (6) and 5.21 g (23.28 mmol) of the compound (7) were added to a three-necked flask equipped with a thermometer and a reflux tube and were dissolved by adding 114.52 g of THF thereto. Then, 4.66 mmol of dimethyl 2,2'-azobis(isobutyrate) (V-601) was added and dissolved in the obtained solution. The solution was stirred while heating at 80° C. for 6 hours in a nitrogen atmosphere, and was then cooled to room temperature. The resulting polymer solution was concentrated under reduced pressure, and dropwise added to an excess amount of n-heptane to thereby precipitate a polymer. Then, the precipitated polymer was separated by filtration, followed by washing and drying, thereby obtaining 5.6 g of a fluorine-containing resin 1 as an objective compound.

With respect to the obtained fluorine-containing resin 1, the weight average molecular weight (Mw) and the dispersity (Mw/Mn) were determined by the polystyrene equivalent value as measured by gel permeation chromatography (GPC). As a result, it was found that the weight average molecular weight was 23,900, and the dispersity was 1.5. Further, as a result of an analysis by carbon 13 nuclear magnetic resonance spectroscopy (600 MHz, $^{13}$C-NMR), it was found that the composition of the copolymer (ratio (molar ratio) of the respective structural units within the structural formula) was l/m=75.6/24.4.

[Chemical Formula 89]

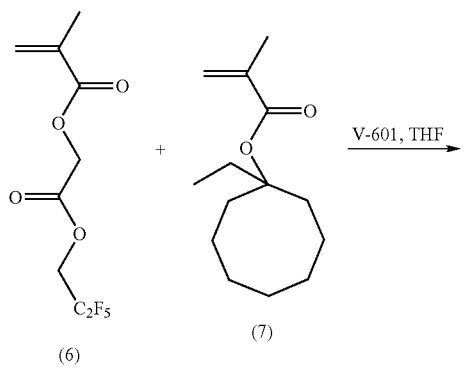

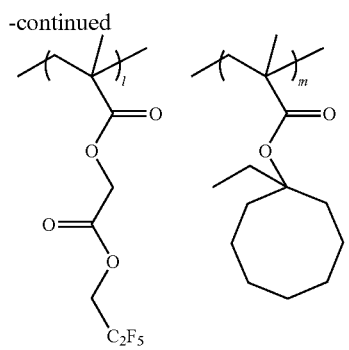

Fluorine-containing resin 1

Synthesis of Acid-generator Component (B)

Examples 1 to 23

The acid generators used as the acid-generator component (B) in the present examples were synthesized in accordance with the following synthesis examples.

Example 1

Synthesis of Compound (B1-1)

(i) Synthesis Example of Compound (8)

To 60.75 g of methanesulfonic acid controlled to 20° C. or lower was added 8.53 g of phosphorus oxide, 8.81 g of 2,6-dimethylphenol and 12.2 g of diphenylsulfoxide in small amounts. The resultant was matured for 30 minutes while maintaining the temperature at 15 to 20° C., followed by elevating the temperature to 40° C. and maturing for 2 hours. Then, the reaction mixture was dropwise added to 109.35 g of pure water cooled to 15° C. or lower. Thereafter, 54.68 g of dichloromethane was added and stirred, and the dichloromethane phase was collected. 386.86 g of hexane at a temperature of 20 to 25° C. was added to a separate vessel, and the dichloromethane phase was dropwise added thereto. Then, the resultant was matured at 20 to 25° C. for 30 minutes, followed by filtration, thereby obtaining a compound (8) (yield: 70.9%).

[Chemical Formula 90]

Compound (8)

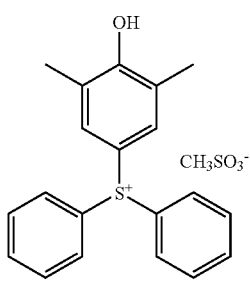

(ii) Synthesis Example of Compound (9)

4.00 g of the compound (8) and 28.0 g of dichloromethane were added to a three-necked flask in a nitrogen atmosphere and stirred. Then, 1.31 g of triethylamine diluted with 4.00 g of dichloromethane was dropwise added thereto. While maintaining the reaction system at a temperature of 10° C. or lower, 1.63 g of acetoxyacetyl chloride diluted with 8.00 g of dichloromethane was dropwise added over 15 minutes. Then, a reaction was effected at room temperature for 3 hours. After the completion of the reaction, the dichloromethane phase was washed with a diluted hydrochloric acid and water in this order, followed by distilling off dichloromethane under reduced pressure. The resulting oily substance was dried, thereby obtaining 2.76 g of a compound (9).

The compound (9) was analyzed by NMR.

$^1$H-NMR (DMSOd-6,400 MHz): δ(ppm)=7.77-7.89(m, 10H,ArH), 7.70(s,2H, ArH), 5.10(s, 2H,OCOCH2O), 2.31(s, 3H,CH3SO3), 2.07-2.19(m,9H, OCOCH3+CH3)

From the results shown above, it was confirmed that the compound (9) had a structure shown below.

[Chemical Formula 91]

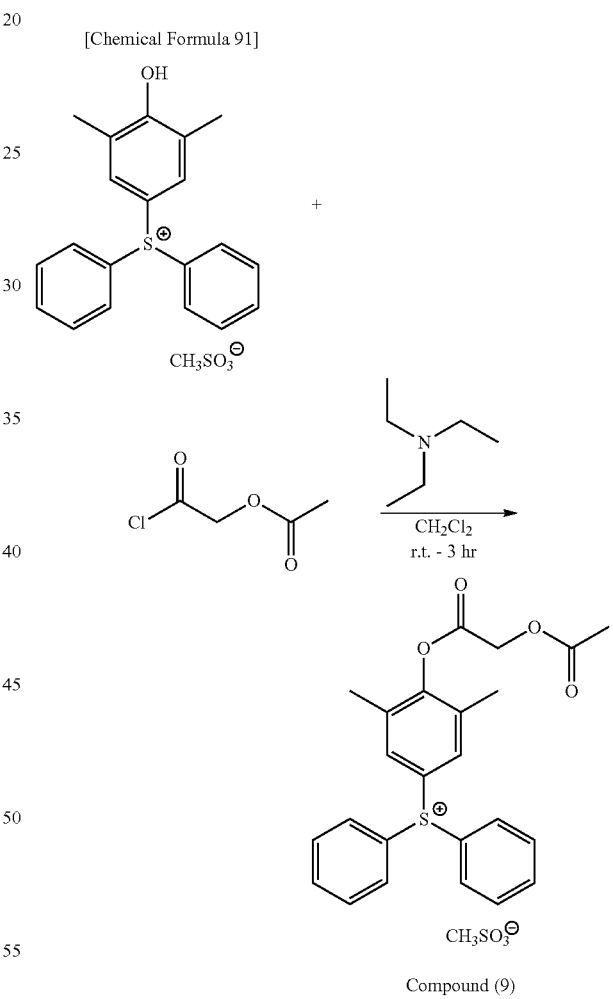

Compound (9)

(iii) Synthesis Example of Compound (B1-1)

1.23 g of the compound (9) was completely dissolved in 9.08 g of dichloromethane. Then, 3.43 g of pure water and 1.31 g of potassium nonafluorobutanesulfonate were added thereto, followed by stirring at room temperature for 1 hour. After the completion of the reaction, washing was conducted with water, and dichloromethane was distilled off under reduced pressure. The resulting oily substance was dried, thereby obtaining 1.55 g of a compound (B1-1).

The obtained compound (B1-1) was analyzed by NMR.

$^1$H-NMR (DMSOd-6,400 MHz): δ(ppm)=7.77-7.89(m, 10H, ArH), 7.70(s,2H, ArH), 5.10(s,2H, OCOCH2O), 2.07-2.19(m,9H, OCOCH3+CH3)

$^{19}$F-NMR (DMSOd-6,376 MHz): δ(ppm)=−77.8, −111.9, −118.4, −122.8

From the results shown above, it was confirmed that the compound (B1-1) had a structure shown below.

$^1$H-NMR (DMSO-d6,400 MHz): δ(ppm)=7.77-7.89(m, 10H,ArH), 7.70(s,2H,ArH), 5.10(s,2H,OCOCH2O), 4.00-4.26(m, 4H, CH2), 2.15-2.22(m, 9H,OCOCH3+CH3), 1.63-1.98(m, 15H, Admantane)

$^{19}$F-NMR (DMSOd-6, 376 MHz): δ(ppm)=−106.6

From the results shown above, it was confirmed that the compound (B1-6) had a structure shown below.

[Chemical Formula 92]

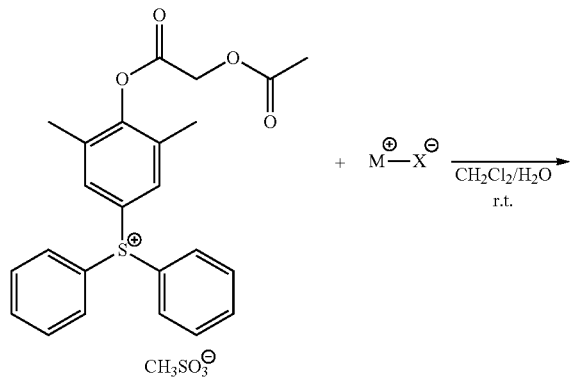

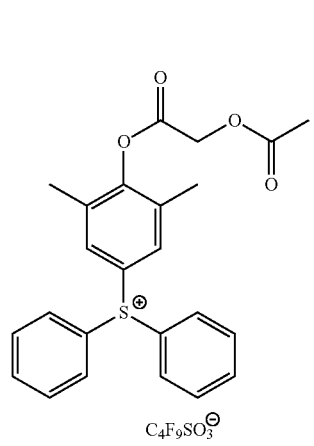

Compound (B1-1)

$\overset{\oplus}{M} \overset{\ominus}{-X} = C_4F_9SO_3^{\ominus}$  $K^{\oplus}$

[Chemical Formula 93]

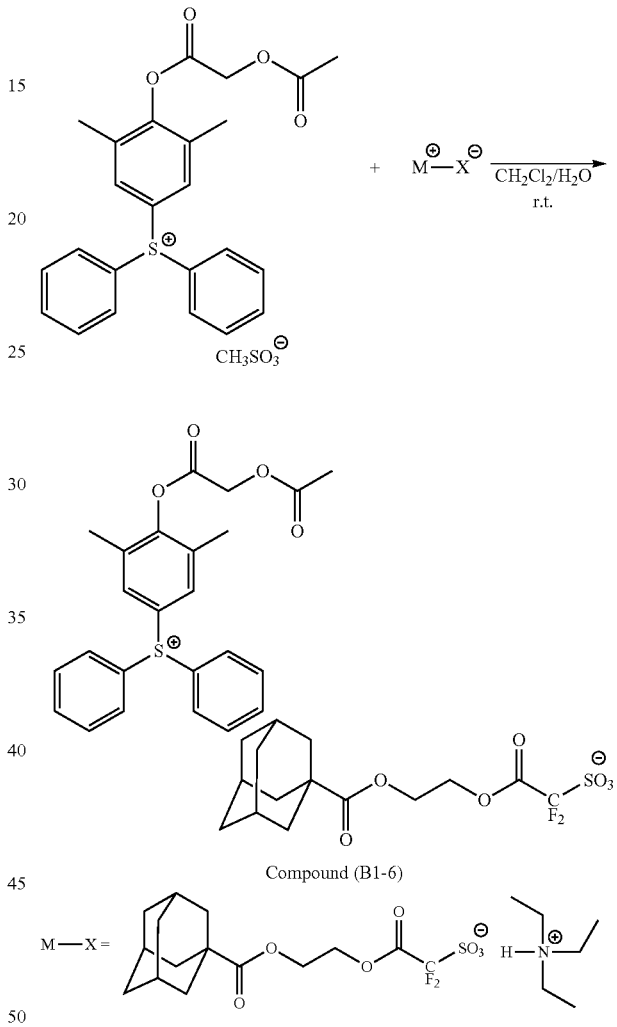

Compound (B1-6)

M—X =

Compound (B1-60)

Example 2

Synthesis of Compound (B1-6)

1.5 g of the compound (9) was completely dissolved in 11.8 g of dichloromethane. Then, 4.44 g of pure water and 2.16 g of a compound (B1-60) were added thereto, followed by stirring at room temperature for 1 hour.

After the completion of the reaction, washing was conducted with water, and dichloromethane was distilled off under reduced pressure. The resulting white solid was dried, thereby obtaining 1.85 g of a compound (B1-6).

The obtained compound (B1-6) was analyzed by NMR.

Examples 3 to 20

The same procedure as in step (iii) of Example 1 was performed, except that the compound (M$^+$-X$^−$) was changed to a compound shown in Tables 1 to 5 (equimolar amount). In this manner, products having an anion and a cation as shown in Tables 1 to 5 (compounds (B1-2) to (B1-5), (B1-7-1), (B1-8), (B1-10) and (B1-12) to (B1-22)) were obtained.

Each of the obtained compounds were analyzed by NMR. The results are shown in Tables 1 to 5. In Tables 1 to 5, "↑" indicates that the cation of the product is the same as that of the compound (B1-1).

TABLE 1

| Compound | NMR | Compound M⁺—X⁻ |
|---|---|---|
| B1-2 | $^1$H-NMR(DMSO-d6, 400 MHz): δ(ppm) = 7.77-7.89(m, 10H, ArH), 7.70(s, 2H, ArH), 5.10(s, 2H, OCOCH2O), 2.07-2.19(m, 9H, OCOCH3 + CH3) $^{19}$F-NMR(DMSO-d6, 376 MHz): δ(ppm) = −75.0 | $CF_3SO_3^{\ominus}$ $K^{\oplus}$ |
| B1-3 | $^1$H-NMR(DMSO-d6, 400 MHz): δ(ppm) = 7.77-7.89(m, 10H, ArH), 7.70(s, 2H, ArH), 5.10(s, 2H, OCOCH2O), 2.07-2.19(m, 9H, OCOCH3 + CH3) $^{19}$F-NMR(DMSO-d6, 376 MHz): δ(ppm) = −77.3, −112.5, −121.7 | $C_3F_7SO_3^{\ominus}$ $K^{\oplus}$ |
| B1-4 | $^1$H-NMR(DMSO-d6, 400 MHz): δ(ppm) = 7.77-7.89(m, 10H, ArH), 7.70(s, 2H, ArH), 5.10(s, 2H, OCOCH2O), 2.07-2.19(m, 9H, OCOCH3 + CH3) $^{19}$F-NMR(DMSO-d6, 376 MHz): δ(ppm) = −116.9, −123.0 | 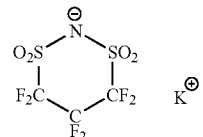 $K^{\oplus}$ |
| B1-5 | $^1$H-NMR(DMSO-d6, 400 MHz): δ(ppm) = 7.77-7.89(m, 10H, ArH), 7.70(s, 2H, ArH), 5.10(s, 2H, OCOCH2O), 2.07-2.19(m, 9H, OCOCH3 + CH3) $^{19}$F-NMR(DMSO-d6, 376 MHz): δ(ppm) = −75.9, −76.0, −114.7 | 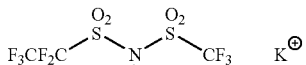 $K^{\oplus}$ |

| Compound | Product Cation | Product Anion |
|---|---|---|
| B1-2 | 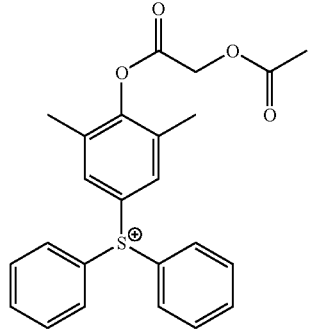 [SMILES: CC(=O)OCC(=O)Oc1c(C)cc([S+](c2ccccc2)c2ccccc2)cc1C] | $CF_3SO_3^{\ominus}$ |
| B1-3 | ↑ | $C_3F_7SO_3^{\ominus}$ |
| B1-4 | ↑ | 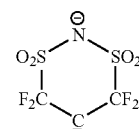 |
| B1-5 | ↑ | 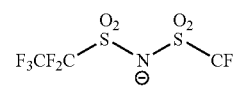 |

TABLE 2

| Compound | NMR | Compound M⁺—X⁻ |
|---|---|---|
| B1-7-1 | $^1$H-NMR(DMSO-d6, 400 MHz): δ(ppm) = 7.77-7.89(m, 10H, ArH), 7.70(s, 2H, ArH), 5.10(s, 2H, OCOCH2O), 4.56-4.49(t, 2H, CH2), 2.15-2.22(m, 9H, OCOCH3 + CH3), 1.63-1.98(m, 15H, Admantane) $^{19}$F-NMR(DMSO-d6, 376 MHz): δ(ppm) = −111.1 | 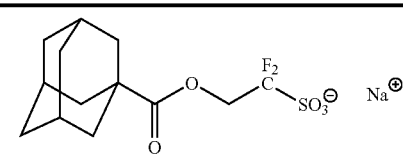 $Na^{\oplus}$ |

TABLE 2-continued

| | | |
|---|---|---|
| B1-8 | $^1$H-NMR(DMSO-d6, 400 MHz): δ(ppm) = 7.77-7.89(m, 10H, ArH), 7.70(s, 2H, ArH), 5.10(s, 2H, OCOCH2O), 4.40-4.49(t, 4H, CH2), 2.15-2.22(m, 9H, OCOCH3 + CH3) <br> $^{19}$F-NMR(DMSO-d6, 376 MHz): δ(ppm) = −106.7, −154.0, −161.5 | pentafluorophenoxyethyl difluorosulfonate sodium salt structure |
| B1-10 | $^1$H-NMR(DMSO-d6, 400 MHz): δ(ppm) = 7.77-7.89(m, 10H, Ar), 7.70(s, 2H, Ar), 5.10(s, 2H, OCOCH2O), 4.78(m, 1H, Sultone), 4.62(t, 1H, Sultone), 3.85(t, 1H, Sultone), 3.34(m, 1H, Sultone), 2.49(m, 1H, Sultone), 1.73-2.22(m, 13H, OCOCH3 + CH3 + Sultone) <br> $^{19}$F-NMR(DMSO-d6, 376 MHz): δ(ppm) = −107.7 | sultone structure, Na⊕ |
| B1-12 | $^1$H-NMR(DMSO-d6, 400 MHz): δ(ppm) = 7.77-7.89(m, 10H, ArH), 7.70(s, 2H, ArH), 5.48(m, 1H, Lactone), 5.10(s, 2H, OCOCH2O), 4.98(s, 1H, Lactone), 4.70~4.58(d, 2H, Lactone), 2.49(m, 1H, Lactone), 2.02-2.22(m, 11H, OCOCH3 + CH3 + Lactone) <br> $^{19}$F-NMR(DMSO-d6, 376 MHz): δ(ppm) = −110.0, −110.2 | lactone structure, Na⊕ |

| Compound | Product Cation | Product Anion |
|---|---|---|
| B1-7-1 | ↑ | adamantane carboxylate-OCH2CF2SO3⊖ |
| B1-8 | ↑ | pentafluorophenoxyethyl-OC(O)CF2SO3⊖ |
| B1-10 | ↑ | sultone-OC(O)CF2SO3⊖ |
| B1-12 | ↑ | lactone-OC(O)CF2SO3⊖ |

TABLE 3

| Compound | NMR | Compound M$^+$—X$^-$ |
|---|---|---|
| B1-13 | $^1$H-NMR(DMSO-d6, 400 MHz): δ(ppm) = 7.77-7.89(m, 10H, ArH), 7.70(s, 2H, ArH), 5.10(s, 2H, OCOCH2O), 2.15-2.22(m, 9H, OCOCH3 + CH3), 1.55-1.87 (m, 17H, Adamantane + CH2) <br> $^{19}$F-NMR(DMSO-d6, 376 MHz): δ(ppm) = −77.7 | adamantyl-CH2-C(O)-N⊖-SO2CF3, Na⊕ |

TABLE 3-continued

| | | |
|---|---|---|
| B1-14 | ¹H-NMR(DMSO-d6, 400 MHz): δ(ppm) = 7.77-7.89(m, 10H, ArH), 7.70(s, 2H, ArH), 5.10(s, 2H, OCOCH2O), 2.77-2.81(m, 1H, Cyclohexyl), 2.15-2.22(m, 9H, OCOCH3 + CH3), 2.04-2.08(m, 2H, Cyclohexyl), 1.73-1.75(m, 2H, Cyclohexyl), 1.56-1.59(m, 1H, Cyclohexyl), 1.07-1.33(m, 5H, Cyclohexyl)<br>¹⁹F-NMR(DMSO-d6, 376 MHz): δ(ppm) = −74.7 | 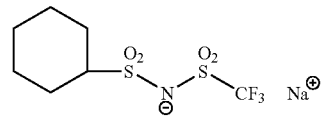 |
| B1-15 | ¹H-NMR(DMSO-d6, 400 MHz): δ(ppm) = 7.77-7.89(m, 10H, ArH), 7.70(s, 2H, ArH), 5.10(s, 2H, OCOCH2O), 2.15-2.22(m, 9H, OCOCH3 + CH3), 1.63-1.98(m, 15H, Adamantane)<br>¹⁹F-NMR(DMSO-d6, 376 MHz): δ(ppm) = −74.5 | 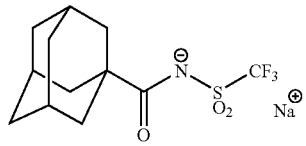 |
| B1-16 | ¹H-NMR(DMSO-d6, 400 MHz): δ(ppm) = 7.77-7.89(m, 10H, ArH), 7.70(s, 2H, ArH), 5.10(s, 2H, OCOCH2O), 2.15-2.22(m, 12H, OCOCH3 + CH3 + Adamantane), 1.99-1.59(m, 12H, Adamantane)<br>¹⁹F-NMR(DMSO-d6, 376 MHz): δ(ppm) = −69.2, −76.0, −112.9 | 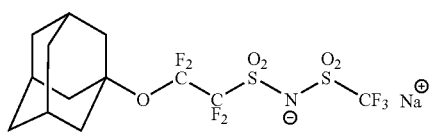 [SMILES: O=S(=O)([N-]S(=O)(=O)C(F)(F)C(F)(F)OC12CC3CC(CC(C3)C1)C2)C(F)(F)F ; [Na+]] |

| | | Product | |
|---|---|---|---|
| Compound | Cation | Anion | |
| B1-13 | ↑ | -N(-)-SO2-CF3) | |
| B1-14 | ↑ | -SO2-CF3) | |
| B1-15 | ↑ | -N(-)-SO2-CF3) | |
| B1-16 | ↑ | -SO2-CF3) | |

TABLE 4

| Compound | NMR | Compound M⁺—X⁻ |
|---|---|---|
| B1-17 | ¹H-NMR(DMSO-d6, 400 MHz): δ(ppm) = 7.77-7.89(m, 10H, ArH), 7.70(s, 2H, ArH), 5.83-5.92(m, 1H, C=CHC), 5.21-5.41(m, 2H, CH2=CC), 5.10(s, 2H, OCOCH2O), 4.45(s, 2H, CCH2O), 2.15-2.22(m, 9H, OCOCH3 + CH3)<br>¹⁹F-NMR(DMSO-d6, 376 MHz): δ(ppm) = −80.0, −113.0 | allyl-O-CF2-CF2-SO3⁻ Li⁺ |
| B1-18 | ¹H-NMR(DMSO-d6, 400 MHz): δ(ppm) = 7.51-7.96(m, 19H, ArH), 5.20(s, 2H, CH2), 5.10(s, 2H, OCOCH2O), 2.15-2.22(m, 9H, OCOCH3 + CH3)<br>¹⁹F-NMR(DMSO-d6, 376 MHz): δ(ppm) = −80.5, −113.7 | naphthylmethyl-O-CF2-CF2-SO3⁻ Li⁺ |

TABLE 4-continued

| | | |
|---|---|---|
| B1-19 | ¹H-NMR(DMSO-d6, 400 MHz): δ(ppm) = 7.77-7.89(m, 10H, ArH), 7.70(s, 2H, ArH), 5.10(s, 2H, OCOCH2O), 2.15-2.22(m, 9H, OCOCH3 + CH3), 1.56-2.09(m, 15H, Adamantane)<br>¹⁹F-NMR(DMSO-d6, 376 MHz): δ(ppm) = −70.1, −113.4 | 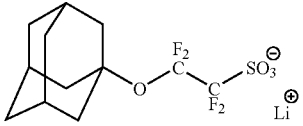 |

| | | Product | |
|---|---|---|---|
| Compound | Cation | Anion | |
| B1-17 | ↑ | 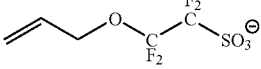 | |
| B1-18 | ↑ | 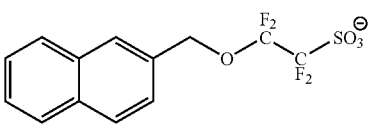 | |
| B1-19 | ↑ | 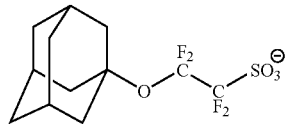 | |

TABLE 5

| Compound | NMR | Compound $M^+$—$X^-$ | Product Cation | Product Anion |
|---|---|---|---|---|
| B1-20 | ¹H-NMR(DMSO-d6, 400 MHz): δ(ppm) = 7.77-7.89(m, 10H, ArH), 7.70(s, 2H, ArH), 5.10(s, 2H, OCOCH2O), 2.15-2.22(m, 6H, OCOCH3 + CH3)<br>¹⁹F-NMR(DMSO-d6, 376 MHz): δ(ppm) = −73.7 | 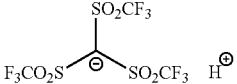 | ↑ | 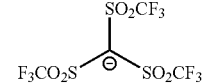 |
| B1-21 | ¹H-NMR(DMSO-d6, 400 MHz): δ(ppm) = 7.77-7.89(m, 10H, ArH), 7.70(s, 2H, ArH), 5.10(s, 2H, OCOCH2O), 2.15-2.22(m, 9H, OCOCH3 + CH3)<br>¹⁹F-NMR(DMSO-d6, 376 MHz): δ(ppm) = −161.1, −149.7, −131.6, −76.2 | 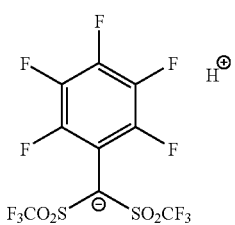 | ↑ | 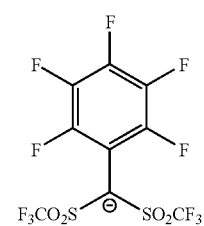 |
| B1-22 | ¹H-NMR(DMSO-d6, 400 MHz): δ(ppm) = 7.77-7.89(m, 10H, ArH), 7.70(s, 2H, ArH), 5.10(s, 2H, OCOCH2O), 2.86-2.90(d, 1H, CH), 2.66-2.74(m, 1H, CH), 2.35-2.38(m, 7H, CH + CH3), 2.15-2.24(m, 10H, OCOCH3 + CH3 + CH), 1.89-1.91(t, 1H, CH), 1.74-1.89(m, 2H, CH2), 1.22-1.29(m, 2H, CH2), 1.03(s, 3H, CH3), 0.71(s, 3H, CH3) | 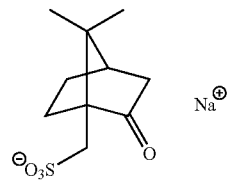 | ↑ | 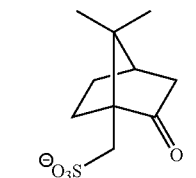 |

Examples 21 to 23

The same procedure as in Example 2 was performed, except that the compound (M⁺-X⁻) was changed to a compound shown in Table 6 (equimolar amount). In this manner, products having an anion and a cation as shown in Table 6 (compounds (B1-7-2), (B1-9) and (B1-11)) were obtained.

Each of the obtained compounds was analyzed by NMR. The results are shown in Table 6. In Table 6, "↑" indicates that the cation of the product is the same as that of the compound (B1-6).

TABLE 6

| Compound | NMR | Compound M+—X− |
|---|---|---|
| B1-7-2 | ¹H-NMR(DMSO-d6, 400 MHz): δ(ppm) = 7.77-7.89(m, 10H, ArH), 7.70(s, 2H, ArH), 5.10(s, 2H, OCOCH2O), 4.56-4.49(t, 2H, CH2), 2.15-2.22(m, 9H, OCOCH3 + CH3), 1.63-1.98(m, 15H, Admantane)<br>¹⁹F-NMR(DMSO-d6, 376 MHz): δ(ppm) = −111.1 | 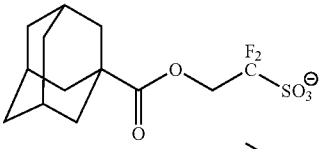 |
| B1-9 | ¹H-NMR(DMSO-d6, 400 MHz): δ(ppm) = 7.77-7.89(m, 10H, ArH), 7.70(s, 2H, ArH), 5.10(s, 2H, OCOCH2O), 4.39-4.42 (t, 2H, CH2), 4.00-4.26(m, 4H, CH2), 2.15-2.22(m, 9H, OCOCH3 + CH3), 1.17-1.50(m, 15H, CH2), 0.79-0.88(t, 3H, CH3)<br>¹⁹F-NMR(DMSO-d6, 376 MHz): δ(ppm) = −106.8 | 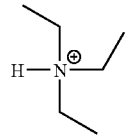 |
| B1-11 | ¹H-NMR(DMSO-d6, 400 MHz): δ(ppm) = 8.74-8.82(m, 2H, Py—H), 7.77-7.89(m, 12H, Py—H + ArH), 7.70(s, 2H, ArH), 5.10(s, 2H, OCOCH2O), 4.54-4.61(m, 4H, CH2CH2), 2.15-2.22(m, 9H, OCOCH3 + CH3)<br>¹⁹F-NMR(DMSO-d6, 376 MHz): δ(ppm) = −106.5 | 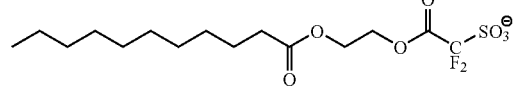 |

| | Product | |
|---|---|---|
| Compound | Cation | Anion |
| B1-7-2 | ↑ |  |
| B1-9 | ↑ | 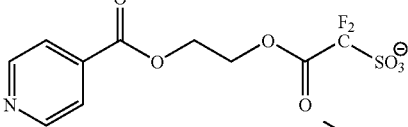 |
| B1-11 | ↑ | 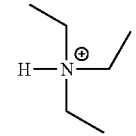 |

<Evaluation of Decomposability in Alkali Developing Solution>

With respect to the compounds (B1-1) to (B1-22), the decomposability in an alkali developing solution was evaluated.

The evaluation was performed by dissolving 0.1 g of a compound in 0.9 g of a 2.38% by weight aqueous tetramethylammonium hydroxide (TMAH) solution at 23° C., and the resulting solution was analyzed by liquid chromatography.

As a result, it was found that each of the compounds (B1-1) to (B1-22) was decomposed to form a carboxylic acid and phenols.

Production of Resist Composition

Examples 24 to 26, Comparative Example 1, Reference Examples 1 and 2

The components shown in Table 7 were mixed together and dissolved to obtain positive resist compositions.

TABLE 7

|  | Component (A) | Component (B) |  | Component (D) | Component (F) | Component (S) |
|---|---|---|---|---|---|---|
| Ref. Ex. 1 | (A)-1 | (B)-1 | — | (D)-1 | (F)-1 | (S)-1 |
|  | [100] | [10] |  | [0.48] | [2.1] | [2700] |
| Ref. Ex. 2 | (A)-1 | (B)-1 | — | (D)-2 | (F)-1 | (S)-1 |
|  | [100] | [10] |  | [0.35] | [2.1] | [2700] |
| Ex. 24 | (A)-1 | (B)-1 | (B)-2 | (D)-2 | (F)-1 | (S)-1 |
|  | [100] | [4] | [4.8] | [0.35] | [2.1] | [2700] |
| Ex. 25 | (A)-1 | (B)-1 | (B)-3 | (D)-2 | (F)-1 | (S)-1 |
|  | [100] | [4] | [4.95] | [0.35] | [2.1] | [2700] |
| Ex. 26 | (A)-2 | — | (B)-2 | (D)-2 | — | (S)-1 |
|  | [100] |  | [9.8] | [1.2] |  | [2100] |
| Comp. Ex. 1 | (A)-2 | (B)-4 | — | (D)-2 | — | (S)-1 |
|  | [100] | [8] |  | [0.35] |  | [2100] |

In Table 7, the reference characters indicate the following. Further, the values in brackets [ ] indicate the amount (in terms of parts by weight) of the component added. "-" indicates that the component was not added.

(A)-1: the aforementioned polymeric compound 1

(A)-2: a polymeric compound 2 represented by chemical formula shown below (Mw=10,000 and Mw/Mn=2.0). In the chemical formula shown below, l, m and n indicate the percentage (molar ratio) of the respective structural units within the polymeric compound 2.

[Chemical Formula 94]

Polymeric compound 2

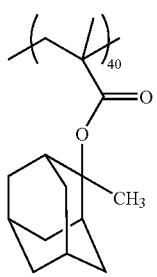
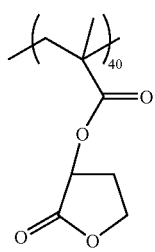
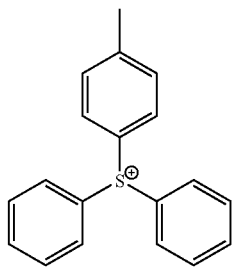

(B)-1: a compound (B2-1) represented by chemical formula shown below

[Chemical Formula 95]

(B2-1)

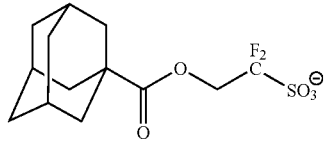

(B)-2: the aforementioned compound (B1-1)
(B)-3: the aforementioned compound (B1-7-1)
(B)-4: (4-methylphenyl)diphenylsulfonium nonafluorobutanesulfonate
(D)-1: stearyldiethanolamine
(D)-2: tri-n-pentylamine.
(F)-1: the aforementioned fluorine-containing resin 1
(S)-1: a mixed solvent of PGMEA/PGME=6/4 (weight ratio)

<Evaluation of Lithographic Properties-(1)>

Using the obtained resist compositions (Reference Examples 1 and 2 and Examples 24 ad 25), resist patterns were formed in the following manner, and the lithography properties were evaluated.

[Formation of Resist Pattern]

An organic anti-reflection film composition (product name: ARC29A, manufactured by Brewer Science Ltd.) was applied to an 12-inch silicon wafer using a spinner, and the composition was then baked at 205° C. for 60 seconds, thereby forming an organic anti-reflection film having a film thickness of 89 nm. Then, each of the resist compositions obtained above was applied onto the anti-reflection film using a spinner, and was then prebaked (PAB) on a hotplate at a temperature indicated in Table 8 for 60 seconds and dried, thereby forming a resist film having a film thickness of 120 nm.

Subsequently, the resist film was selectively irradiated with an ArF excimer laser (193 nm) through a mask pattern (6% halftone), using an ArF immersion exposure apparatus NSR-5609B (manufactured by Nikon Corporation; NA (numerical aperture)=1.07, Cross-pole=0.78/0.97).

Thereafter, a post exposure bake (PEB) treatment was conducted at a temperature indicated in Table 8 for 60 seconds, followed by development for 10 seconds at 23° C. in a 2.38% by weight aqueous solution of tetramethylammonium hydroxide (TMAH) (product name: NMD-3; manufactured by Tokyo Ohka Kogyo Co., Ltd.). Then, the resist film was washed for 30 seconds with pure water, followed by drying by shaking. Further, the resist was subjected to a heat treatment at 100° C. for 60 seconds.

As a result, in each of the examples, an island-structured line and space pattern (hereafter, referred to as "LS pattern") having a space width of 50 nm and a pitch of 100 nm was formed on the resist film.

[Sensitivity]

The optimum exposure dose Eop (mJ/cm$^2$; sensitivity) with which the LS pattern having a space width of 50 nm and a pitch of 100 nm was formed in the "Formation of resist pattern" was determined. The results are shown in Table 8.

[Evaluation of Removability of Space Portion after Development (Solubility after Development)]

An LS pattern targeting a space width of 50 nm and a pitch of 100 nm was formed, and the LS pattern was observed using a scanning electron microscope to determine the size of the space portion (nm).

The closer the size of the space width to 50 nm, the better the removability of the space portion after development (solubility after development). The results are shown in Table 8.

TABLE 8

| | PAB (° C.) | PEB (° C.) | Eop (mJ/cm$^2$) | Size of space portion (nm) |
|---|---|---|---|---|
| Ref. Ex. 1 | 110 | 90 | 15.0 | 42.29 |
| Ref. Ex. 2 | 110 | 90 | 16.1 | 41.45 |
| Ex. 24 | 120 | 90 | 14.8 | 45.6 |
| Ex. 25 | 120 | 90 | 17.9 | 45.2 |

As seen from the results shown in Table 8, the size of the space portion with respect to the resist compositions of Examples 24 and 25 was close to 50 nm, as compared to the size of the space portion with respect to Reference Examples 1 and 2. Thus, it was found that the resist compositions of Examples 24 and 25 exhibited an excellent removability of the space portion, and generation of defects (residue) was suppressed.

From the results of this evaluation, it is expected that compounds (B1-2) to (B1-6) and (B1-8) to (B1-22) would exhibit the same effects as the compounds (B1-1) and (B1-7) which were respectively used in Examples 24 and 25.

<Evaluation of Lithographic Properties-(2)>

Using the obtained resist compositions (Comparative Example 1 and Example 26), resist patterns were formed in the following manner, and the lithography properties were evaluated.

[Formation of Resist Pattern]

An organic anti-reflection film composition (product name: ARC29A, manufactured by Brewer Science Ltd.) was applied to an 8-inch silicon wafer using a spinner, and the composition was then baked at 205° C. for 60 seconds, thereby forming an organic anti-reflection film having a film thickness of 82 nm. Then, each of the resist compositions obtained above was applied onto the anti-reflection film using a spinner, and was then prebaked (PAB) on a hotplate at a temperature indicated in Table 9 for 60 seconds and dried, thereby forming a resist film having a film thickness of 120 nm.

Subsequently, the resist film was selectively irradiated with an ArF excimer laser (193 nm) through a mask pattern (6% halftone), using an ArF exposure apparatus NSR-602 (manufactured by Nikon Corporation; NA (numerical aperture) =0.60, 2/3 annular illumination).

Thereafter, a post exposure bake (PEB) treatment was conducted at a temperature indicated in Table 9 for 60 seconds, followed by development for 30 seconds at 23° C. in a 2.38% by weight aqueous solution of tetramethylammonium hydroxide (TMAH) (product name: NMD-3; manufactured by Tokyo Ohka Kogyo Co., Ltd.). Then, the resist film was washed for 30 seconds with pure water, followed by drying by shaking.

As a result, in each of the examples, an island-structured L/S pattern having a space width of 120 nm and a pitch of 240 nm was formed on the resist film.

[Sensitivity]

The optimum exposure dose Eop (mJ/cm$^2$; sensitivity) with which the LS pattern having a space width of 120 nm and a pitch of 240 nm could be formed was determined. The results are shown in Table 9.

[Evaluation of Line Width Roughness (LWR) and Cross-Sectional Shape of LS Pattern]

With respect to each of the LS patterns formed with the above Eop and having a space width of 120 nm and a pitch of 240 nm, the line width at 5 points in the lengthwise direction of the line were measured using a measuring scanning electron microscope (SEM) (product name: S-9220, manufactured by Hitachi, Ltd.; acceleration voltage: 800V), and from the results, the value of 3 times the standard deviation s (i.e., 3 s) was calculated as a yardstick of LWR. The results are shown in Table 9. The smaller this value is, the lower the level of roughness of the line width, indicating that a LS pattern with a uniform width was obtained.

Further, the cross-sectional shape of the LS pattern was observed using a scanning electron microscope. The results are shown in Table 9.

TABLE 9

| | PAB (°C.) | PEB (°C.) | Eop (mJ/cm²) | LWR | Cross-sectional shape |
|---|---|---|---|---|---|
| Ex. 26 | 110 | 110 | 35 | 10 nm | Rectangular |
| Comp. Ex. 1 | 110 | 110 | 32 | 13 nm | Rounded top |

From the results shown in Table 9, it was confirmed that the resist composition of Example was capable of forming a resist pattern having an excellent shape, as compared to the resist pattern formed using the resist composition of Comparative Example 1.

What is claimed is:

1. A resist composition comprising a base component (A) which exhibits changed solubility in an alkali developing solution under action of acid and an acid-generator component (B) which generates acid upon exposure,
the acid-generator component (B) comprising an acid generator (B1) comprised of a compound having a group represented by formula (I) shown below on a cation moiety thereof:

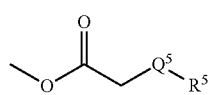

(I)

wherein $R^5$ represents a hydrogen atom or an organic group of 1 to 30 carbon atoms which may have a substituent; and $Q^5$ represents a single and or a divalent linking group.

2. The resist composition according to claim 1, wherein the acid-generator component (B1) is a compound represented by formula (b1-11) shown below:

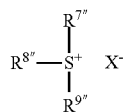

(b1-11)

wherein each of $R^{7\prime\prime}$ to $R^{9\prime\prime}$ independently represents an aryl group or an alkyl group, and two of $R^{7\prime\prime}$ to $R^{9\prime\prime}$ may be mutually bonded to form a ring with the sulfur atom, provided that at least one of $R^{7\prime\prime}$ to $R^{9\prime\prime}$ represents a substituted aryl group having a group represented by general formula (I) as a substituent; and $X^-$ represents an anion.

3. The resist composition according to claim 2, wherein $X^-$ represents an anion selected from the group consisting of a sulfonate anion, an imide anion, a methide anion and a halogen anion.

4. The resist composition according to claim 1, wherein the base component (A) is a base component which exhibits increased solubility in an alkali developing solution under action of acid.

5. The resist composition according to claim 4, wherein the base component (A) comprises a resin component (A1) comprised of a structural unit (a1) derived from an acrylate ester containing an acid dissociable, dissolution inhibiting group.

6. The resist composition according to claim 5, wherein the resin component (A1) further comprises a structural unit (a2) derived from an acrylate ester containing a lactone-containing cyclic group.

7. The resist composition according to claim 5, wherein the resin component (A1) further comprises a structural unit (a3) derived from an acrylate ester containing a polar group-containing aliphatic hydrocarbon group.

8. The resist composition according to claim 1, which further comprises a nitrogen-containing organic compound (D).

9. A method of forming a resist pattern, comprising: forming a resist film on a substrate using the resist composition of claim 1; conducting exposure of the resist film; and alkali-developing the resist film to form the resist pattern.

10. A compound represented by formula (b1-11) shown below:

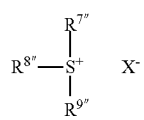

(b1-11)

wherein each of $R^{7\prime\prime}$ to $R^{9\prime\prime}$ independently represents an aryl group or an alkyl group, and two of $R^{7\prime\prime}$ to $R^{9\prime\prime}$ may be mutually bonded to form a ring with the sulfur atom, provided that at least one of $R^{7\prime\prime}$ to $R^{9\prime\prime}$ represents a substituted aryl group having a group represented by formula (I) shown below as a substituent; and $X^-$ represents an anion; and

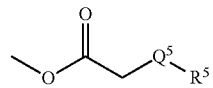

(I)

wherein in formula (I), $R^5$ represents a hydrogen atom or an organic group of 1 to 30 carbon atoms which may have a substituent; and $Q^5$ represents a single bond or a divalent linking group.

11. The compound according to claim 10, wherein $X^-$ represents an anion selected from the group consisting of a sulfonate anion, an imide anion, a methide anion and a halogen anion.

12. An acid generator comprising the compound of claim 10.

* * * * *